US008388532B2

(12) United States Patent
Morgan

(10) Patent No.: US 8,388,532 B2
(45) Date of Patent: Mar. 5, 2013

(54) HOME DIAGNOSTIC SYSTEM

(75) Inventor: Timothy Matthias Morgan, Melbourne (AU)

(73) Assignee: Lachesis Biosciences Pty Ltd, Melbourne (AU)

( * ) Notice: Subject to any disclaimer, the term of this patent is extended or adjusted under 35 U.S.C. 154(b) by 594 days.

(21) Appl. No.: 11/645,022

(22) Filed: Dec. 22, 2006

(65) Prior Publication Data
US 2007/0185391 A1 Aug. 9, 2007

Related U.S. Application Data

(60) Provisional application No. 60/752,357, filed on Dec. 22, 2005.

(30) Foreign Application Priority Data

Dec. 22, 2005 (AU) ................................ 2005907239

(51) Int. Cl.
A61B 5/00 (2006.01)
(52) U.S. Cl. ................ 600/301; 600/300; 705/2; 705/3; 705/4
(58) Field of Classification Search .................. 600/300, 600/301; 128/923
See application file for complete search history.

(56) References Cited

U.S. PATENT DOCUMENTS

| 5,961,332 | A | * | 10/1999 | Joao | 434/236 |
| 6,151,581 | A | * | 11/2000 | Kraftson et al. | 705/3 |
| 6,322,503 | B1 | * | 11/2001 | Sparhawk, Jr. | 600/300 |
| 7,490,085 | B2 | * | 2/2009 | Walker et al. | 1/1 |
| 7,853,456 | B2 | * | 12/2010 | Soto et al. | 705/2 |
| 2002/0123670 | A1 | * | 9/2002 | Goetzke et al. | 600/300 |
| 2003/0036683 | A1 | * | 2/2003 | Kehr et al. | 600/300 |
| 2003/0036923 | A1 | * | 2/2003 | Waldon et al. | 705/2 |
| 2004/0087864 | A1 | * | 5/2004 | Grouse | 600/508 |
| 2004/0122719 | A1 | * | 6/2004 | Sabol et al. | 705/7 |
| 2005/0080462 | A1 | * | 4/2005 | Jenkins et al. | 607/58 |
| 2005/0113650 | A1 | * | 5/2005 | Pacione et al. | 600/300 |
| 2005/0203773 | A1 | * | 9/2005 | Soto et al. | 705/2 |
| 2005/0261558 | A1 | * | 11/2005 | Eaton et al. | 600/300 |
| 2006/0031101 | A1 | * | 2/2006 | Ross | 705/3 |
| 2006/0064322 | A1 | * | 3/2006 | Mascarenhas et al. | 705/2 |
| 2006/0178915 | A1 | * | 8/2006 | Chao | 705/4 |
| 2007/0112585 | A1 | * | 5/2007 | Breiter et al. | 705/2 |
| 2007/0118399 | A1 | * | 5/2007 | Avinash et al. | 705/2 |
| 2008/0306764 | A1 | * | 12/2008 | Weiss-Meilik | 705/2 |

OTHER PUBLICATIONS

Acton, "Basic Need Status and Health-Promoting Self-Care Behavior in Adults," *Western Journal of Nursing Research* 22(7):796-811, 2000.

Andrews et al., "Developing Measures of Perceived Life Quality: Results From Several National Surveys," *Social Indicators Research* 1:1-26, 1974.

(Continued)

*Primary Examiner* — Henry M Johnson, III
*Assistant Examiner* — Bobby Soriano
(74) *Attorney, Agent, or Firm* — Robert Iannucci; Seed IP Law Group PLLC

(57) ABSTRACT

A diagnostic system is disclosed. In one embodiment, the system includes i) an input interface for use by a person to submit user profile data, physical data and psychological data to the system, the physical data representing heart rate, blood pressure, and other biophysical parameters of the person, the psychological data representing quality of life and needs satisfaction and other psychological parameters of the person, ii) an analyzer for processing the physical data and psychological data to generate risk profile data based on criteria data for conditions and iii) an output interface for providing risk profile displays using the risk profile data to present for the person risk levels associated with the conditions.

35 Claims, 36 Drawing Sheets

OTHER PUBLICATIONS

Arnetz, B. B., "Subjective indicators as a gauge for improving organizational well-being. An attempt to apply the cognitive activation theory to organizations," *Psychoneuroendocrinology* 30:1022-1026, 2005.

Berkman et al., "Social Networks, Host Resistance, and Mortality: A Nine-Year Follow-Up Study of Alameda County Residents," *American Journal of Epidemiology* 109(2):186-204, 1979.

Cheng et al., "Heart rate reserve as a predictor of cardiovascular and all-cause mortality in men," *Medicine & Science in Sports & Exercise* 34(12):1873-1878, 2002.

Cooper et al., "Physical Fitness Levels vs. Selected Coronary Risk Factors, A Cross-Sectional Study," *JAMA* 263(2):166-169, 1976.

Deshaies et al., "Serum high-density lipoprotein cholesterol in male and female Olympic athletes," *Medicine and Science in Sports and Exercise* 14(3):207-211, 1982.

Dunstan et al., "The Rising Prevalence of Diabetes and Impaired Glucose Tolerance," *Diabetes Care* 25(5):829-834, 2002.

Eckel et al., "The metabolic syndrome," *Lancet* 365:1415-1428, 2005.

Ferrières et al., "Association Between Resting Heart Rate and Hypertension Treatment in a General Population," *American Journal of Hypertension* 12:628-631, 1999.

Ford et al., "Prevalence of the Metabolic Syndrome Among US Adults," *JAMA* 287(3):356-359, 2002.

Gallagher et al., "Healthy percentage body fat ranges: an approach for developing guidelines based on body mass index[1-3]," *Am. J Clin. Nutr.* 72:694-701, 2000.

Goetzel et al., "The Long-Term Impact of Johnson & Johnson's Health & Wellness Program on Employee Health Risks," *JOEM* 44(5):417-424, 2002.

Haug et al., "Self-Care Among Older Adults," *Soc. Sci. Med.* 29(2):171-183, 1989.

The IDF consensus worldwide definition of the metabolic syndrome, *International Diabetes Federation*, http://www.idf.org, downloaded Apr. 2005.

Leidy, N. K., "Operationalizing Maslow's Theory: Development and Testing of the Basic Need Satisfaction Inventory," *Issues in Mental Health Nursing* 15(3):277-295, 1994.

Lackland, D. T., "Systemic Hypertension: An Endemic, Epidemic, and a Pandemic," *Semin. Nephrol.* 25:194-197, 2005.

Majercsik, E., "Hierarchy of Needs of Geriatric Patients," *Gerontology* 51:170-173, 2005.

Maslow, A. H., *Motivation and Personality.* New York: Harper & Brothers, 1954.

Maslow, A. H., *Toward a Psychology of Being*. 2nd Ed. New York: Van Nostrand Reinhold Company, 1968.

McDaid et al., "Promoting mental well-being in the workplace: A European policy perspective," *International Review of Psychiatry* 17(5):365-373, 2005.

*The Merck Manual of Diagnosis and Therapy* 17th Ed., New Jersey: Merck Research Laboratories, 1999, (pp. 26, 170, & 1633).

*Health Promotion in Nursing Practice*. 4th Ed., New Jersey: Pearson Education, Inc., 2002, (pp. 91-98).

Pfeffer, J. *The Human Equation: Building Profits by Putting People First*. Boston, Massachusetts: Harvard Business School Press, 1998.

Ray, O., "The Revolutionary Health Science of Psychoendoneuroimmunology: A New Paradigm for Understanding Health and Treating Illness," *Ann. N.Y. Acad. Sci.* 1032:35-51, 2004.

Saintfort et al., "Applying Quality Improvement Principles to Achieve Healthy Work Organizations," *Journal on Quality Improvement* 27(9):469-483, 2001.

Short, J., *An Intelligent Life: A Practical Guide to Relationships, Intimacy and Self-Esteem*. Australia: Random House, 2005.

Siegrist, J., "Social reciprocity and health: New scientific evidence and policy implications," *Psychoneuroendocrinology* 30:1033-1038, 2005.

Sobel, D. S., "Rethinking Medicine: Improving Health Outcomes With Cost-Effective Psychosocial Interventions," *Psychosomatic Medicine* 57:234-244, 1995.

Stone, D. H., "Public health in the undergraduate medical curriculum—can we achieve integration?," *Journal of Evaluation in Clinical Practice* 6(1):9-14, 2000.

Timmerman et al., "The Relationship Between Basic Need Satisfaction and Emotional Eating," *Issues in Mental Health Nursing* 22:691-701, 2001.

Vahtera et al., "Effect of organizational downsizing on health of employees," *Lancet* 350:1124-1128, 1997.

Ware et al., *How to Score and Interpret Single-Item Health Status Measures: A Manual for Users of the SF-8 Health Survey*. Lincoln, Rhode Island: QualityMetric Inc., 2001, (pp. 15-19; 20-24; 56-59; 60-63; 70-114).

Westerlund et al., "Workplace expansion, long-term sickness absence, and hospital admission," *Lancet* 363:1193-97, 2004.

Zimmet et al., "Mainstreaming the metabolic syndrome: a definitive definition," *MJA* 183(4):175-176, 2005.

* cited by examiner

| Last data entry | 08-Feb-05 |
|---|---|
| morae™ subscription | |
| Title | |
| First name | |
| Middle name | |
| Last name | |
| Phone contacts Home | |
| Work | |
| Mobile | |
| Email address | |
| Residential street address | |
| Suburb | |
| City | |
| Postcode | |
| State | |
| Country | |
| Date of Birth | |
| Gender (Male or Female) | |
| Occupation | |
| Number of dependents | |

1600

Education

| High school or less | Some college/university | Bachelor's/Undergraduate degree | Graduate/Postgraduate degree |
|---|---|---|---|
| | | | |

Annual household/family income, US$

| < 12,500 | 12,500 - 24,499 | 25,000 - 39,999 | 40,000 - 59,999 | > or = 60,000 |
|---|---|---|---|---|
| | | | | |

Average hours worked per week

| Nil | 1 to 15 | 16 to 29 | 30 to 44 | 45 to 59 |
|---|---|---|---|---|
| | | | | |

Race/ethnicity

| White | Black | Hispanic | Asian/Pacific Islander | Native American |
|---|---|---|---|---|
| | | | | |

Size of social network (number of currently used contacts)

| Marriage/Life partner (Yes or No) | Close friends and relatives | Church membership | Informal and group associations |
|---|---|---|---|
| | | | |

Have you been treated for hypertension previously diagnosed by your doctor? (Y/N)

Have you been diagnosed with diabetes by your doctor? (Y/N)

Have you been treated for lipid abnormalities by your doctor? (Y/N)

Figure 16

Last data entry 08-Feb-05
Current measures
(Select only one unit of measurement for options 4, 6, 8, 10, 12)

Fig. 17A

| Measure | | | | | |
|---|---|---|---|---|---|
| Weight | ☐ kg | or | ☐ lbs | | |
| Height | ☐ cm | or | ☐ ft | ☐ in | |
| Waist circumference | ☐ cm | or | ☐ in | | |
| Hip circumference | ☐ cm | or | ☐ in | | |
| Blood Glucose | ☐ mg/dl | or | ☐ nmol/L | | |
| HDL-Cholesterol | ☐ mg/dl | or | ☐ nmol/L | | |
| Triglycerides (TG) | ☐ mg/dl | or | ☐ nmol/L | | |

1700

Blood Pressure
Diastolic ☐ mmHg
Systolic ☐ mmHg
Heart Rate ☐ beats/min

Health and Well-Being Survey
SF-8™ Health Survey (4-Week Recall)

1. Overall, how would you rate your health during the past 4 weeks?

| Excellent | Very Good | Good | Fair | Poor | Very Poor |
|---|---|---|---|---|---|
| | | | | | |

2. During the past 4 weeks, how much did physical health problems limit your usual physical activities (such as walking or climbing stairs)?

| Not at all | Very little | somewhat | Quite a lot | Could not do physical activity |
|---|---|---|---|---|
| | | | | |

3. During the past 4 weeks, how much difficulty did you have doing your daily work, both at home and away from home, because of your physical health?

| Not at all | Very little | somewhat | Quite a lot | Could not do daily work |
|---|---|---|---|---|
| | | | | |

4. How much bodily pain have you had during the past 4 weeks?

| None | Very mild | Mild | Moderate | Severe | Very Severe |
|---|---|---|---|---|---|
| | | | | | |

5. During the past 4 weeks, how much energy did you have?

| Very much | Quite a lot | Some | A little | None |
|---|---|---|---|---|
| | | | | |

6. During the past 4 weeks, how much did your physical health or emotional problems limit your usual social activities with family or friends?

| Not at all | Very little | Somewhat | Quite a lot | Could not do social activities |
|---|---|---|---|---|
| | | | | |

7. During the past 4 weeks, how much have you been bothered by emotional problems (such as feeling anxious, depressed or irritable)?

| Not at all | Slightly | Moderately | Quite a lot | Extremely |
|---|---|---|---|---|
| | | | | |

8. During the past 4 weeks, how much did personal or emotional problems keep you from doing your usual work, school or other daily activities?

| Not at all | Very little | Somewhat | Quite a lot | Could not do daily activities |
|---|---|---|---|---|
| | | | | |

Modified Basic Needs Satisfaction Inventory  1700

1. How do you feel about how interesting your day to day life is?

| Delighted | Pleased | Mostly satisfied | Mixed | Mostly dissatisfied | Unhappy | Terrible |
|---|---|---|---|---|---|---|
| | | | X | | | |

2. How do you feel about yourself?

| Delighted | Pleased | Mostly satisfied | Mixed | Mostly dissatisfied | Unhappy | Terrible |
|---|---|---|---|---|---|---|
| | | X | | | | |

3. How do you feel about how creative you can be?

| Delighted | Pleased | Mostly satisfied | Mixed | Mostly dissatisfied | Unhappy | Terrible |
|---|---|---|---|---|---|---|
| | | X | | | | |

4. How do you feel about your safety?

| Delighted | Pleased | Mostly satisfied | Mixed | Mostly dissatisfied | Unhappy | Terrible |
|---|---|---|---|---|---|---|
| | X | | | | | |

5. How do you feel about the extent to which your physical needs are met?

| Delighted | Pleased | Mostly satisfied | Mixed | Mostly dissatisfied | Unhappy | Terrible |
|---|---|---|---|---|---|---|
| X | | | | | | |

6. How do you feel about how sincere and honest you are?

| Delighted | Pleased | Mostly satisfied | Mixed | Mostly dissatisfied | Unhappy | Terrible |
|---|---|---|---|---|---|---|
| | X | | | | | |

7. How do you feel about your chance of getting a good job if you went looking for

| Delighted | Pleased | Mostly satisfied | Mixed | Mostly dissatisfied | Unhappy | Terrible |
|---|---|---|---|---|---|---|
| | X | | | | | |

8. How do you feel about the extent to which you are developing yourself and

| Delighted | Pleased | Mostly satisfied | Mixed | Mostly dissatisfied | Unhappy | Terrible |
|---|---|---|---|---|---|---|
| | | | X | | | |

9. How do you feel about the amount of physical work and exercise in your life?

| Delighted | Pleased | Mostly satisfied | Mixed | Mostly dissatisfied | Unhappy | Terrible |
|---|---|---|---|---|---|---|
| | | | X | | | |

10. How do you feel about your own family life – your wife/husband/partner, your marriage, your children, if any?

| Delighted | Pleased | Mostly satisfied | Mixed | Mostly dissatisfied | Unhappy | Terrible |
|---|---|---|---|---|---|---|
| | X | | | | | |

11. How do you feel about what you have to pay for basic necessities, for example food, housing, clothing?

| Delighted | Pleased | Mostly satisfied | Mixed | Mostly dissatisfied | Unhappy | Terrible |
|---|---|---|---|---|---|---|
| | X | | | | | |

12. How do you feel about how much you are really contributing to other people's lives?

| Delighted | Pleased | Mostly satisfied | Mixed | Mostly dissatisfied | Unhappy | Terrible |
|---|---|---|---|---|---|---|
| | | X | | | | |

13. How do you feel about the amount of respect you get from others?

| Delighted | Pleased | Mostly satisfied | Mixed | Mostly dissatisfied | Unhappy | Terrible |
|---|---|---|---|---|---|---|
| X | | | | | | |

14. How do you feel about how secure you are financially?

| Delighted | Pleased | Mostly satisfied | Mixed | Mostly dissatisfied | Unhappy | Terrible |
|---|---|---|---|---|---|---|
| X | | | | | | |

15. How do you feel about how much you are accepted and included by others?

| Delighted | Pleased | Mostly satisfied | Mixed | Mostly dissatisfied | Unhappy | Terrible |
|---|---|---|---|---|---|---|
| | X | | | | | |

*Fig. 17B*

Activity Feedback      2000
Please provide feedback on the activity recommendations that you have participated in since your last report from the list below.

| 2001 | Did you participate in this recommended activity? | |
|---|---|---|
| | Yes | No   2006 |
| HEALTHY EATING | O | O |
| WALKING | O | O |
| SWIMMING | O | O |
| READING | O | O |
| COMMUNITY ARTS COURSE | O | O |
| MENTORING | O | O |
| OVERSEAS TRAVEL | O | O |
| SHOPPING (home improvement) | O | O |

2008

[ Submit ]

Figure 20A

Activity Feedback      2002
Please provide feedback on the activity recommendations that you have participated in since your last report from the list below.

| 2003 | Do you intend to continue with these activities? | |
|---|---|---|
| | Yes | No   2010 |
| HEALTHY EATING | O | O |
| WALKING | O | O |
| SWIMMING | O | O |
| SHOPPING (home improvement) | O | O |

2014      2012

[ View previous screen ]   [ Submit ]

Figure 20B

Activity Feedback            2004
Please provide feedback on your reason(s) for not participating in the following activities.

| 2005 | Too costly | Too time-consuming | Not interested | Too much physical effort | Too much mental effort | Inconvenient location | Other (please type) |
|---|---|---|---|---|---|---|---|
| READING | o | o | o | o | o | o | 2018 |
| COMMUNITY ARTS COURSE | o | o | o | o | o | o | |
| MENTORING | o | o | o | o 2016 | o | o | |
| OVERSEAS TRAVEL | o | o | o | o | o | o | |

2022      2020

View previous screen     Submit

HOME DIAGNOSTIC SYSTEM

RELATED APPLICATIONS

This application claims priority under 35 U.S.C. §119(e) from provisional application No. 60/752,357 filed on Dec. 22, 2005, which is hereby incorporated by reference. This application also claims the benefit of Australian Provisional Application No. 2005907239 filed on 22 Dec. 2005, which is incorporated herein in its entirety by reference.

FIELD

The present invention relates to a diagnostic system. The system may allow an individual to monitor and improve their own health in the privacy of their home.

BACKGROUND

Productivity improvements in work environments are increasingly based upon creative tasks that involve less physical activity and greater use of an individual's cognitive abilities. The changing nature of work is one of the causes of work-related stress and an increasingly sedentary lifestyle. With changes in dietary intake and lifestyle over a period of time (e.g. a growing preference towards conveniently pre-packaged foods, snacks and fast foods), individuals are exposed to greater risks of developing disease conditions of the mind and body that, if uncontrolled, may have a more significant impact on communities than that of HIV/AIDS in terms of morbidity and mortality.

Work-related stress is often associated with organisations in the context of the social/time pressures and uncertainty as a consequence of changes in the workplace (e.g. downsizing, upsizing and mergers and acquisitions of companies) aimed at improving productivity and efficiency of the business for survival (as discussed in Pfeffer J., *The human equation*, 1998, Harvard Business School Press, Boston, Mass.; and Vahtera J. et al., *Effect of organizational downsizing on health of employees*, Lancet 1997, 350, pp. 1124-28; and Westerland H. et al., *Workplace expansion, long-term sickness, and hospital admission*, Lancet, 2004, 363, pp. 1193-97). The challenge is to handle necessary organizational changes to adapt to an increasingly competitive business environment without imposing significant health risks on the workforce to the point where work performance is adversely affected (as discussed in Arnetz B. B., *Subjective indicators as a gauge for improving organizational well-being—An attempt to apply the cognitive activation theory to organizations*, Psychoneuroendocrinology, 2005, 30, pp. 1022-26). A healthy organisation can be defined in terms of both financial success and a work force with few health-related problems (as discussed in Saintfort F. et al, *Applying quality improvement principles to achieve healthy work organizations*, Jt. Comm. J. Qual. Improv., 2004, 27, pp. 469-83). This definition is consistent with the expectations of modern society and the established link between workplace absenteeism due to health-related issues and lost workplace productivity (as discussed in McDaid D., Curran C., Knapp M., *Promoting mental well-being in the workplace: A European policy perspective*, Int. Rev. Psychiatry., 2005, 17(5), pp. 365-73). Studies on work-reward balance have shown the need to maintain appropriate social reciprocity in order to avoid the risk of stress-related disorders. Besides the economic burden of work-related stress disorders, research suggests that the burden on individuals who experience failed reciprocity at work are twice as likely to suffer from incident cardiovascular disease, depression or alcohol dependence compared to those who are not exposed (as discussed in Siegrist J., *Social reciprocity and health: New scientific evidence and policy implications*, Psychoneuroendocrinology, 2005, 30, pp. 1033-38). It is therefore important to avoid and/or reduce work-related stress in an individual when aiming to improve their overall health and well-being.

A less recognised disease condition of the body is metabolic syndrome, which is characterised by the clustering of abdominal obesity, dyslipidemia, hyperglycemia and hypertension, and which has been cited as a major public health challenge worldwide (as discussed in Eckel R H, Grundy S M, Zimmet P X., *The metabolic syndrome*, Lancet, 2005, 365, pp. 1415-1428). Metabolic syndrome is associated with a 5-fold increase in the risk of type-2 diabetes and a 2-fold to 3-fold increase in the risk of cardiovascular disease. Research suggests that the economic burden from metabolic syndrome is significant and rising supported by recent estimates from Australia and the US indicating that 20-25 percent of the adult population have the syndrome (as discussed in Dunstan D W, Zimmet P Z, Welborn T A et al., *The rising prevalence of diabetes and impaired glucose tolerance*, The Australian Diabetes, Obesity and Lifestyle Study, Diabetes Care, 2002, 25, pp. 829-34; and Ford E S, Giles W H, Dietz W H., *Prevalence of the metabolic syndrome among US adults: findings from the third National Health and Nutrition Examination Survey*, JAMA, 2002, 287(3), pp. 356-9).

Effective prevention and/or primary intervention to avoid problems with health and well-being of individuals requires developing an awareness and understanding of the areas necessary for improvement (e.g. concerning diet or lifestyle) and the inherent motivation for individuals to change their current lifestyle/habits. The former requirement can be addressed by having suitably constructed feedback and information sources to guide individuals, and the latter requirement requires developing an understanding of the individual's underlying needs (as discussed in Maslow A., *Toward a psychology of being*, 1968, New York, Van Nostrand Reinhold; and Maslow A. H., *Motivation and personality*, 1970, New York, Harper & Row). For example, a person's underlying needs can be assessed by measuring the individual's basic needs satisfaction inventory to decide the best approach for changes to that particular individual's lifestyle at that point in time. Self-monitoring and self-intervention to prevent disease has been practiced to varying degrees with limited success, and the utility of such methods is becoming less effective because the methods are not personalized to the level required for effective behavioural change.

One of the benefits of large investments in public health, as well as the broad-based community treatment of conditions such as metabolic and cardiovascular diseases, is the greater knowledge and understanding of pre-disease states of the body and mind that acts as a warning sign and impetus to the need for a lifestyle change in order to maintain health and well-being in an individual (as discussed in Stone D. H., *Public health in the undergraduate medical curriculum—can we achieve integration?*, J. Eval. Clin. Prac., 2000 6(1), pp. 9-14). However, modern healthcare has evolved into a complicated morass of multiple professions providing a range of specialised services delivered by an increasingly bureaucratic system of administration. The disproportionate lack of emphasis on broad-based public health initiatives and the inability of individuals to proactively monitor their health and well-being has contributed to an impending global expansion in the incidence of preventable metabolic, cardiovascular and mental disease conditions (as discussed in Lackland D. T., *Systemic hypertension: an endemic, epidemic and a pandemic*, Semin. Nephrol., 2005, 25(4), pp. 194-7). A large unmet need exists for effective primary prevention and/or primary intervention that are based upon health-promoting self-care in the home. Health-promoting self-care is a way for people to take control of their health (as discussed in Haug M. R., Wykle M. L., Namazi K. H., *Self-care among older adults*, Soc. Sci. Med., 1989, 29, pp. 171-83.) and is a strategy for attaining national health goals (as discussed in Pender N. J., 1996, *Health promotion in nursing practice*, 3$^{rd}$ Ed., Stamford Conn., Appleton & Lange). Persons who are more fulfilled and content with themselves and their lives, have physical need satisfaction, and have positive connections with others may be able to make better decisions regarding positive health-promoting self-care behaviours (as discussed in Acton G. J., Malathum P., *Basic Need Status and Health-Promoting Self-Care Behaviour in Adults*, Western J. Nurs. Res., 2000, 22(7), pp. 796-811).

Healthcare professionals such as doctors and pharmacists have traditionally provided face-to-face counseling to individual patients regarding clinical medicine, disease management and related primary healthcare issues. Developments in electronic technology led to the introduction of a range of services that could provide information and feedback to the healthcare professional or patient in an automated and remote manner. The vast majority of such systems are dedicated to improving the management of existing disease states (i.e. disease management) using disease monitoring systems, managing electronic medical record management systems and automating diagnosis of diseases. These systems do not provide preventive healthcare interventions that can motivate a user to prevent a disease and maintain acceptable health and well-being.

For example, U.S. Pat. No. 6,648,820 to Sarel discloses a medical condition sensing system for home monitoring. Sarel discloses the use of remote sensing of a medical condition such as an acute cardiovascular condition and a point scoring system to signify risk levels associated with the medical condition.

U.S. Pat. No. 6,322,504 to Kirshner discloses a computerized interactive method and system for determining a risk of developing a disease and its consequences. Kirshner discloses a method of computerized interaction with the remote user to provide disease risk management. Others have also described further automated methods for: monitoring asthmatic patients as disclosed in U.S. Pat. No. 6,612,985 to Eiffert and Schwartz; monitoring diabetic patients as disclosed in US Patent Publication 2001/0037060 (application Ser. No. 09/778,249) to Thompson and Rubsamen; automatically optimizing a disease therapy as disclosed in U.S. Pat. No. 6,234,964 to Iliff; and identifying at-risk individuals using available existing disease care management data (prescription drug data, clinical lab data, claims data and in-patient information) to avoid high-cost medical events as disclosed in U.S. Pat. No. 6,802,810 to Ciarniello et al.

Others have sought to address the need to provide feedback systems that can motivate a user to improve a current health condition but again these systems do not provide preventive healthcare interventions that can motivate a user to prevent a disease and maintain acceptable health and well-being. For example, U.S. Pat. No. 5,879,163 to Brown and Jensen discloses an on-line health education and feedback system that queries a user's motivational drivers in an attempt to provide customized educational material to the user based on their comprehension, information format preferences and current health condition. Brown and Jensen disclose a method for providing targeted health information to a user to improve the management of a current health condition.

Others have sought to address the need to motivate a user to prevent disease and improve wellness or well-being. These systems provide general feedback on improving risk items associated with physical health condition but do not provide feedback on mental health condition beyond arbitrary scores of mental health that are of limited clinical utility.

For example, U.S. Pat. No. 5,692,501 to Minturn discloses a computer printed form for providing 10-point health/fitness/wellness scales for comparing actual against ideal wellness accompanied by a financial (insurance) incentive feature. Minturn discloses preparing a personal analysis for an individual and providing an assessment of excellent, good, average, poor or dangerous well-being with recommendations for gentle aerobic exercising.

U.S. Pat. No. 5,937,387 to Summerell et al. discloses a system and method for developing and selecting a customized wellness plan for measuring a user's wellness by determining a user's physiological age. Summernell et al. discloses an interactive system for allowing the user to determine the effects of various lifestyle changes or habits (e.g., weight loss, smoking cessation) on the user's physiological age.

U.S. Pat. No. 6,725,209 to Iliff discloses a computerized medical diagnostic and treatment advice system for mental status examination to monitor the level of consciousness in a patient at risk of an acute medical condition.

It is desired to address the deficiencies in the above or at least provide a useful alternative.

SUMMARY OF CERTAIN INVENTIVE ASPECTS

One aspect of the present invention provides a diagnostic system, including: i) an input interface for use by a person to submit user profile data, physical data and psychological data to the system, said physical data representing heart rate, blood pressure, and other biophysical parameters of the person, said psychological data representing quality of life and needs satisfaction and other psychological parameters of the person, ii) an analyzer for processing the physical data and psychological data to generate risk profile data based on criteria data for conditions and iii) an output interface for providing risk profile displays using said risk profile data to present for said person risk levels associated with said conditions.

Another aspect of the present invention provides a diagnostic system, including: i) an input interface for a person to submit physical data and psychological data and user profile data to the system, said physical data and psychological data representing blood pressure, needs satisfaction and other physical and psychological parameters of the person, ii) an analyzer for processing the physical data and psychological data and user profile data to generate activity recommendation data based on attribute data for different activities and iii) an output interface for providing a display using said activity recommendation data to present to said person activity recommendations to address at least one condition.

Still another aspect of the present invention provides a process executed by a diagnostic system, including: i) receiving physical data and psychological data submitted by a person, said physical data and psychological data representing blood pressure and other parameters of the person, ii) processing the physical data and psychological data to a generate results data based on criteria data for conditions, and generate recommendation data using said results data and iii) providing a display using said results data and said recommendation data to present for said person a risk level associated said conditions and activities to address said conditions.

BRIEF DESCRIPTION OF THE DRAWINGS

Embodiments of the present invention are hereinafter described, by way of example only, with reference to the accompanying drawings.

FIG. 16 is a screen display of the personal details and demographic factors provided by a user of the system.

FIG. 17A is a screen display of the user inputs for the system.

FIG. 17B is a screen display of further user inputs for the system.

FIGS. 20A and 20B are screen displays of activity data input interfaces provided by the system.

Figure 23:
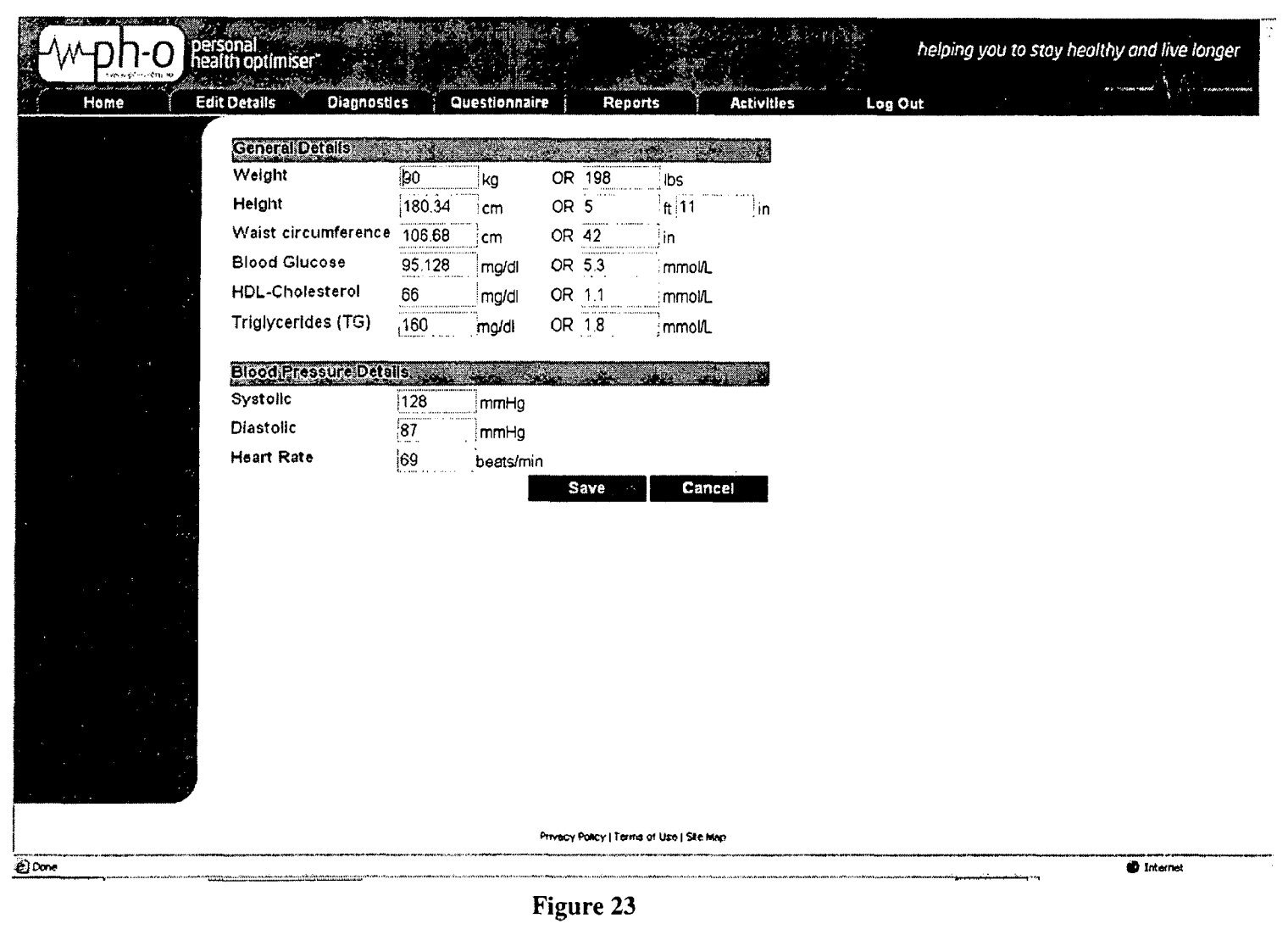

FIGS. 21 to 29 are screen shots of interfaces generated by one exemplary implementation of the system.

DETAILED DESCRIPTION OF CERTAIN INVENTIVE EMBODIMENTS

Figure 1:
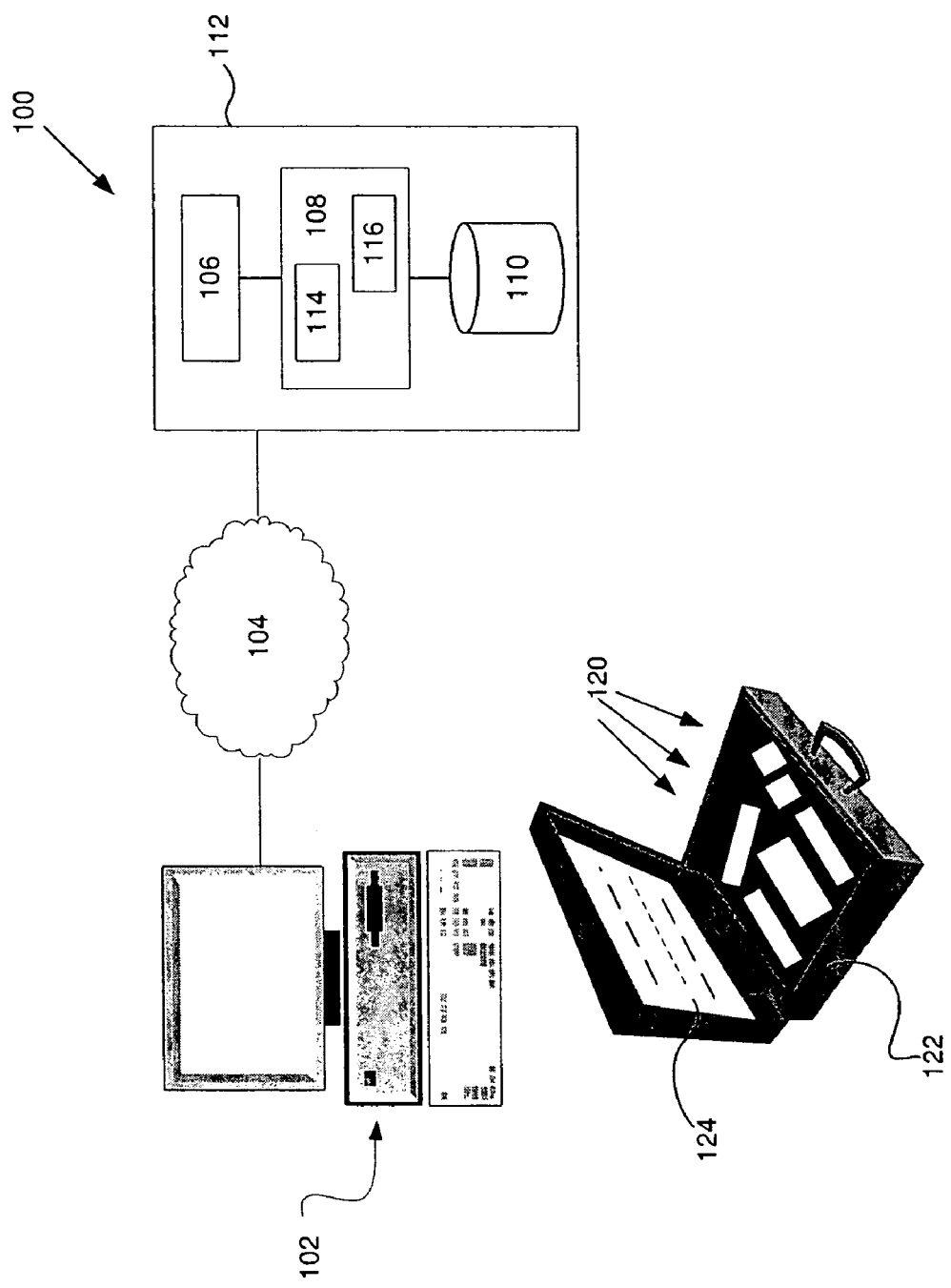
FIG. 1 is a block diagram of one embodiment of a home diagnostic system.

A home diagnostic system 100, as shown in FIG. 1, includes a computer system 112 having a web server 106 that communicates with one or more client devices 102 (e.g. a personal computer, such as that produced by Lenovo Group Limited, Apple Computer Inc., or a personal digital assistant (PDA), such as that produced by Nokia Corporation or Hewlett Pakard Corporation, running an operating system (OS), such as Windows, and a web browser, such as Internet Explorer or Safari) via a communications network 104, such as the Internet. The web server 106 (such as Apache, available from <http://www.apache.org>) handles requests from client devices 102 and sends data back to those clients 102 in response to the requests. The web server 106 passes data received from the clients 102 to an analysis module 108, which processes the data and returns the result to the web server 106. The analysis module 108 communicates with a database 110 (i.e. a relational database, such as MySQL, available from <http://www.mysql.com>).

The analysis module 108, as described below, includes components for compiling and providing static and dynamic web pages for the web server 106 that can be delivered to a client device 102, in response to requests received by the web server 106. The pages are stored or generated by the analysis module and, together with the web server, provide an input interface 114 and an output interface 116 for users of the system 100 who access the interfaces 114, 116 using a client device 102 connected to the Internet 104. The analysis module 108 persists data received from the users in the database 110, and processes the data of the database, as described below, in order to generate pages to render displays for the users using the output interface. The analysis module 108 and its components may be implemented using computer program instruction code written in a computer language, such as Java, Perl or Microsoft.NET. Alternatively, the processes performed by the analysis module 108 and the other components of the server system 1112 can be performed or executed at least in part by dedicated hardware circuits, e.g. application specific integrated circuits (ASICs) or field programmable gate arrays (FPGAs). The components of the server system 112 may also be placed on one computer machine, such as an IBM server, or distributed over a number of machines on the communications network 104.

The home diagnostic system 100 allows users to use, at a remote private environment, (such as the user's home), medical/physiological measurement/diagnostic apparatuses or equipment 120 to obtain measurements and provide physiological measurement data to the analysis module 108 using a client device 102. For example, users may submit measurement data under the control of, or based on instructions provided by, the input interface 114, which causes rendering of one or more interface displays on the client device 102. Alternatively, the client device 102 and the input interface may directly interface with the diagnostic equipment to obtain measurement data. The analysis module 108 processes the measurement data using medical diagnostic criteria, risk analysis procedures and specific individual/population data. The module 108 processes risk factors associated with metabolic syndrome and work-related stress and basic needs satisfaction. The analysis module 108 performs an analysis process 400 to generate report data for the output interface 116 to produce a personalized report for the user that includes measurement/physiological summaries and recommendations aimed at maintaining and/or improving the health and well-being of the user.

The report generated allows users to self-monitor the condition of their body and mind (e.g. with regards to metabolic syndrome, work-related stress and their basic needs), and is also capable of providing advice to consult a health professional (e.g. a doctor or counselor) if the user's risk profile falls outside the generally accepted thresholds of medical diagnostic criteria and/or other risk analysis processes. This aims to provide a timely alert for users to seek secondary intervention, for example drug therapy, for further treatment of their condition if required. The diagnostic system 100 also recommends self-help activities that are consistent with the individual's personal situation as determined by their affective responses to a self-administered modified basic needs satisfaction inventory.

The diagnostic equipment 120 is provided in a kit or package for users. The kit 122 includes equipment 120 for respectively measuring physiological parameters, including blood glucose level, lipid levels, systolic blood pressure, diastolic blood pressure, resting heart rate, waist circumference, weight and height. The kit 122 also includes instructions 124 for accessing the server 112 to which physiological data is to be submitted together with data representing a user's exercise regime, food intake and other relevant lifestyle parameters.

Figure 2:
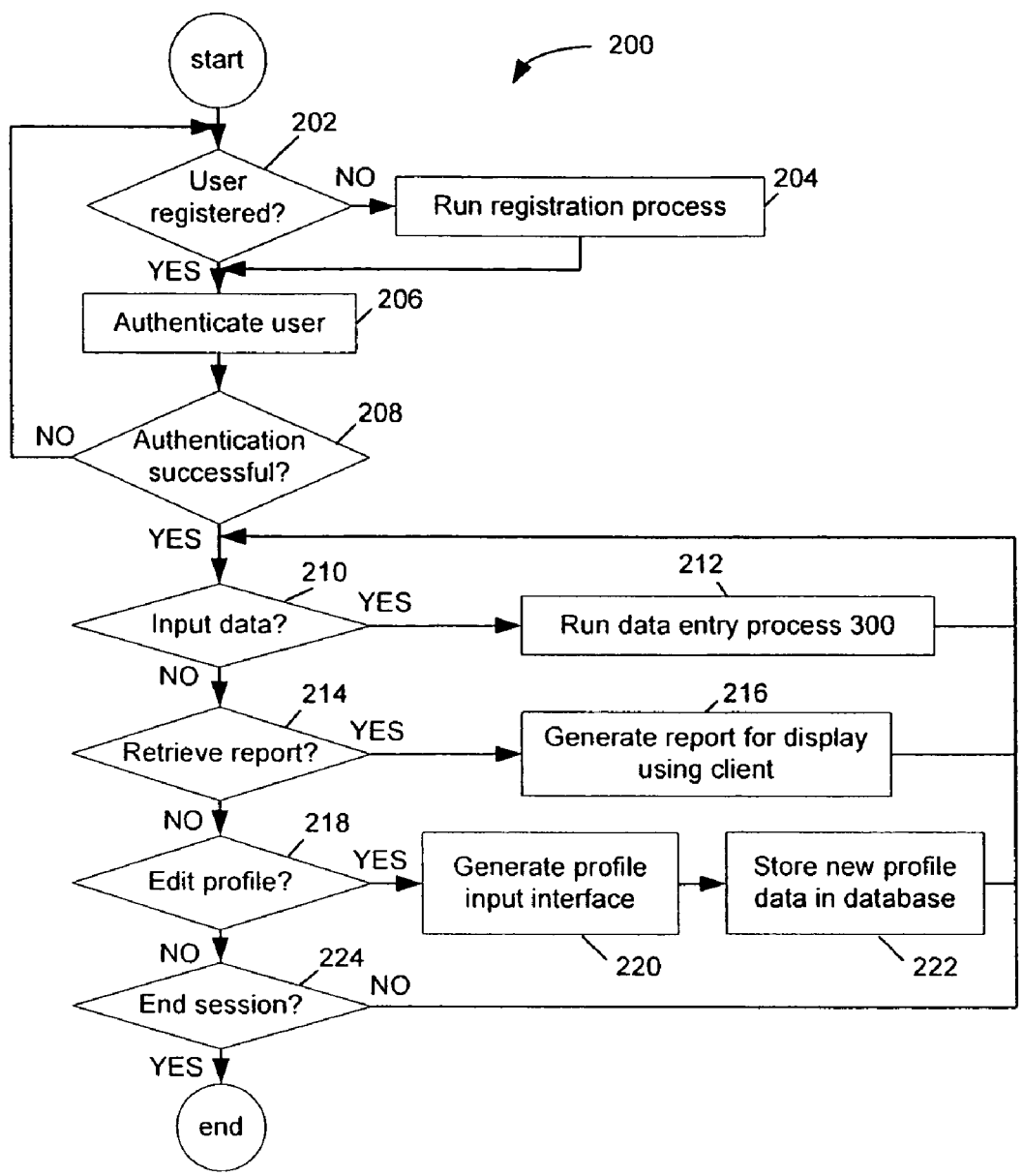
FIG. 2 is a flow diagram of a control process executed by the system.
Figure 22:
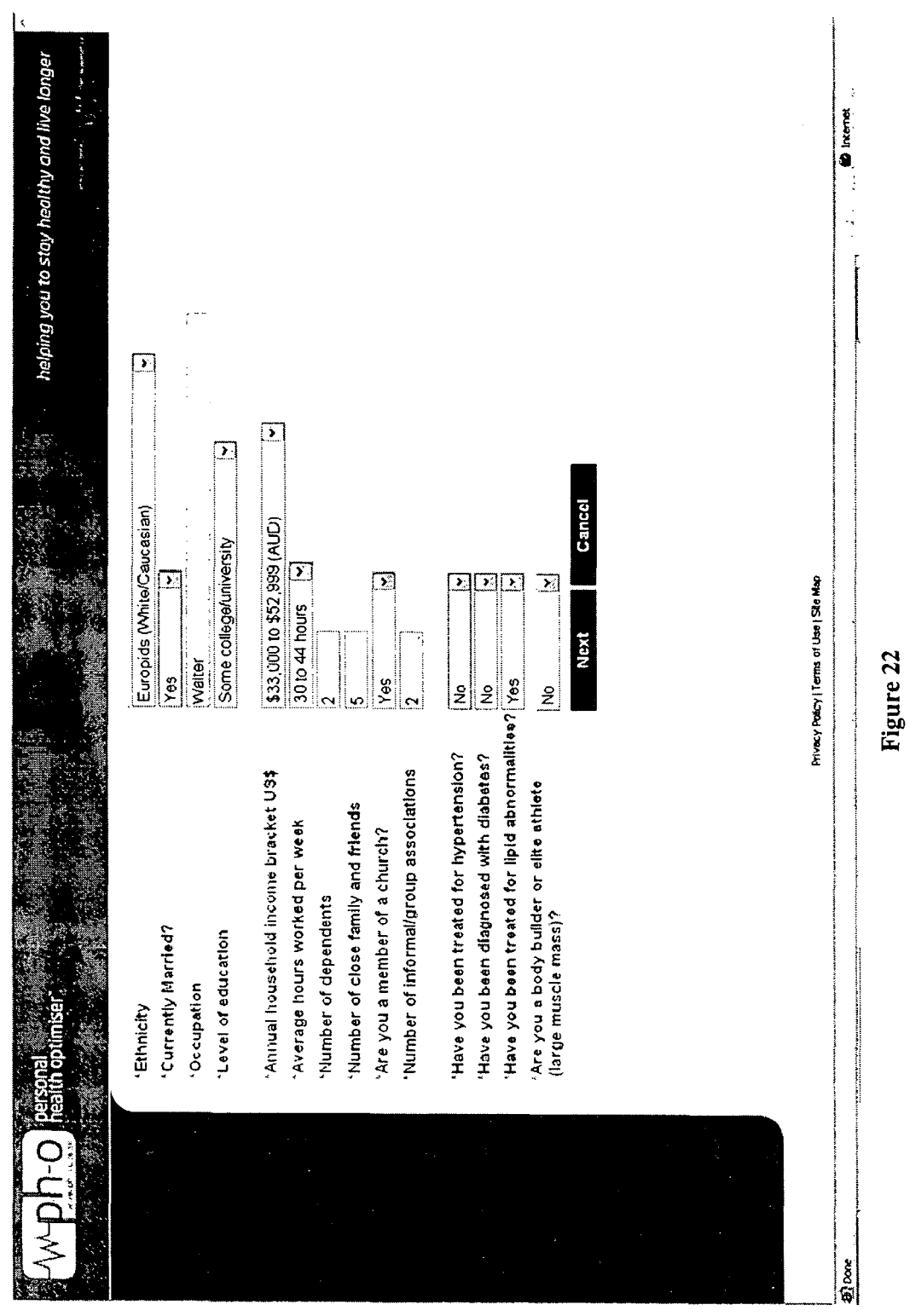

The diagnostic system 100 performs a control process 200, as shown in FIG. 2. The process 200 begins at step 202 where a user uses a client device 102 to communicate with the server 112 and indicate whether the user has previously registered on the server 112 (i.e. by creating a user profile stored in the database 110). If the user indicates that he or she has not been registered, step 202 proceeds to step 204 and the registration process is performed. Step 204 involves using the input interface 114 to generate a profile entry user interface 1600, as shown in FIGS. 16 and 22, in two embodiments, which requires the user to provide authentication details identifying the user (e.g. a preferred username, password, and security question for retrieving these details), personal details (e.g. full name, address, date of birth, gender, contact number, email, occupation and number of dependents), medical history data (e.g. whether the user has been previously diagnosed with Type 2 diabetes, or has been treated for lipid abnormalities or hypertension), and demographic data (e.g. the user's education level, annual income, time commitments for work, race/ethnicity, and the size of the user's social network). These details are stored as a user profile in the database 110.

Optional personal data fields that could also be captured are those that would help identify risk factors for cancer (e.g. family history) with the individual customer then directed to specific cancer risk websites such as that used by the American Cancer Society (www.cancer.org—Great American Health Check).

If the user has already established a user profile, step 202 proceeds to step 206, where the user uses the client device 102 to send authentication details to the web server 106. The web server 106 passes the authentication details to the analysis module 108 to verify the authentication details. For example, at step 206, the analysis module 108 searches the database 110 for an existing user profile associated with the authentication details provided by the user. Step 206 proceeds to step 208 to determine if the user has been registered (e.g. a profile has been found). If so, step 208 proceeds to step 210. Otherwise, step 208 proceeds to step 202.

Figure 3:
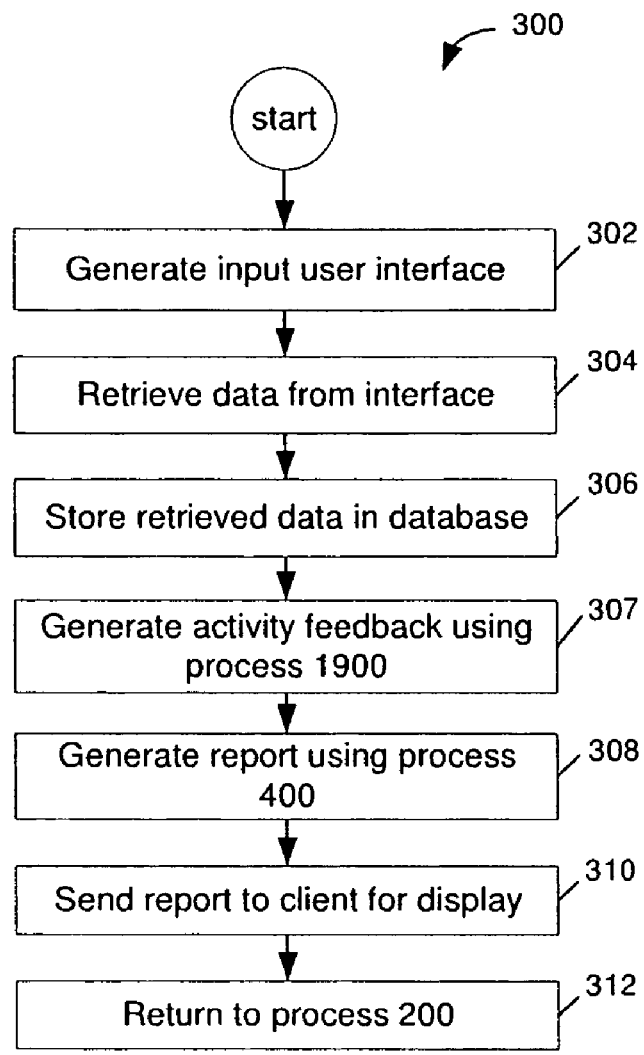
FIG. 3 is a flow diagram of a data entry process of the system.

Step 210 determines whether input from the user represents instructions to perform a data entry task. If not, step 210 proceeds to step 214. Otherwise, step 210 proceeds to step 212 to perform the data entry process 300, as shown in FIG. 3, and step 212 then proceeds to step 210 to detect further user input.

Step 214 determines whether input from the user represents instructions to generate a report of the user's health/psychological condition based on the user's data stored on the server 112. For example, step 216 may generate a report for a selected timeframe that includes the user's medical history/status, graphs and/or recommendations for selected health/psychological parameters based on options selected by the user. If not, step 214 proceeds to step 218. Otherwise, step 214 proceeds to step 216 to generate the report and send the report to the client device 102, and step 216 then proceeds to step 210 to detect further user input.

Step 218 determines whether input from the user represents instructions to update the user's profile stored in the database 110. If not, step 218 proceeds to step 224. Otherwise, step 218 proceeds to step 220 to generate the profile entry user interface 1600 on the client device 102 that includes data values from the user's profile retrieved from the database 110. Step 220 proceeds to step 222 to receive new profile data provided by the user via the profile entry user interface 1600, and the new profile data is stored in the database 110. Step 222 proceeds to step 210 to detect further user input.

Step 224 determines whether input from the user represents instructions to end the session with the server 112. If so, process 200 ends. Otherwise, step 224 proceeds to step 210 to detect further user input.

FIG. 3 is a flow diagram of the data entry process 300 of the analysis module 108 for processing body-related (physical) parameters and mind-related (psychological) parameters provided by a user, and for generating a report display based on these parameters using the output interface 116. An example of the report display 1800 generated using process 300 is shown in the screen shots in FIGS. 18A to 18D and FIGS. 27 and 28. Process 300 begins at step 302 by generating a data entry user interface 1700 of the input interface 114 for display on the client device 102, as shown in the screen shots in FIGS. 17A and 17B and FIGS. 23 and 24. The data entry user interface 1700 includes one or more data entry fields for the user to provide body-related measurement parameters and mind-related parameters. A data entry field may include a selectable drop-down menu, a check box, a radio button, a graphical sliding scale that allow selection based on movement of a pointer on the scale, or a combination of the above.

The user obtains measurements for body-related parameters using the diagnostic equipment 120 and enters the measurements into the corresponding data entry fields (e.g. by following instructions provided with the kit 122 or displayed on the input user interface 1700). For example, users may use a standard portable whole-blood diagnostic device such as the CardioChek™ portable glucose and lipid monitor (manufactured by Polymer Technology Systems, Inc.) to measure:

i) Fasting blood glucose levels, and optionally, ketones levels; and ii) Blood lipids levels, High-Density Lipoprotein (HDL) cholesterol levels, trigylceride levels, and optionally, total cholesterol levels and Low-Density Lipoprotein (LDL) cholesterol levels.

Users may use a standard portable blood pressure monitor 120 to measure:

iii) Systolic blood pressure levels;

iv) Diastolic blood pressure levels; and v) Resting heart rate.

Users may use a standard measuring tape 120 to measure:

vi) Waist circumference (e.g. at the level of the belly button);

vii) Hip circumference (e.g. at the level of the top of the pelvic bone); and viii) Height.

Users may use a standard bathroom scale to measure;

ix) Weight.

Alternatively, the device 102 interfaces with one or more measurement/diagnostic equipment 120 and automatically obtains measurements, which are transmitted to the server 112 for processing.

The data entry user interface 1700 includes data entry fields for users to provide mind-related parameters based on the time at which data entry is performed by the user. For example, when data entry is performed each calendar month or every three calendar months, the data entry user interface 1700 includes data entry fields corresponding to a health and well-being survey (e.g. the SF-8™ Health Survey with a 4-Week Recall period, as described at <http://www.qmetric.com/>), or alternatively, a dynamically generated health assessment (e.g. a combined SF-8™ and SF-36™ as described at <http://www.amIhealthy.com/>, or alternatively the World Health Organisation Quality of Life survey (WHO-QoL-BREF, Australian Version, May 2000). Users may also perform an optional Cognitive Health Assessment survey (e.g. Neurotrax® or Cogstate®), which requires visitation from a trained technician. The Cognitive Health Assessment survey is recommended for customers at risk from neurodegenerative disorders, e.g. Alzheimer's disease.

The data entry user interface 1700 includes data entry fields for users to provide mind-related parameters as part of a modified basic needs satisfaction inventory (modified BNSI) survey, which is administered once every calendar month or every three calendar months (or more or less frequently as required). The modified BNSI survey was developed to measure an individual's self-perception of their self-actualization, self-esteem, safety/security and physical needs. The needs used for self-esteem measurement relied on the contemporary definition of self-esteem developed from long-term clinical practice that included an equal weighting for both love/belonging needs and individuality needs (as discussed in Short J., *An Intelligent Life. A Practical Guide to Relationships, Intimacy and Self-Esteem*, 2005, Random House, Milson Point, NSW, Australia). The range of specific questions used in the modified BNSI survey has been validated (as discussed in Andrews F. M., Withey S. B. *Developing Measures of Perceived Life Quality: Results From Several National Surveys*, Social Indicators Research, 1974, 1, pp. 1-26; and Leidy N. K., *Operationalizing Maslow's Theory: Development and Testing of the Basic Need Satisfaction Inventory*, Issues in Mental Health Nursing, 1994, 15, pp. 277-95).

Figure 24:
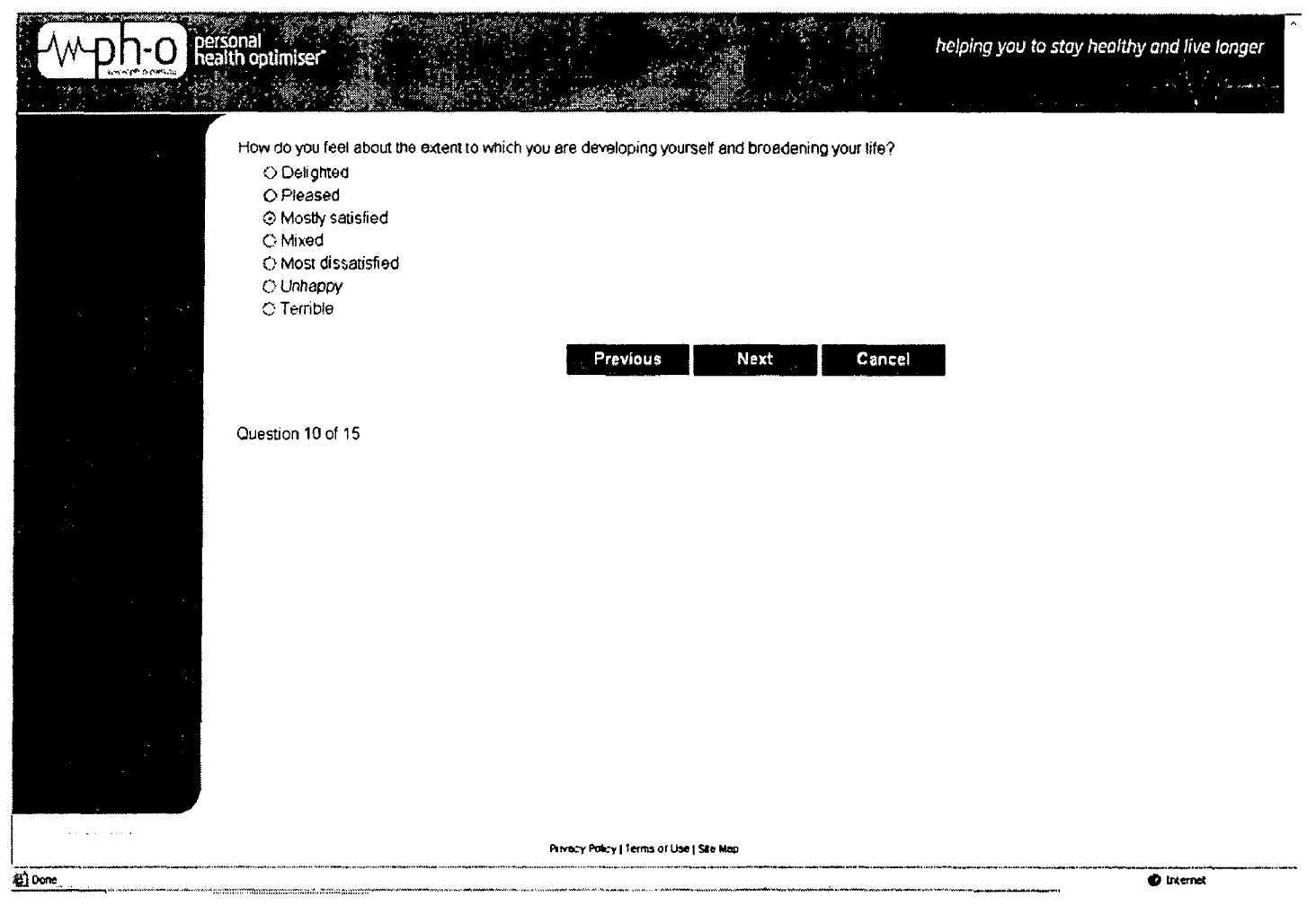

For each question in the modified BNSI survey, a 7-point scale is used to assess the user's affective responses, in one embodiment, which requires users to select a position on the scale to represent one of the following range of feelings: i) Delighted; ii) Pleased; iii) Mostly satisfied; iv) Mixed (about equally satisfied and dissatisfied); v) Mostly dissatisfied; vi) Unhappy; and vii) Terrible, as shown in FIG. 24. This scale has been validated (as discussed in Andrews F. M., Withey S. B., *Developing Measures of Perceived Life Quality: Results From Several National Surveys*, Social Indicators Research, 1974, 1, pp. 1-26). Each position on the 7-point has a different points value, for example, 7 points (if the user selected "Delighted"), 6 points (if the user selected "Pleased"), 5 points (if the user selected "Mostly satisfied"), 4 points (if the user selected "Mixed"), 3 points (if the user selected "Mostly dissatisfied"), 2 points (if the user selected "Unhappy") and down to 1 point (if the user selected "Terrible").

A random number generator is used to randomise the order of the questions used in the modified BNSI survey with a randomisation constraint preventing any two questions from the same sub-grouping (i.e. self-actualization, self-esteem, safety/security and physical needs) being asked in a row. This constraint, and the total number of questions being equal to 15, provides for a sufficiently large enough number of different question combinations which are sufficient to maintain long-term validity of the modified BNSI survey given its proposed frequency of use. An example of the questions asked in each category of the modified BNSI survey is shown in Table 1, where each question begins with "How do you feel about . . . ".

TABLE 1

| | |
|---|---|
| Self-actualisation needs | "how interesting your day to day life is?" |
| | "the extent to which you are developing yourself and broadening your life?" |
| | "how much you are really contributing to other people's lives" |
| Self-esteem - Love/belonging needs | "yourself" |
| | "your own family life - your wife/husband/partner, your marriage, your children, if any?" |
| | "how much you are accepted and included by others?" |
| Self-esteem - Individuality needs | "how creative you can be?" |
| | "how sincere and honest you are?" |
| | "the amount of respect you get from others?" |
| Safety/security needs | "your safety?" |
| | "your chance of getting a good job if you went looking for one?" |
| | "how secure you are financially?" |
| Physical needs | "the extent to which your physical needs are met?" |
| | "the amount of physical work and exercise in your life?" |
| | "what you have to pay for basic necessities, for example food, housing, clothing?" |

Figure 4:
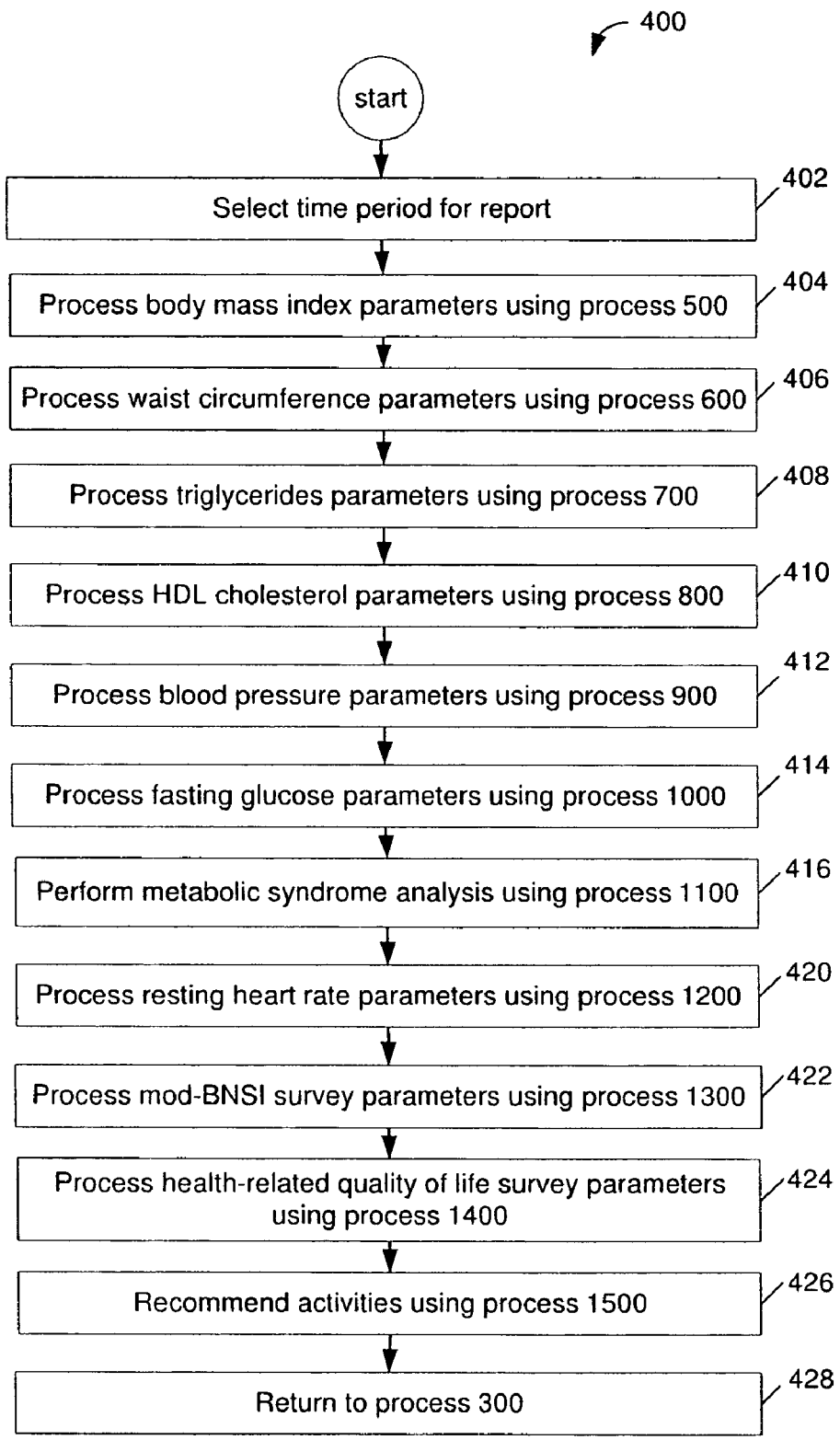
FIG. 4 is a flow diagram of an analysis process of the system.
Figure 19:
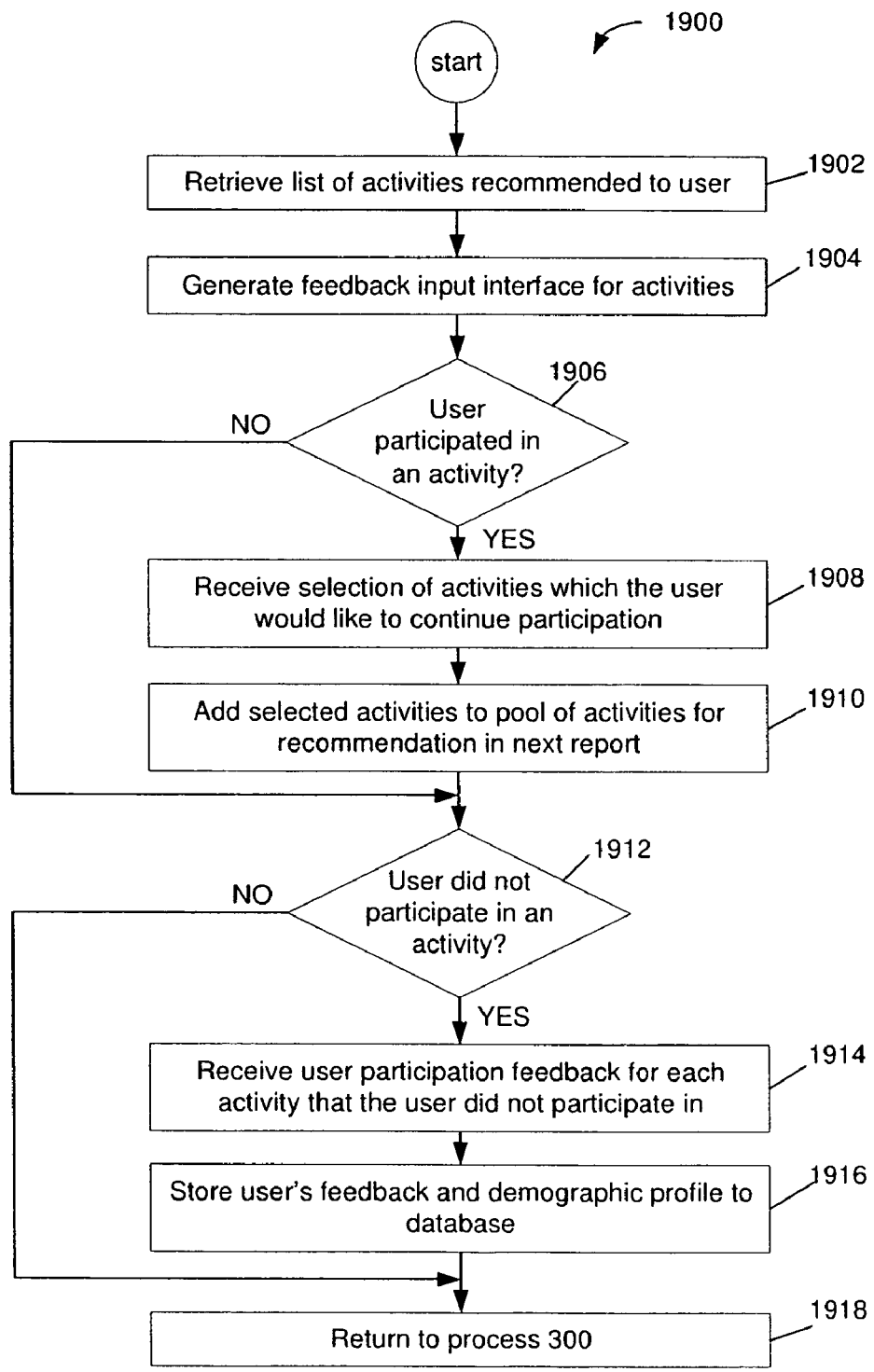
FIG. 19 is a flow diagram of an activity data input process of the system.
Figure 21:
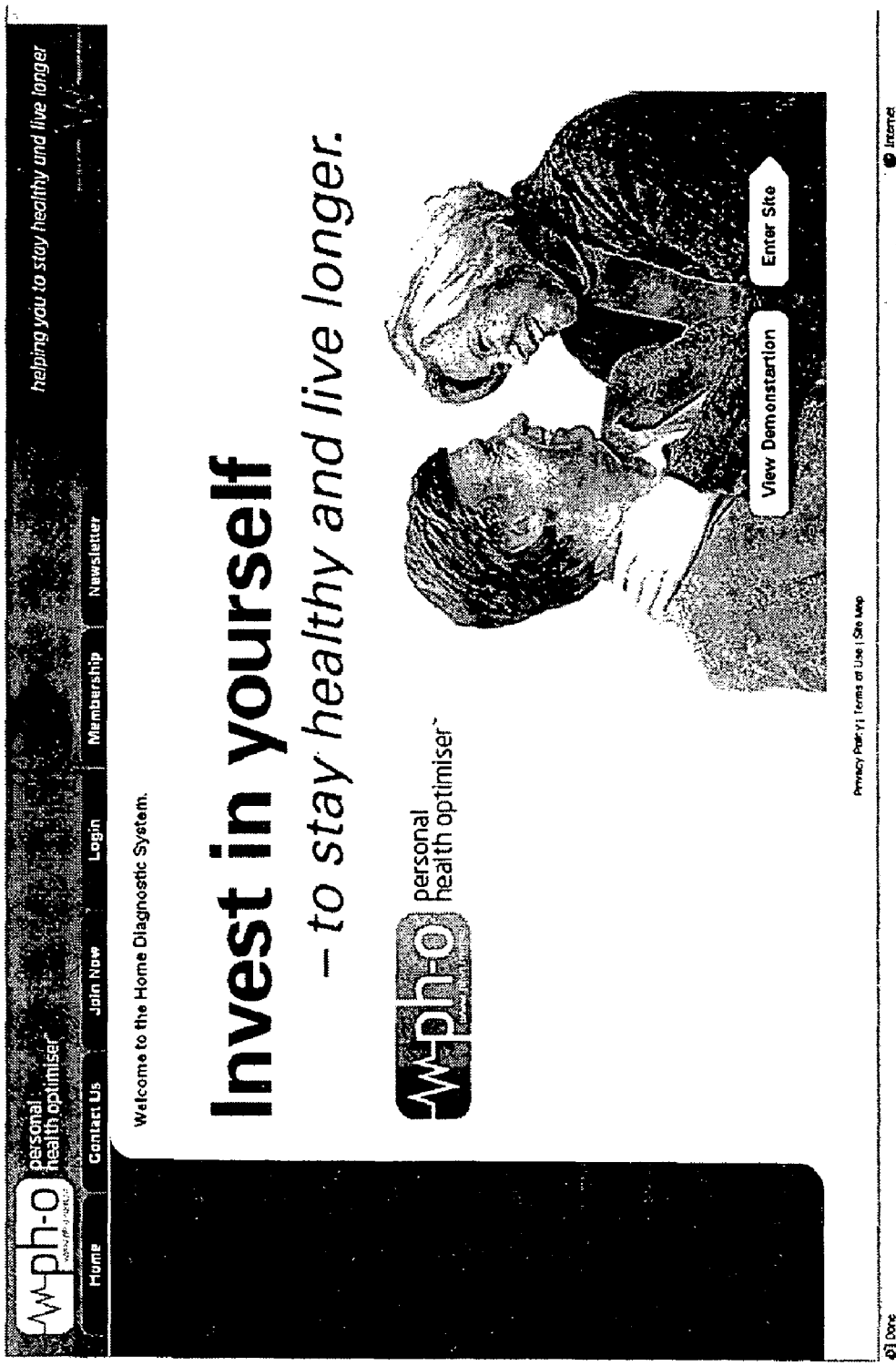
Figure 25:
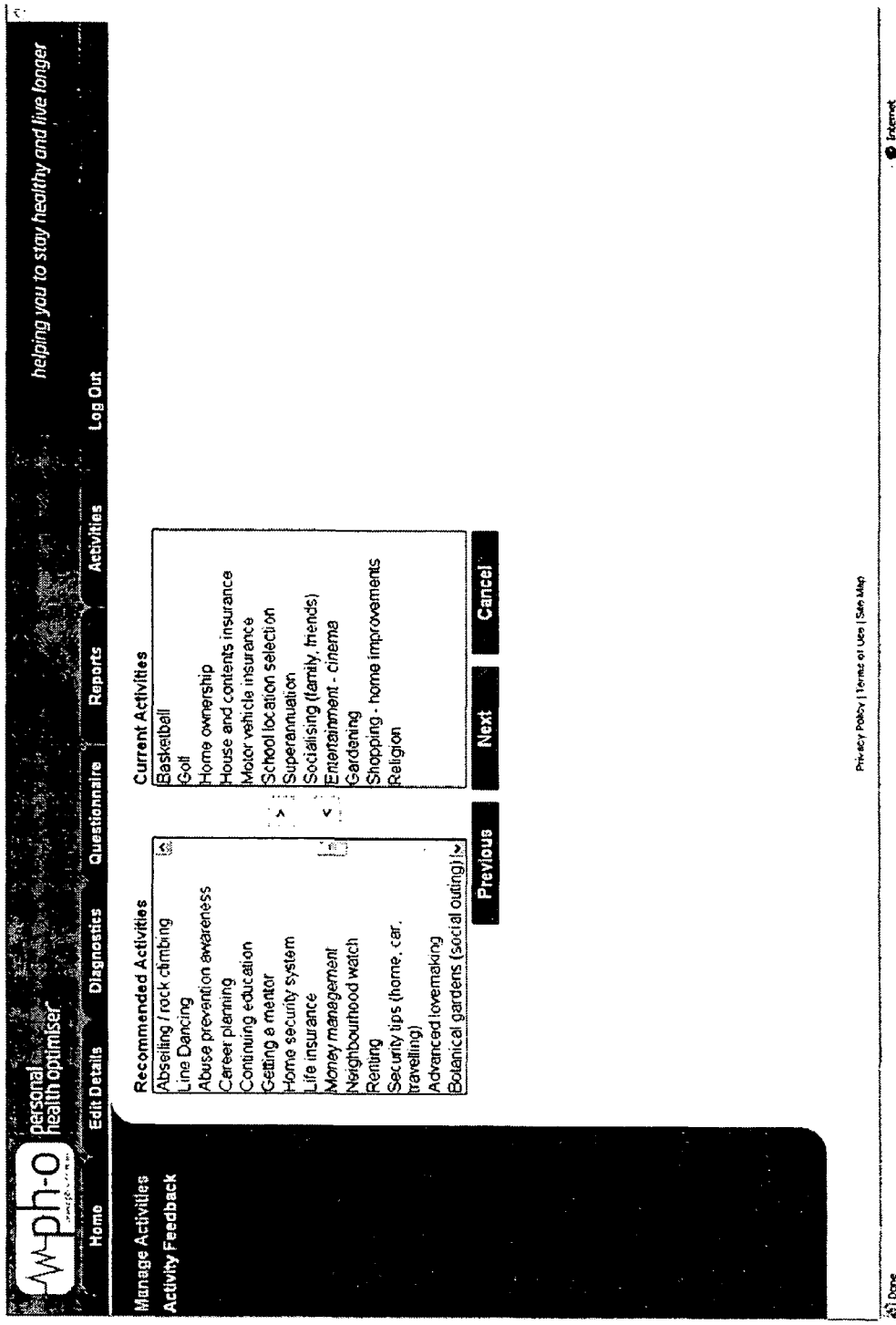
Figure 26:
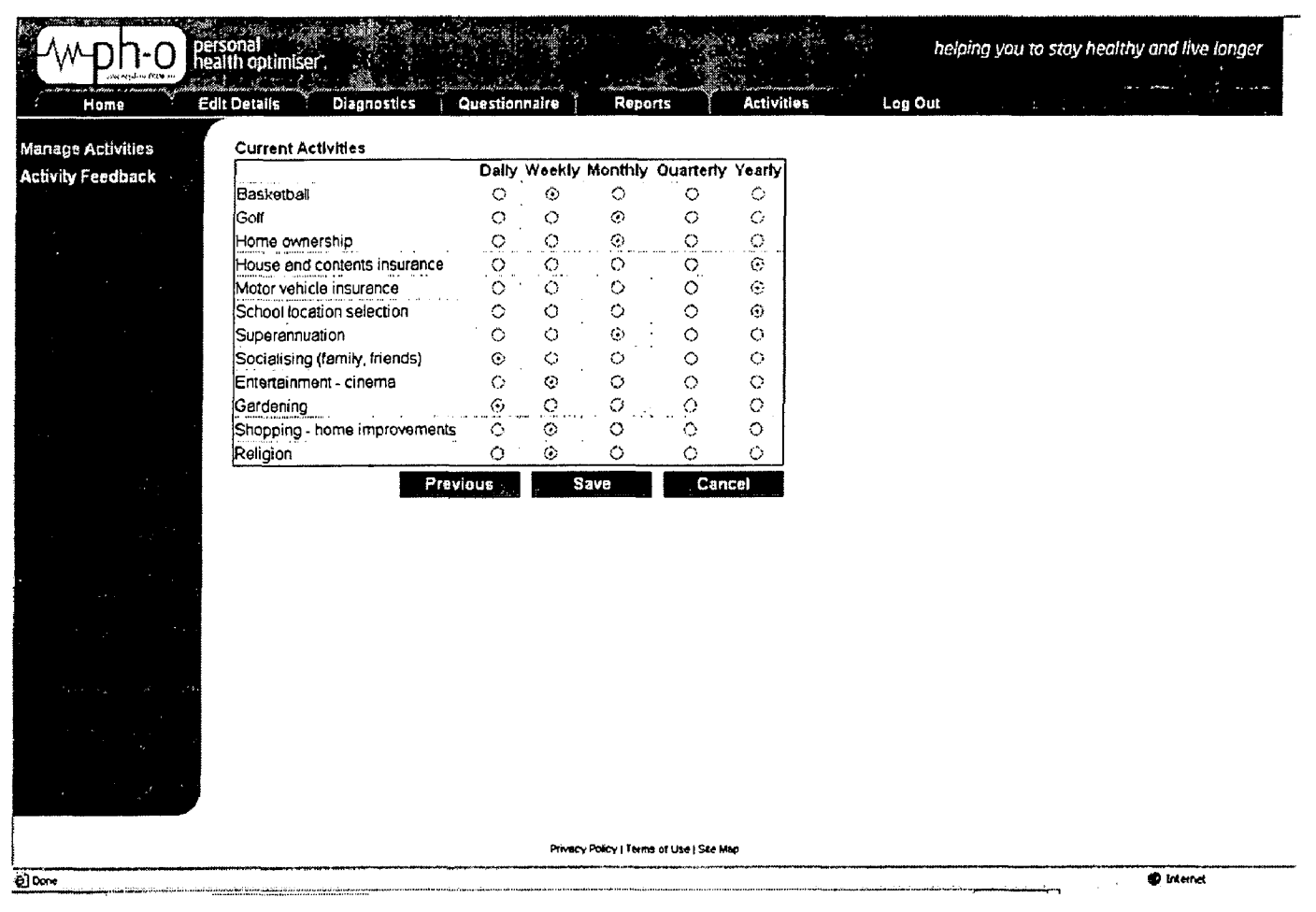

At step 304, the device 102 transmits the body-related and mind-related parameter data to the server 112 for processing. At step 306, the analysis module 108 stores the received parameter data in the database 110 in association with the corresponding user profile and the date on which the parameter data was obtained. At step 307, the analysis module 108 uses an activity monitoring process 1900 (as shown in FIG. 19) to retrieve a list of activities, as shown in FIG. 25, recommended to the user for treatment and generates an activity feedback interface, as shown in FIG. 26, of the input interface 114 for receiving the user's feedback on each of those activities. At step 308, the analysis module 108 retrieves the user's body-related and mind-related parameter data from the database 110, and generates a report using an analysis process 400 (as shown in FIG. 4) based on these parameters. For example, the analysis process 400 generates recommendation data and other data values based on the parameter data received, and stores this data in the database. This data is later retrieved by the analysis process 400 to generate the report display. The report display can be optionally saved in a convenient file format (e.g. a Portable Document Format (PDF) file, which is readable using the Adobe Acrobat Reader available from <http://www.adobe.com>) for printing a hardcopy from the client device 102, storage on the client device 102 and/or transmission from the client device 102 to the user's doctor if so desired by the user. At step 310, the server 112 sends the report data to the client device 102 for display to the user. At step 312, execution returns to process 200.

FIGS. 20A to 20C and FIG. 26 illustrate a screen display of the user inputs for the activity feedback mechanism that obtains the individual's compliance with and views regarding the activities recommended. Whilst the reliability of this data is currently determined by the accuracy of the individual customer's subjective responses regarding activity compliance, primary independent verification of activity compliance would most likely impact the customer's privacy. Therefore the main primary independent verification for activity compliance is public mortality data for the customer. Publicly validated mortality data and subjective health-related quality of life data are considered sufficient given the need to balance the individual customer's right to privacy regarding their health and well-being.

FIG. 4 is a flow diagram of the analysis process 400 for generating a report display of the user's health/physiological/psychological condition based on the user's parameter data (i.e. body-related and mind-related parameters derived from measurements and surveys) received from the input user interface 1700, and based on the user's parameter data stored in the database 110. The report display presents a report of the output interface 116 which provides a display of a risk profile of the user and also includes various personalized activity recommendations that should improve the risk profile of the user. The risk profile includes indication of a risk level the user has in relation to one or more conditions. The parameter data is processed using the analysis process 400 of the analysis module 108 that considers an individual human as a holistic being with dynamic interacting subsystems:

i) Biophysical subsystem (represented by diagnostics data and anthropometrics)—which relates to physical processes ii) Cognitive subsystem (represented by Neurotrax, Cogstate assays)—which relates to neural processes iii) Psychosocial subsystem (represented by SF-8 Health and Well-Being survey and modified BNSI survey or other social-relatedness scores)—which relates to psychological processes (emotional existence which includes belonging and territory) and social processes (relationships which allow us to define our understanding of our psyche).

The analysis process 400 executes a deductive procedure that works on the primary assumption that in order to maintain or improve health and well-being, all these dynamic interacting subsystems work harmoniously to create an equilibrium in the functions of the mind and body (i.e. that there is a continuous mind and body interaction that is responsible for homeostasis and psychostasis; as discussed in Ray O, *The revolutionary health science of psychoendoneuroimmunology—A paradigm for understanding health and treating illness*, Ann. N.Y. Acad. Sci., 2004, 1032, pp. 35-51).

To give an example of this interaction, emotional existence is defined by our belonging/love and individuality which both make up our self esteem, but which only has psychological meaning if it is defined with reference to other people i.e. our social relationships. To put this in a medical context, providing people with the resources to address their psychosocial needs can provide important coping skills during times of stress.

This holistic approach for the deductive procedure is important to the primary prevention and primary intervention recommended to users by the system 100 because it is based on their perceived holistic need. This serves to prevent or minimise behaviours that the user may undertake and which are detrimental to their health and well-being. For example, it has been recognised that unfulfilled needs (e.g. a low modified BNSI survey score) can lead to emotional stress (i.e. a low Mental Summary Measure (MCS-8) score on the SF-8™ survey), which has been cited (for example, as discussed in Timmerman G. M., *The relationships between basic need satisfaction and emotional eating*, Issues Ment. Health Nurs., 2001, 22(7), pp. 691-701) as a common cause of over-eating and obesity or obesity-related conditions. Metabolic syndrome is a pre-disease state for obesity, cardiovascular disease and type-II diabetes, and the detection of metabolic syndrome is useful for predicting the likely deterioration of a person's biophysical health.

The range and nature of the recommendations for primary prevention and/or primary intervention generated by the analysis process 400 is based on the needs identified from an evaluation of each subsystem (i.e. the biophysical, cognitive and psychosocial subsystems) and the system as a whole (i.e. the user as a holistic human-being). The analysis process 400 is sufficiently detailed and multi-layered so as to allow assessment of the holistic health and well-being of the individual customer down to each subsystem in order to provide the individual with specific suggestions for personalized preventive medicine. The analysis process 400 specifically focuses on the biophysical and psychosocial subsystems with the cognitive processes being optionally tested depending on the age of the subject.

To aid with evaluation of each subsystem (i.e. the biophysical, cognitive and psychosocial subsystems), various parameters can be evaluated by the analysis process 400 comparing them to contemporary medical practice guidelines (e.g. as published by the International Diabetes Association, National Heart Foundation and World Health Organization) and/or customer population data residing in the database 110.

In the process 400, a user is classified as having an acceptable health and well-being if the following minimum criteria are met for each of the following conditions for the dynamic interacting subsystems, based on the user's parameter data:

1. Biophysical processes:
   i) The lack of presence of metabolic syndrome; and
   ii) Body mass index within the normal range (refer to Table 2 below, as extracted from *The Merck Manual*, 17th Edition, 1999, Merck and Co., Inc. p. 26); and
   iii) A self-assessed Physical Health-Related Quality of Life survey score equal to or greater than the $75^{th}$ percentile population-based score for the age and gender of the user (e.g. a Physical Summary Measure (PCS-8) score on the SF-8™ survey equal to or greater than the $75^{th}$ percentile score—details of the PCS-8 score are described below with reference to FIG. 14); and 2. Cognitive processes:
   i) Cognitive function that allows the customer to maintain at least the literacy, problem solving, conversational and emotional level of that of a normal human with a chronological age of 11 years; and 3. Psychosocial processes:
   i) A self-assessed Mental Health-Related Quality of Life survey score equal to or greater than the $75^{th}$ percentile population-based score for the age and gender of the user (e.g. a Mental Summary Measure (MCS-8) score on the SF-8™ survey equal to or greater than the $75^{th}$ percentile score—details of the MCS-8 score is described below with reference to FIG. 14); and
   ii) A self-assessed modified Basic Needs Satisfaction Inventory (BNSI) survey score of greater than or equal to 83.3% with no single sub-grouping (i.e. self-actualization, self-esteem, safety/security and physical needs) scoring less than 16.6%.

TABLE 2

| Nutritional Status | Body Mass Index (Weight, kg/Height, m²) | Percentage Change From Desirable Weight |
|---|---|---|
| Undernourished | | |
| Grade 2 | <16 | >−30 |
| Grade 1 | 16 to 17.9 | −30 to −21 |
| Thin | 18 to 19.9 | −20 to −11 |
| Normal | 20 to 25 | −10 to +10 |
| Fat | 25.1 to 26.9 | +11 to +20 |
| Obese | | |
| Grade 1 | 27 to 29.9 | +21 to +32 |
| Grade 2 | 30 to 40 | +33 to +77 |
| Grade 3 | >40 | >+77 |

Referring to FIG. 4, process 400 begins at step 402 by selecting the time period covered by the report. The home diagnostic system 100 may set the time period to a predetermined default value (e.g. for a timeframe covering the previous 1, 3, 6 or 12 months), or alternatively, the time period can be specified by the user.

Step 402 proceeds to step 404 to process the user's body mass index parameters. Step 406 processes the user's waist circumference parameters. Step 408 processes the user's triglyceride parameters. Step 410 processes the user's HDL-cholesterol parameters. Step 412 processes the user's blood pressure parameters. Step 414 processes the user's fasting glucose parameters. Step 416 analyses the user's parameters to determine whether the user has metabolic syndrome. Step 420 processes the user's resting heart rate parameters. Step 422 processes the user's responses to the modified BNSI survey. Step 424 processes the user's response to the SF-8 Health Survey. Step 426 generates activity recommendations based on the analysis performed from at steps 404 to 424. Step 426 then proceeds to step 428, where execution returns to process 300. Details of the processing performed by the analysis module 108 for each of steps 404 to 426 is described below.

Figure 5:
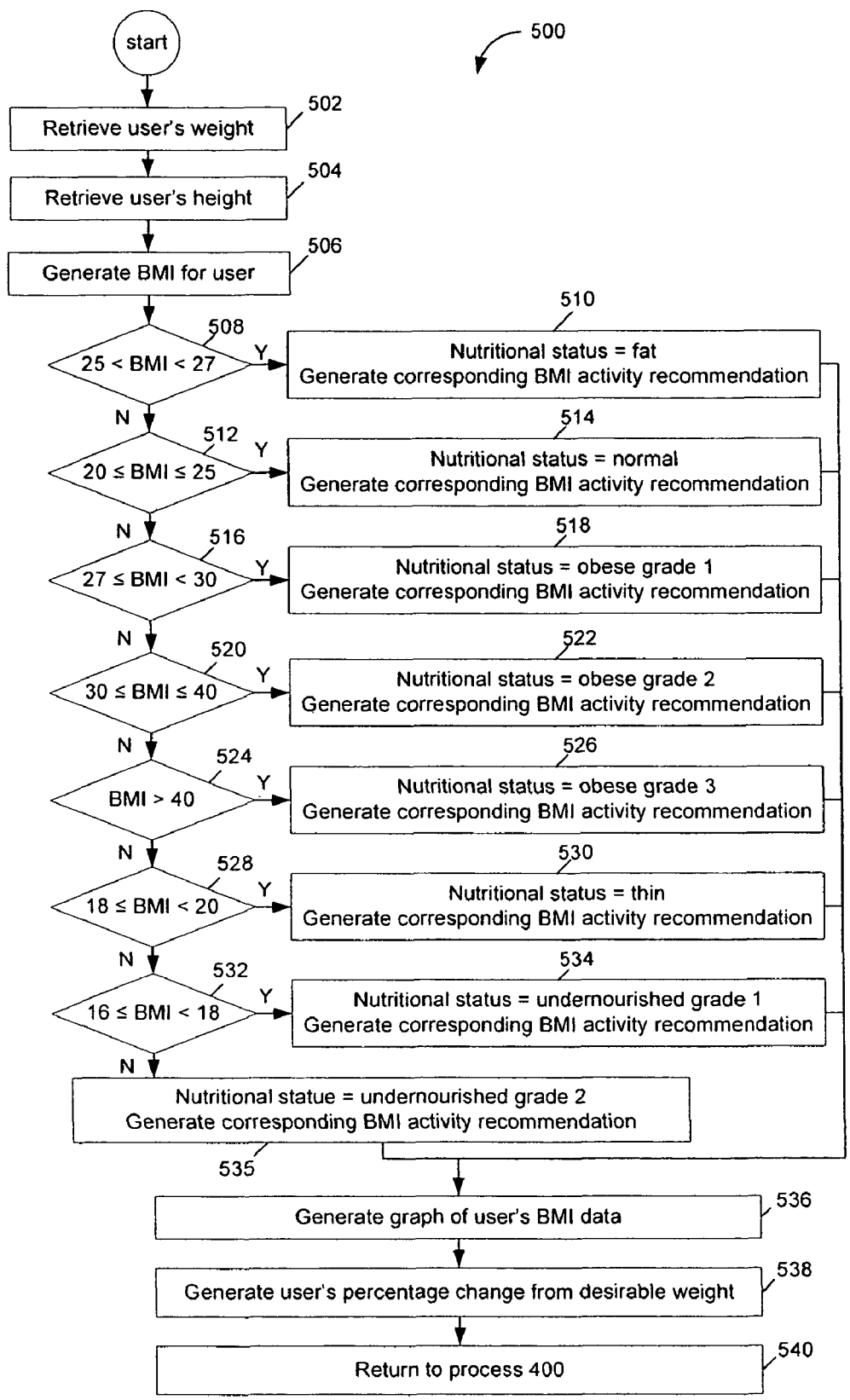
FIGS. 5 to 15 are flow diagrams of sub-processes of the analysis process.

FIG. 5 is a flow diagram of the process 500 for generating recommendations based on the user's body mass index (BMI) parameter value derived from the user's weight and height, and graphical representations of the changes in the value of the user's BMI parameter value over the time period selected at step 402.

For users with a normal BMI parameter value (as shown in Table 2), no intervention would be recommended to the user for improving this biophysical parameter. For users with a BMI parameter value that meets the criteria for the fat or grade 1 obese categories, both dietary and exercise primary intervention activities would be recommended. For users with a BMI parameter value that meets the criteria for the thin category, dietary primary intervention activities would be recommended. If the user's BMI parameter value meets the criteria for grade 2 obesity, grade 3 obesity, grade 1 undernourished or grade 2 undernourished categories, then the recommendation would be to seek professional medical help (e.g. from a general physician). A dietician and exercise instructor would also be suggested for those individual's with the socio-economic capacity to do so (i.e. annual household income in the upper 40th percentile e.g. $\geq$US$40,000 or approximately $\geq$AU$53,000).

Process 500 begins at step 502 by retrieving the user's weight data from the database 110 (e.g. as measured on different dates). At step 504, the user's height data is retrieved from the database 110 (e.g. as measured on different dates). Step 504 proceeds to step 506 to generate the user's BMI parameter value using Equation 1 based on user's weight data and height data for each date that such data was recorded:

$$\text{Body Mass Index} = \frac{\text{Weight}}{\text{Height} \times \text{Height}} \qquad \text{Equation 1}$$

Step 506 proceeds to step 508 to determine whether the user's most recent BMI parameter value is between 25 and 27. If so, step 508 proceeds to step 510 to determine that the user's nutritional status as "Fat" as depicted by 1892 in FIG. 18C, and generates a corresponding BMI activity recommendation (e.g. "You need to undertake moderate exercise and/or dietary intervention") as depicted by 1894 in FIG. 18C. Otherwise, step 508 proceeds to step 512.

Step 512 determines whether the user's most recent BMI parameter value is between in the range of 20 to 25, inclusive. If so, step 512 proceeds to step 514 to determine that the user's nutritional status as "Normal", and generates a corresponding BMI activity recommendation (e.g. "Okay, no recommendation based on your BMI"). Otherwise, step 512 proceeds to step 516.

Step 516 determines whether the user's most recent BMI parameter value is greater than or equal to 27 and less than 30. If so, step 516 proceeds to step 518 to determine that the user's nutritional status as "Obese Grade 1", and generates a corresponding BMI activity recommendation (e.g. "You need to undertake moderate exercise and dietary intervention"). Otherwise, step 516 proceeds to step 520.

Step 520 determines whether the user's most recent BMI parameter value is between 30 and 40, inclusive. If so, step 520 proceeds to step 522 to determine that the user's nutritional status as "Obese Grade 2", and generates a corresponding BMI activity recommendation (e.g. "You need to undertake significant exercise and dietary intervention under professional medical supervision"). Otherwise, step 520 proceeds to step 524.

Step 524 determines whether the user's most recent BMI parameter value is over 40. If so, step 524 proceeds to step 526 to determine that the user's nutritional status as "Obese Grade 3", and generates a corresponding BMI activity recommendation (e.g. "You need to seek urgent professional medical help. You need to undertake significant exercise and dietary intervention under professional medical supervision"). Otherwise, step 524 proceeds to step 528.

Step 528 determines whether the user's most recent BMI parameter value is greater than or equal to 18, and less than 20. If so, step 528 proceeds to step 530 to determine that the user's nutritional status as "Thin", and generates a corresponding BMI activity recommendation (e.g. "You need to undertake moderate dietary intervention"). Otherwise, step 528 proceeds to step 532.

Step 532 determines whether the user's most recent BMI parameter value is greater than or equal to 16 and less than 18. If so, step 532 proceeds to step 534 to determine that the user's nutritional status as "Undernourished Grade 1", and generates a corresponding BMI activity recommendation (e.g. "You need to undertake significant dietary intervention under professional medical supervision"). Otherwise, step 532 proceeds to step 535 to generate the user's nutritional status as "Undernourished Grade 2", and generates a corresponding BMI activity recommendation (e.g. "You need to seek urgent professional medical help. You need to undertake significant dietary intervention under professional medical supervision").

Figure 18A:
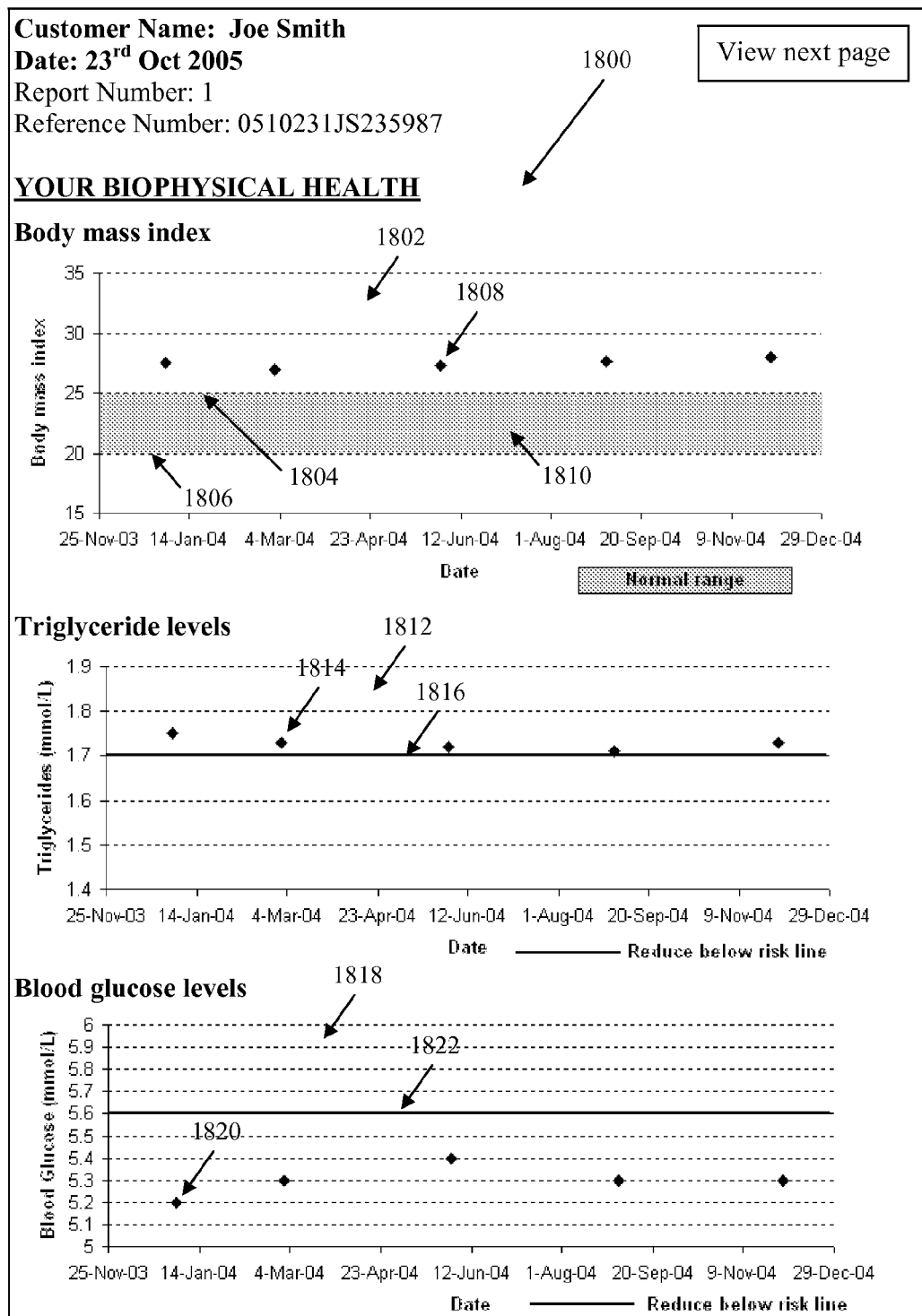
FIGS. 18A to 18E are screen displays of the output report displays, generated by the system.
Figure 18B:
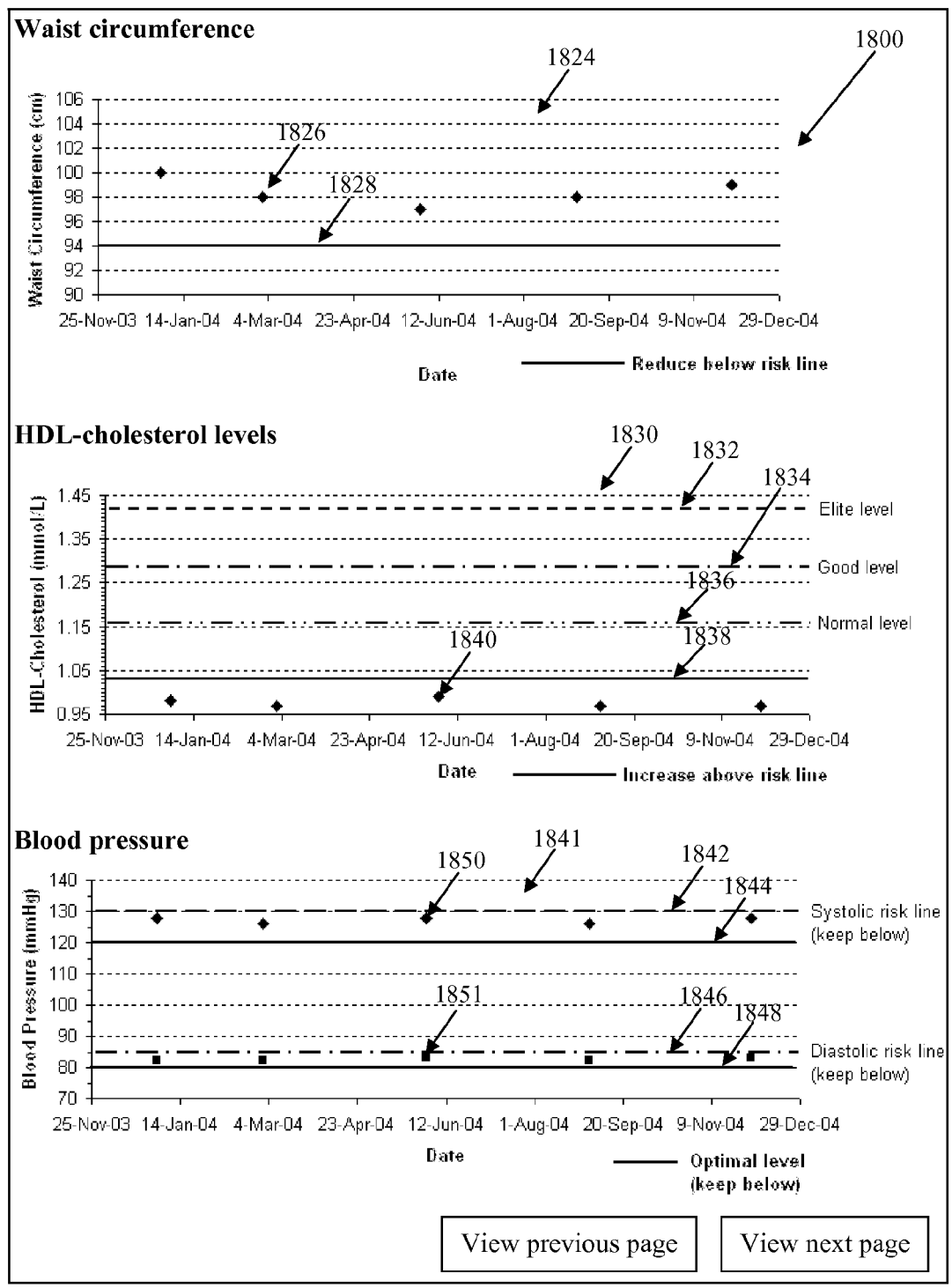
Figure 27:
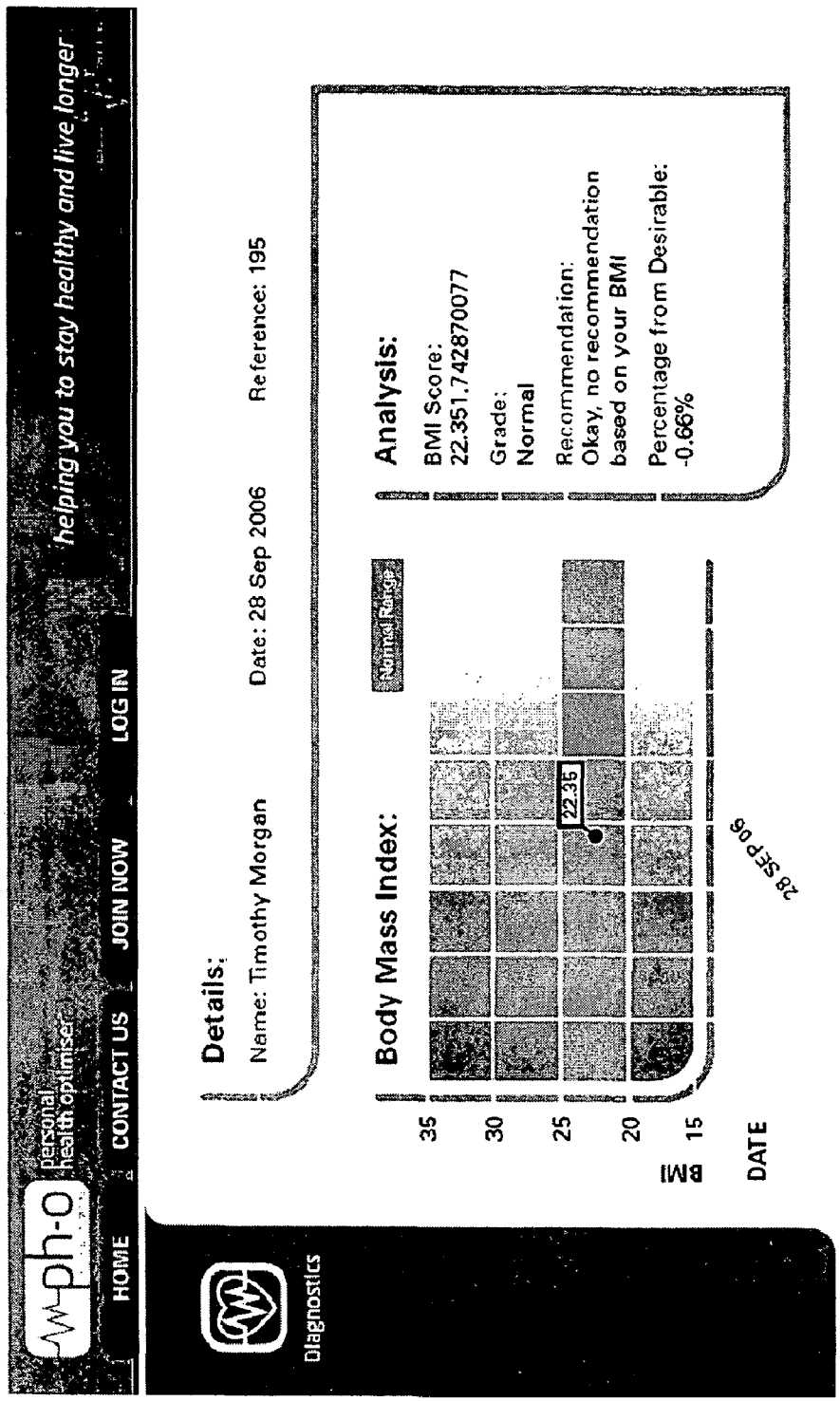

Steps 510, 514, 518, 522, 526, 530, 534 and 535 all proceed to step 536 to generate BMI graph data based on the user's BMI parameter values derived from the user's weight/height data in the database 110. The BMI graph data allows the client device 102 to generate a graphical representation of the changes in the user's BMI parameter values as recorded on different dates during the time period selected at step 402. An example of a BMI parameter graph is shown as item 1802 in FIG. 18A, which corresponds to a partial screen shot of the report 1800 generated for users by the client device 102 based on data generated by the analysis process 400. The BMI graph 1802 may include an upper boundary line 1804 and a lower boundary line 1806 representing the upper and lower limits of the range of BMI parameter values within which a person is determined as having normal nutritional status. The area between the upper and lower boundary lines 1804 and 1806 may be displayed in a colour different to the background colour of BMI parameter graph 1802. Each individual BMI data point 1808 is plotted against its particular date as shown in FIG. 18A. Another example of a BMI parameter graph and report interface is shown in FIG. 27. This also provides displays of information based on the BMI parameters and the recommendation generated.

Figure 18C:
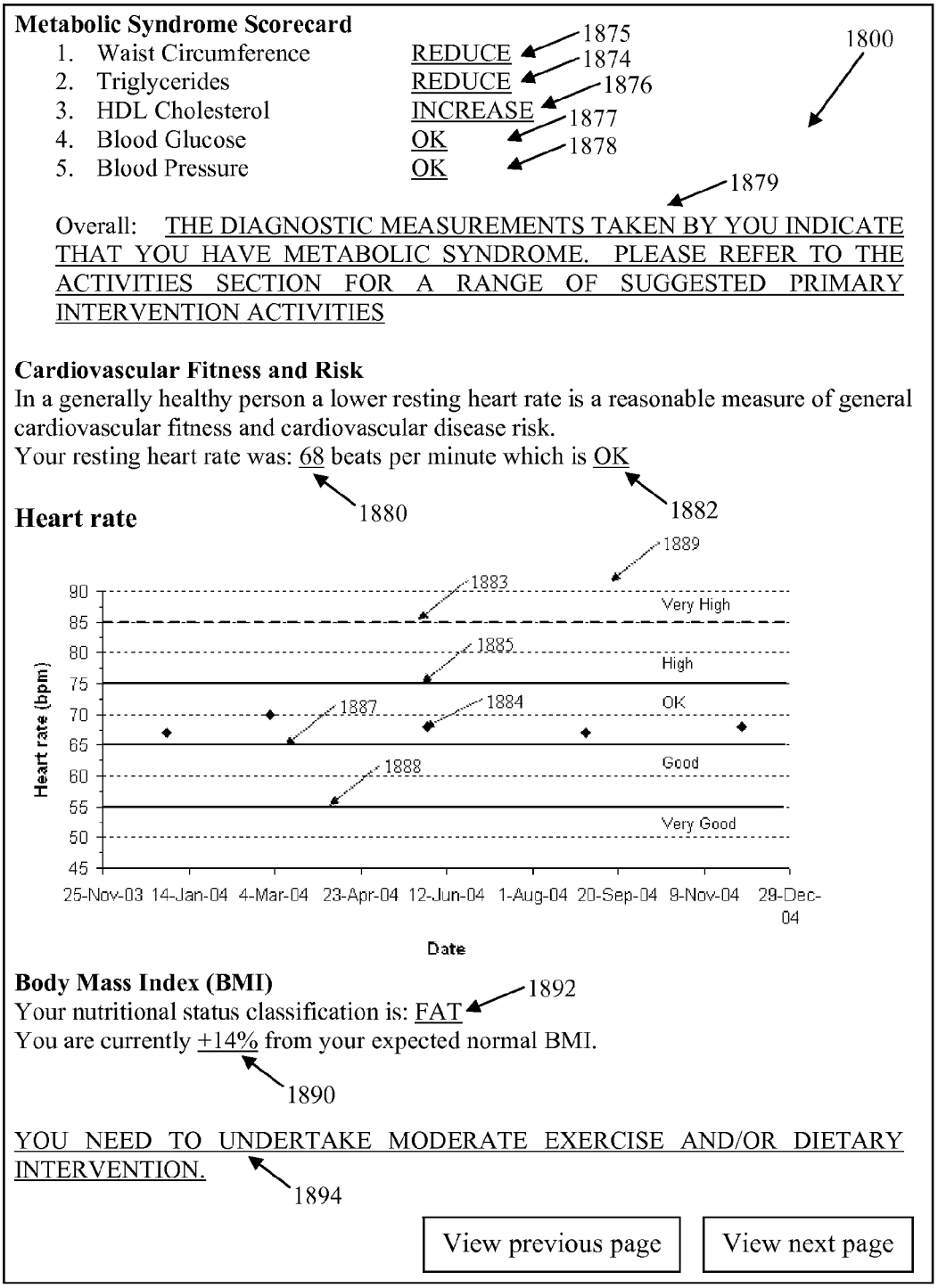

Step 538 generates, using Equation 2, a BMI change parameter representing the percentage change in the user's BMI parameter value in comparison with that user's desirable weight. The value of the BMI change parameter 1890 may be included in the report 1800, as shown in FIG. 18C.

$$\text{Change in } BMI\,(\%) = \left(\frac{BMI - 22.5}{22.5}\right) \times 100 \qquad \text{Equation 2}$$

Step 538 then proceeds to step 540, where execution returns to process 400.

Alternatively generation of the BMI parameters may be replaced with determination of a body fat percentage (BFP) parameter if the user answers yes to the following question: Are you a body builder or elite athlete with a very large muscle-mass body-type? Yes or No. If yes, the BMI may overstate a user's healthy weight, therefore BFP is an alternative measure of healthy weight, according to the findings reported by Dympna Gallagher et al. "*Healthy percentage*

*body fat ranges: an approach for developing guidelines based on body mass index.*", Am J Clin Nutr 2000; 72:694-701.

Figure 6:
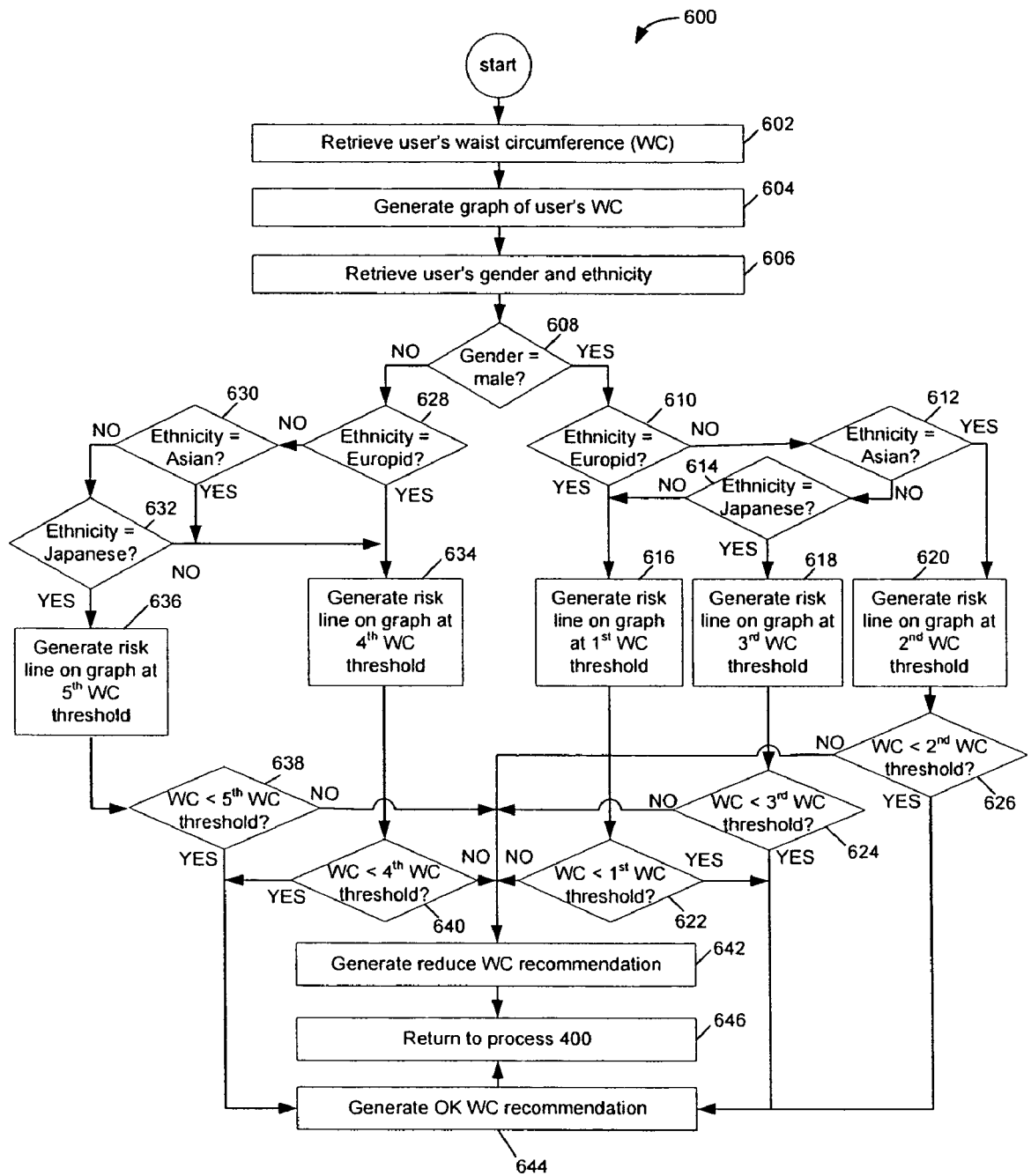

FIG. 6 is a flow diagram of the process 600 for generating recommendations based on the user's waist circumference (WC) parameter, and graphical representations of the changes in the value of the user's waist circumference parameter over the time period selected at step 402. Process 600 begins at step 602 by retrieving the user's WC parameter values from the database 110. Step 602 then proceeds to step 604 to generate WC graph data based on the user's WC parameter values. The WC graph data allows the client device 102 to generate a graphical representation (e.g. a graph) of the changes in the user's WC parameter values as recorded on different dates over the time period selected at step 402. An example of a WC parameter graph is shown as item 1824 in FIG. 18B, which may include data points 1826 representing the user's WC parameter values on different dates.

Step 604 proceeds to step 606 to retrieve the user's gender and ethnicity from the user's profile in the database 110. Step 608 then determines whether the user is male. If so, step 608 proceeds to step 610. Otherwise, step 608 proceeds to step 628.

Step 610 determines whether the user's ethnicity is Europid. If so, step 610 proceeds to step 616 to generate data for representing a risk line 1828 on the WC graph 1824 at a first WC parameter threshold value (e.g. at 94 cm or 34 inches), and then proceeds to step 622. Otherwise step 610 proceeds to step 612.

Step 612 determines whether the user's ethnicity is Asian. If so, step 612 proceeds to step 620 to generate data for representing a risk line 1828 on the WC graph 1824 at a second WC parameter threshold value (e.g. at 90 cm or 35.43 inches), and then proceeds to step 626. Otherwise step 612 proceeds to step 614.

Step 614 determines whether the user's ethnicity is Japanese. If so, step 614 proceeds to step 618 to generate data for representing a risk line 1828 on the WC graph 1824 at a third WC parameter threshold value (e.g. at 85 cm or 33.46 inches), and then proceeds to step 624. Otherwise step 614 proceeds to step 616 to generate data representing a risk line 1828 as described above.

If the user is female, step 608 proceeds to step 628 to determine whether the user's ethnicity is Europid. If so, step 628 proceeds to step 634 to generate data for representing a risk line 1828 on the WC graph 1824 at a fourth WC parameter threshold value (e.g. at 80 cm or 31.50 inches), and then proceeds to step 640. Otherwise step 628 proceeds to step 630.

Step 630 determines whether the user's ethnicity is Asian. If so, step 630 proceeds to step 634 to generate data representing a risk line 1828 as described above. Otherwise step 630 proceeds to step 632.

Step 632 determines whether the user's ethnicity is Japanese. If so, step 632 proceeds to step 636 to generate data for representing a risk line 1828 on the WC graph 1824 at a fifth WC parameter threshold value (e.g. at 90 cm or 35.43 inches), and then proceeds to step 638. Otherwise step 632 proceeds to step 634 to generate data representing a risk line 1828 as described above.

Step 622 determines whether the user's WC parameter value is less than the first WC parameter threshold value. If so, step 622 proceeds to step 644 to generate a WC recommendation indicating that the user's WC parameter value is "OK". Otherwise, step 622 proceeds to step 642 to generate a WC recommendation indicating that the user's WC parameter value needs to be reduced (e.g. "REDUCE") as depicted by 1875 in FIG. 18C.

Step 626 determines whether the user's WC parameter value is less than the second WC parameter threshold value. If so, step 626 proceeds to step 644 to generate a WC recommendation indicating that the user's WC parameter value is "OK". Otherwise, step 626 proceeds to step 642 to generate a WC recommendation indicating that the user's WC parameter value needs to be reduced (e.g. "REDUCE").

Step 624 determines whether the user's WC parameter value is less than the third WC parameter threshold value. If so, step 624 proceeds to step 644 to generate a WC recommendation indicating that the user's WC parameter value is "OK". Otherwise, step 624 proceeds to step 642 to generate a WC recommendation indicating that the user's WC parameter value needs to be reduced (e.g. "REDUCE").

Step 640 determines whether the user's WC parameter value is less than the fourth WC parameter threshold value. If so, step 640 proceeds to step 644 to generate a WC recommendation indicating that the user's WC parameter value is "OK". Otherwise, step 640 proceeds to step 642 to generate a WC recommendation indicating that the user's WC parameter value needs to be reduced (e.g. "REDUCE").

Step 638 determines whether the user's WC parameter value is less the fifth WC parameter threshold value. If so, step 638 proceeds to step 644 to generate a WC recommendation indicating that the user's WC parameter value is "OK". Otherwise, step 638 proceeds to step 642 to generate a WC recommendation indicating that the user's WC parameter value needs to be reduced (e.g. "REDUCE").

Steps 642 and 644 both proceed to step 646, where execution returns to process 400.

Figure 7:
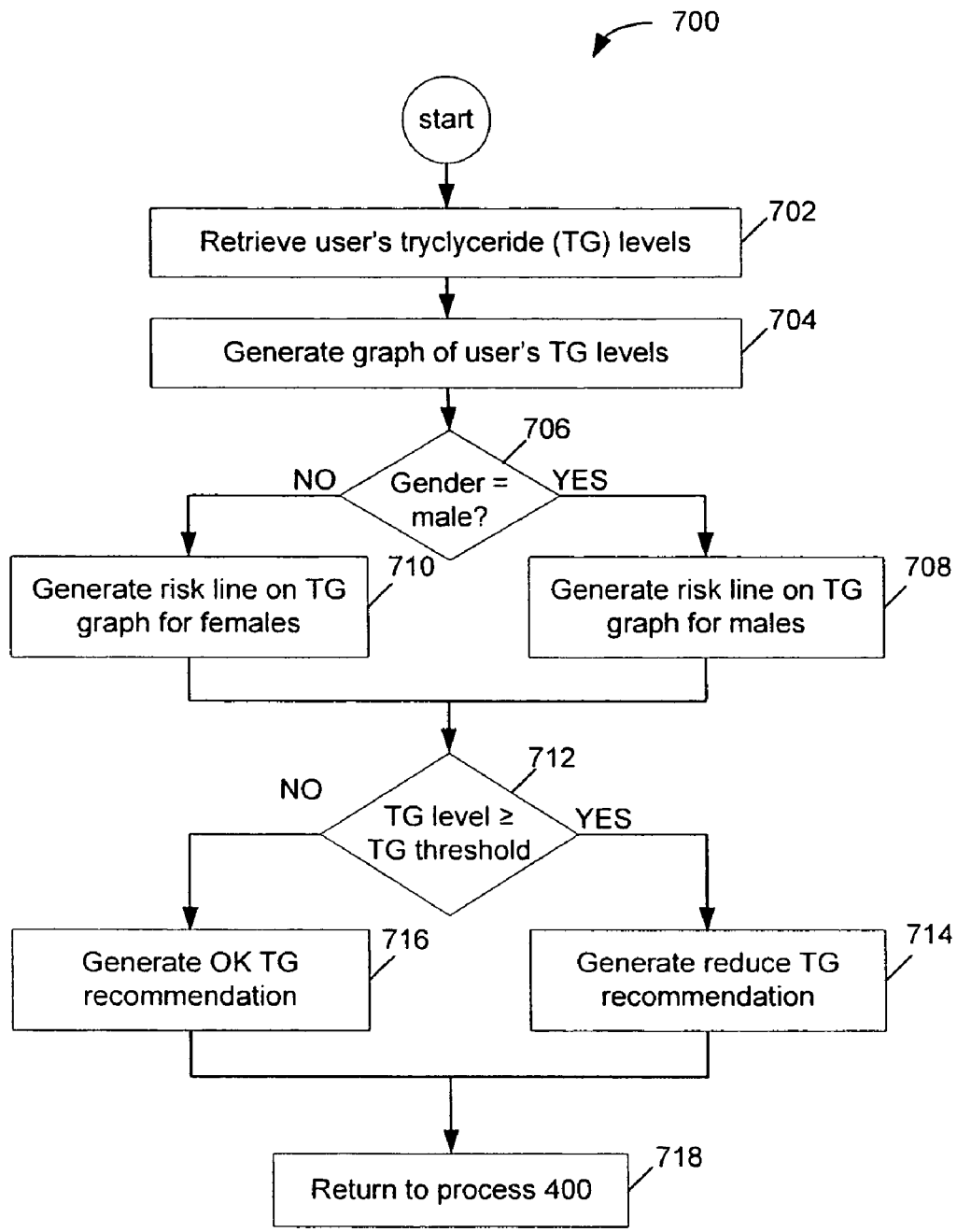

FIG. 7 is a flow diagram of the process 700 for generating recommendations based on the user's triglyceride (TG) parameter, and graphical representations of the changes in the value of the user's triglyceride parameters over the time period selected at step 402. Process 700 begins at step 702 by retrieving the user's TG parameter values from the database 110. Step 702 then proceeds to step 704 to generate TG graph data based on the user's TG parameter values. The TG graph data allows the client device 102 to generate a graphical representation (e.g. a graph) of the changes in the user's TG parameter values as recorded on different dates over the time period selected at step 402. An example of a TG parameter graph is shown as item 1812 in FIG. 18A, which may include data points 1814 representing the user's TG parameter values on different dates.

Step 704 proceeds to step 706 to retrieve the user's gender from the user's profile in the database 110 and determine whether the user is male. If so, step 706 proceeds to step 708. Otherwise, step 706 proceeds to step 710.

Step 708 generates data for representing a risk line 1816 on the TG graph 1812 at the TG parameter threshold value for males (e.g. at 1.7 mmol/L), and then proceeds to step 712. Step 710 generates data for representing a risk line 1816 on the TG graph 1812 at the TG parameter threshold value for females (e.g. at 1.7 mmol/L), and then proceeds to step 712.

Step 712 determines whether the user's most recent TG parameter value is greater than or equal to the TG parameter value threshold (e.g. 1.7 mmol/L). If so, step 712 proceeds to step 714 to generate a TG recommendation indicating that the user's TG parameter value needs to be reduced (e.g. "REDUCE") as depicted by 1874 in FIG. 18C. Otherwise, step 712 proceeds to step 716 to generate a TG recommendation indicating that the user's TG parameter value is acceptable (e.g. "OK"). Steps 714 and 716 both proceed to step 718, where execution returns to process 400.

Figure 8:
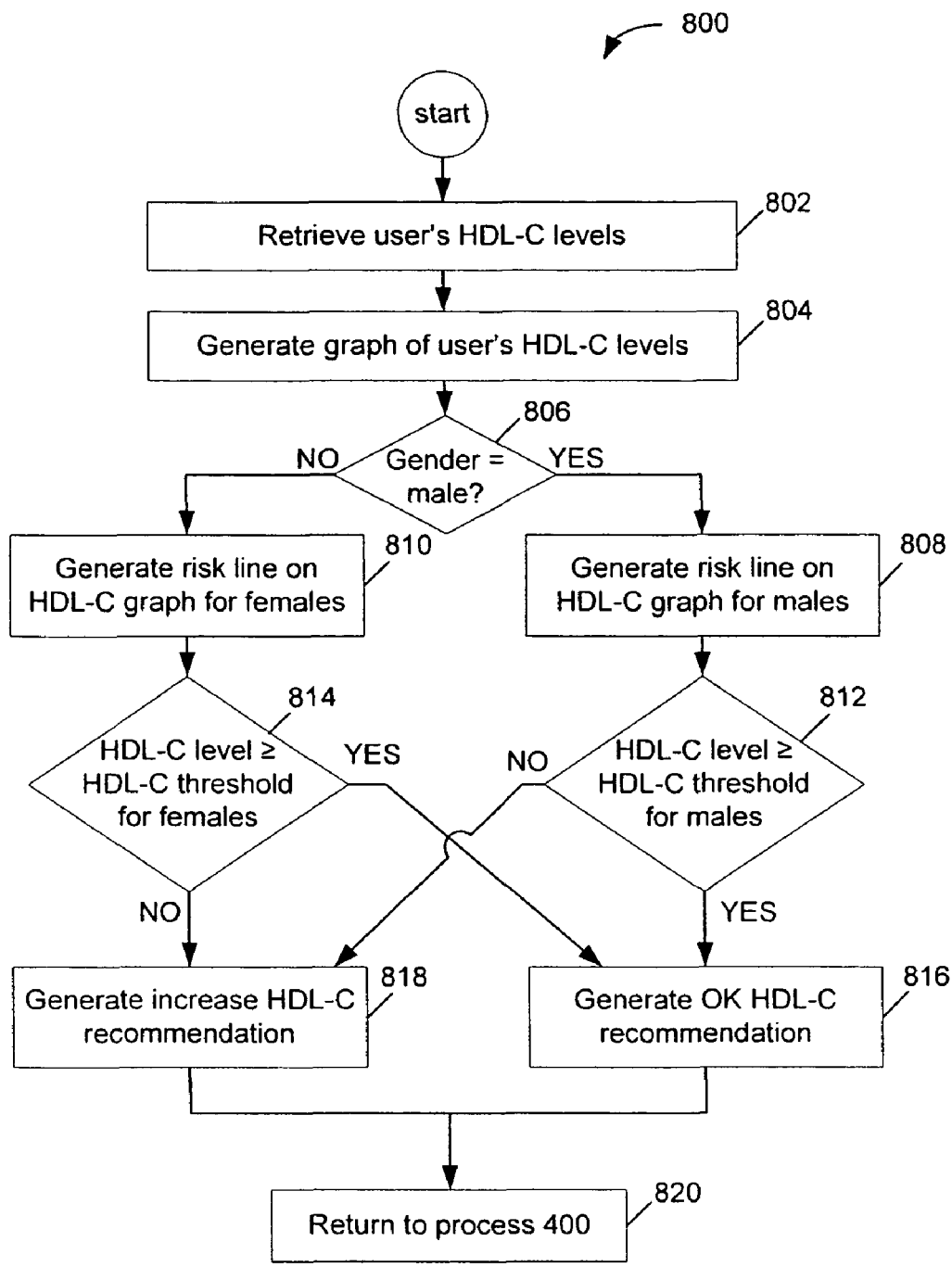

FIG. 8 is a flow diagram of the process 800 for generating recommendations based on the user's HDL cholesterol (HDL-C) parameter, and graphical representations of the changes in the value of the user's HDL cholesterol parameters over the time period selected at step 402. Process 800 begins at step 802 by retrieving the user's HDL-C parameter values from the database 110. Step 802 then proceeds to step 804 to generate HDL-C graph data based on the user's HDL-C parameter values. The HDL-C graph data allows the client device 102 to generate a graphical representation (e.g. a graph) of the changes in the value of the user's HDL-C parameter values as recorded on different dates over the time period selected at step 402. An example of a HDL-C parameter graph is shown as item 1830 in FIG. 18B, which may include data points 1840 representing the user's HDL-C parameter values on different dates, and lines 1832, 1834 and 1836 representing approximate population-based thresholds for normal HDL-C levels (e.g. males at 1.16 mmol/L (45 mg/dL); females at 1.42 mmol/L (55 mg/dL)), good HDL-C levels (e.g. males at 1.29 mmol/L (50 mg/dL); females at 1.55 mmol/L (60 mg/dL)) and elite/optimum HDL-C levels (e.g. males at 1.42 mmol/L (55 mg/dL); females at 1.68 mmol/L (65 mg/dL)), as discussed in Deshaies Y., Allard C., *Serum high-density lipoprotein cholesterol in male and female Olympic athletes*, Med. Sci. Sports Exer., 1982, 14(3), pp. 207-211.

Step 804 proceeds to step 806 to retrieve the user's gender from the user's profile in the database 110 and determine whether the user is male. If so, step 806 proceeds to step 808. Otherwise, step 806 proceeds to step 810.

Step 808 generates data for representing a risk line 1838 on the HDL-C graph 1830 at the HDL-C parameter value threshold for males (e.g. at 1.03 mmol/L), and then proceeds to step 812. Step 810 generates data for representing a risk line 1838 on the HDL-C graph 1830 at the HDL-C parameter value threshold for females (e.g. at 1.29 mmol/L), and then proceeds to step 814.

Step 812 determines whether the user's HDL-C parameter value is greater than or equal to the HDL-C parameter value threshold for males. If so, step 812 proceeds to step 816 to generate a HDL-C recommendation indicating that the user's HDL-C parameter value is acceptable (e.g. "OK"). Otherwise, step 812 proceeds to step 818 to generate a HDL-C recommendation indicating that the user's HDL-C parameter value needs to be increased (e.g. "INCREASE") as depicted by 1876 in FIG. 18C.

Step 814 determines whether the user's HDL-C parameter value is greater than or equal to the HDL-C parameter value threshold for females. If so, step 814 proceeds to step 816 to generate a HDL-C recommendation indicating that the user's HDL-C parameter value is acceptable (e.g. "OK"). Otherwise, step 814 proceeds to step 818 to generate a HDL-C recommendation indicating that the user's HDL-C parameter value needs to be increased (e.g. "INCREASE"). Steps 816 and 818 both proceed to step 820, where execution returns to process 400.

Figure 9:
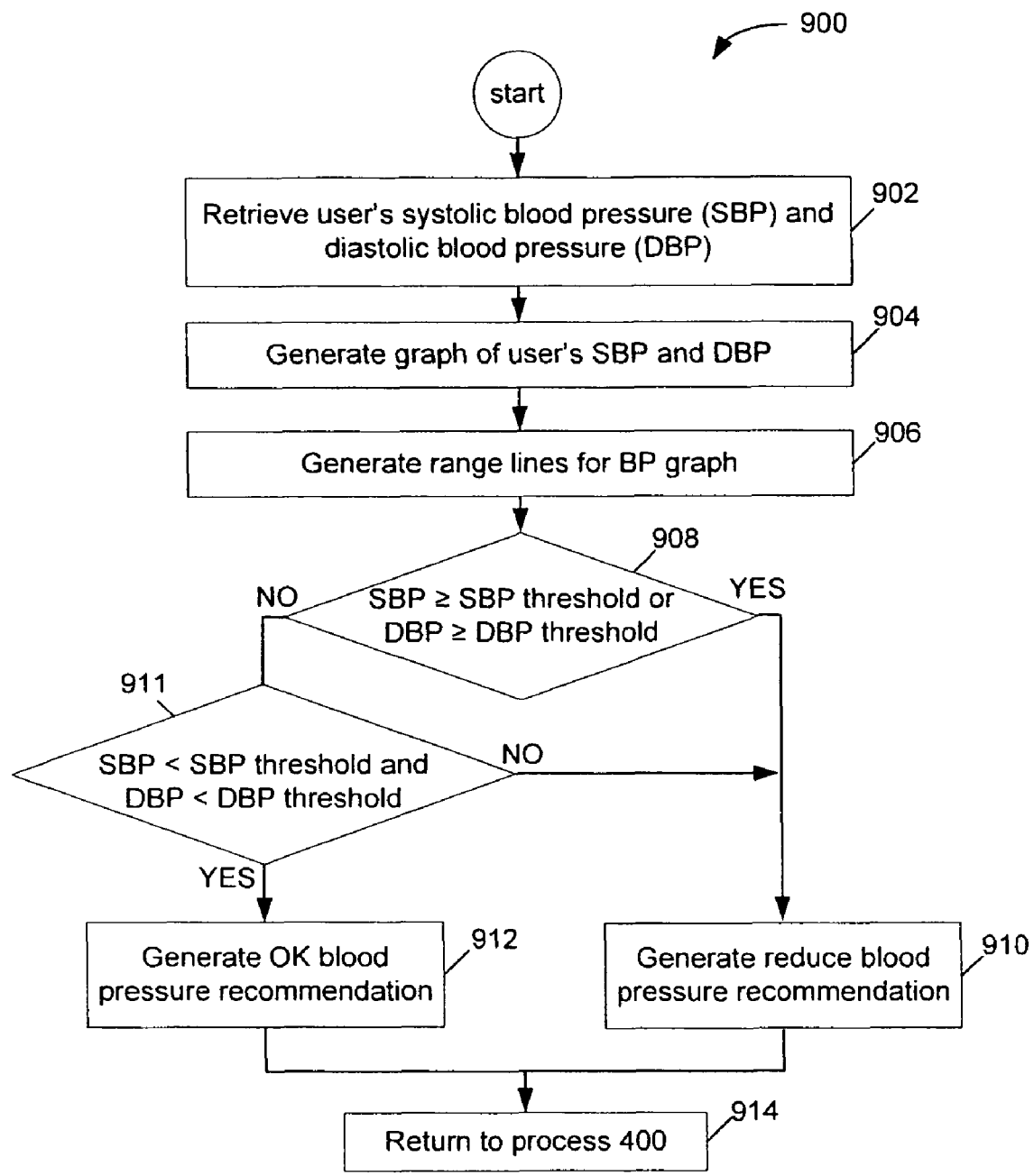

FIG. 9 is a flow diagram of the process 900 for generating recommendations based on the user's blood pressure (BP) parameters, and graphical representations of the changes in the user's blood pressure parameters over the time period selected at step 402. A user's BP parameters include a SBP parameter value and a DBP parameter value, which represent the user's systolic blood pressure and diastolic blood pressure readings, respectively. Process 900 begins at step 902 by retrieving the user's BP parameter values from the database 110. Step 902 then proceeds to step 904 to generate BP graph data based on the user's BP parameter values. The BP graph data allows the client device 102 to generate a graphical representation (e.g. a graph) of the changes in the value of the user's BP parameter values as recorded on different dates over the time period selected at step 402. An example of a BP parameter graph is shown as item 1841 in FIG. 18B, which may include data points 1850 and 1851 representing the user's SBP and DBP parameter values on different dates, respectively.

Step 904 proceeds to step 906 to generate data for representing the SBP threshold line 1842 (e.g. at 130 mmHg) and the optimal SBP level line 1844 (e.g. at 120 mmHg) on the BP parameter graph for indicating, respectively, the risk level and optimum systolic blood pressure level below which the user's systolic blood pressure will be regarded as acceptable (i.e. "OK"). These risk level and optimum systolic blood pressure values are respectively consistent with normal adult blood pressure level (being a SBP <130 mmHg and a DBP <85 mmHg); and the optimal adult blood pressure (being a SBP <120 mmHg and a DBP <80 mmHg) as discussed in *The Merck Manual*, 17$^{th}$ Edition, p. 1633, Table 199-2 Classification of blood pressure for adults; Merck 1999, NJ.

Step 906 also generates data for representing the DBP threshold line 1846 (e.g. at 85 mmHg) and the optimal DBP level line 1848 (e.g. at 80 mmHg) on the BP parameter graph for indicating, respectively, the risk level and optimum blood pressure level within which the user's diastolic blood pressure will be regarded as acceptable (i.e. "OK").

Step 906 proceeds to step 908 to determine whether the user's SBP parameter value is greater than or equal to the SBP parameter threshold value (e.g. at 130 mmHg), or whether the user's DBP parameter value is greater than or equal to the DBP parameter threshold value (e.g. at 85 mmHg). If so, step 908 proceeds to step 910 to generate a BP recommendation indicating that the user's BP parameter value needs to be reduced (i.e. "REDUCE"). Otherwise, step 908 proceeds to step 911 to determine whether the user's SBP parameter value is less than the SBP parameter threshold value, and whether the user's DBP parameter value is less than the DBP parameter threshold. If so, step 911 proceeds to step 912 to generate a BP recommendation indicating that the user's BP parameter value is acceptable (e.g. "OK"), as depicted by 1878 in FIG. 18C. Otherwise, step 911 proceeds to step 914. Steps 910 and 912 both proceed to step 914, where execution returns to process 400.

Figure 10:
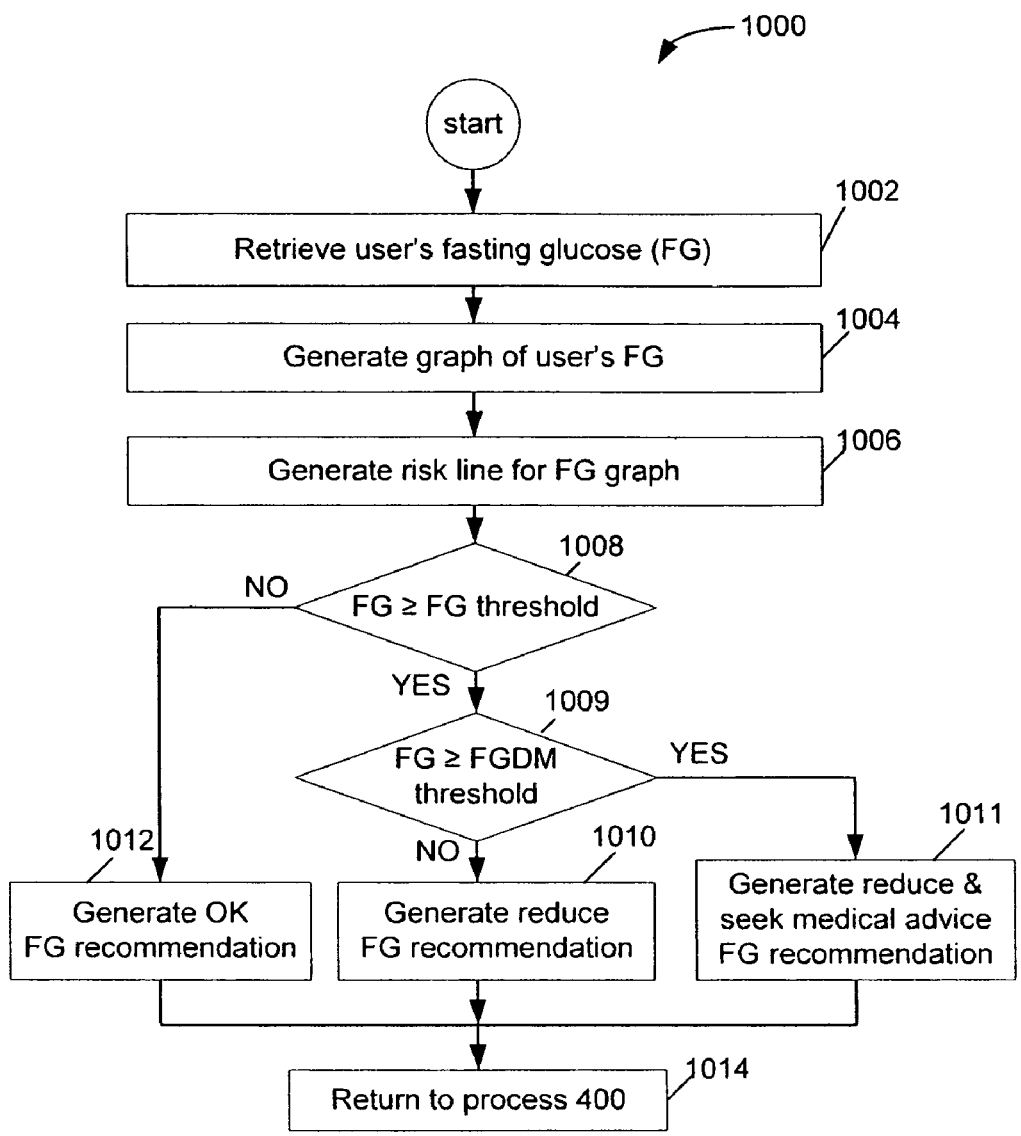

FIG. 10 is a flow diagram of the process 1000 for generating recommendations based on the user's fasting glucose (or blood glucose) (FG) parameter, and graphical representations of the changes in the value of the user's fasting glucose parameters over the time period selected at step 402. Process 1000 begins at step 1002 by retrieving the user's FG parameter values from the database 110. Step 1002 then proceeds to step 1004 to generate FG graph data based on the user's FG parameter values. The FG graph data allows the client device 102 to generate a graphical representation (e.g. a graph) of the changes in the value of the user's FG parameter values as recorded on different dates over the time period selected at step 402. An example of a FG parameter graph is shown as item 1818 in FIG. 18A, which may include data points 1820 representing the user's FG parameter values on different dates.

Step 1004 proceeds to step 1006 to generate data for representing a risk line 1822 on the FG graph 1818 at the FG parameter value threshold (e.g. at 5.6 mmol/L), and then proceeds to step 1008.

Step 1006 proceeds to step 1008 to determine whether the user's FG parameter value is greater than or equal to the FG parameter threshold value (e.g. at 5.6 mmol/L or 100 mg/dL). If so, step 1008 proceeds to step 1009 to determine if the user's FG parameter value is greater than or equal to the fasting glucose diabetes mellitus (FGDM) threshold value (e.g. at 7.77 mmol/L or 140 mg/dL). Otherwise, step 1008 proceeds to step 1012 to generate a FG recommendation indicating that the user's FG parameter value is acceptable (e.g. "OK"), as depicted by 1877 in FIG. 18C.

If step 1009 determines that user's fasting plasma glucose level is greater than or equal to the FGDM threshold value then the user may have type II diabetes mellitus (as discussed in *The Merck Manual*, 17th Edition, 1999, Merck and Co. Inc. p. 170) and step 1009 proceeds to step 1011 to generate a FG recommendation to reduce the user's FG parameter value (e.g. "REDUCE") that includes a recommendation to seek professional medical advice from a general physician (e.g. "Seek professional medical help"). Otherwise, step 1009 proceeds to step 1010 to generate a FG recommendation indicating that the user's FG parameter value needs to be reduced (e.g. "REDUCE"). Steps 1010, 1011 and 1012 proceed to step 1014, where execution returns to process 400.

Figure 11:
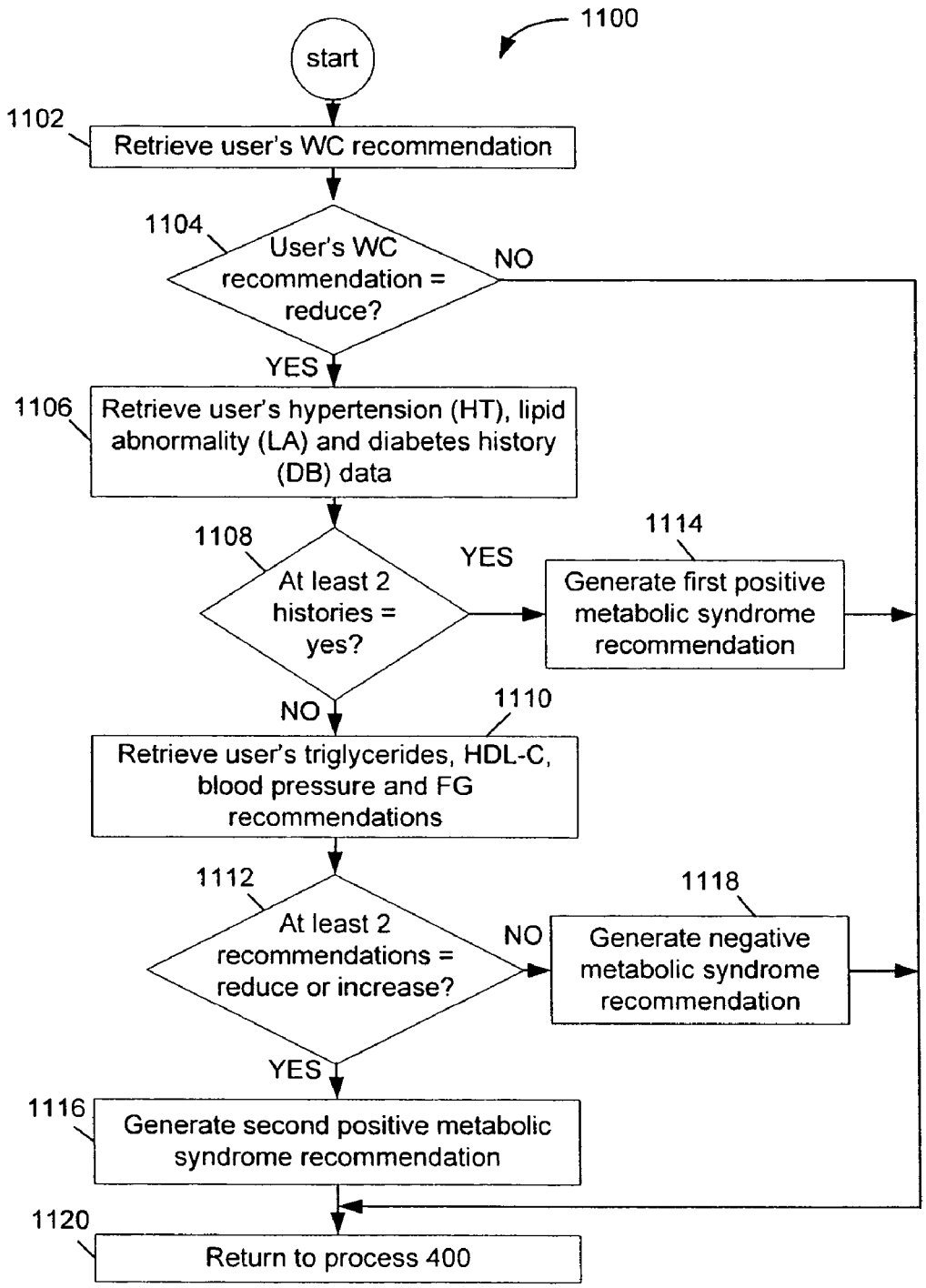

FIG. 11 is a flow diagram of the process 1100 for analysing the user's body-related parameters for determining whether the user has metabolic syndrome. A range of recommendations would be provided to the individual customer based upon the following logic for the deductive procedure.

Recently, the International Diabetes Federation (IDF) has provided a global consensus statement on the definition of the metabolic syndrome along with recommendations for primary and secondary intervention (as described in *The IDF consensus worldwide definition of the metabolic syndrome*, April 2005 (available from <http://www.idf.org>); and Zimmet P Z, Alberti K G M M, Shaw J E, *Mainstreaming the metabolic syndrome: a definitive definition*, MJA, 2005, 183 (4), pp. 175-76). According to the International Diabetes Federation definition, a person must have the following to be defined as having metabolic syndrome:

i) Central obesity (defined as waist circumference $\geq$94 cm for Europid men and $\geq$80 cm for Europid women, with ethnicity specific values for other groups—for example, South Asian and South-East Asian men $\geq$90 cm, women $\geq$80 cm; and Japanese men $\geq$85 cm, women $\geq$90 cm)

plus at least two of the following four factors:

ii) Raised serum triglyceride level ($\geq$1.7 mmol/L or $\geq$150 mg/dL)

iii) Reduced serum HDL-cholesterol level (<1.03 mmol/L or <40 mg/dL in males and <1.29 mmol/L or <50 mg/dL in females), (or specific treatment for these lipid abnormalities)

iv) Raised blood pressure (systolic blood pressure $\geq$130 mm/Hg or diastolic blood pressure $\geq$85 mmHg), or treatment of previously diagnosed hypertension v) Impaired fasting glycemia (fasting plasma glucose [FPG]$\geq$ 5.6 mmol/L or $\geq$100 mg/dL), or previously diagnosed type 2 diabetes If the user's body-related parameters meet the criteria for metabolic syndrome, then the recommendation would be to seek professional medical help (e.g. general physician). A dietician and exercise instructor would also be suggested for those individual's with the socio-economic capacity (i.e. annual household income in the upper 40th percentile e.g. $\geq$US$40,000 or approximately $\geq$AU$53,000) and a body mass index greater than or equal to 30.

If the user's body-related parameters only meet one of the factors for metabolic syndrome, then the following recommendations would be given:

i) For users having the central obesity risk factor (as defined above) both dietary and exercise primary intervention activities is recommended.

ii) For users having the raised serum triglyceride level (as defined above) both dietary and exercise primary intervention activities is recommended, with particular advice to ensure the level of dietary fat, particularly saturated fat, was appropriate.

iii) For users having either reduced serum HDL-cholesterol or raised blood pressure (as defined above) both dietary and exercise primary intervention activities is recommended, with particular advice to ensure an appropriate level of aerobic exercise to build cardiovascular fitness.

iv) For users having impaired fasting glycemia (as defined above), then both dietary and exercise primary intervention activities would be recommended, with particular advice to ensure the level of dietary complex sugars was appropriate, whilst minimizing simple sugars in the diet.

Process 1100 begins at step 1102 by retrieving the user's most recent WC recommendation from the database 110. Step 1102 proceeds to step 1104 to determine whether the user's WC recommendation indicates that the user's WC needs to be reduced (i.e. if the user's WC recommendation is "REDUCE"). If not, step 1104 proceeds to step 1120. Otherwise, step 1104 proceeds to step 1106.

Step 1106 retrieves the user's hypertension (HT) history data, lipid abnormality (LA) history data and diabetes (DB) history data from the user profile in the database 110. Step 1106 proceeds to step 1108 to determine whether the HT, LA and DB history data indicates that the user has at least two of these conditions (i.e. that at least 2 of these histories equals "YES"). If so, step 1108 proceeds to step 1114 to generate a first positive metabolic syndrome recommendation (e.g. "Your waist measurement and medical history indicate that you have metabolic syndrome. Please refer to the activities section for a range of suggested primary intervention activities"). Otherwise, step 1108 proceeds to step 1110.

Step 1110 retrieves the user's most recent triglyceride (TG) recommendation, HDL-cholesterol (HDL-C) recommendation, blood pressure recommendation, and the fasting glucose (FG) recommendation from the database 110. Step 1110 proceeds to step 1112 to determine whether at least 2 of the retrieved recommendations indicates a need to reduce the corresponding parameter value. If so, step 1112 proceeds to step 1116 to generate a second positive metabolic syndrome recommendation (e.g. "The diagnostic measurements taken by you indicate that you have metabolic syndrome. Please refer to the activities section for a range of suggested primary intervention activities"), as depicted by 1879 in FIG. 18C. Otherwise, step 1112 proceeds to step 1118 to generate a negative metabolic syndrome recommendation (e.g. "OK. The diagnostic measurements taken by you indicate that you do not have metabolic syndrome"). Steps 1114, 1116 and 1118 all proceed to 1120, where execution returns to process 400.

Figure 12:
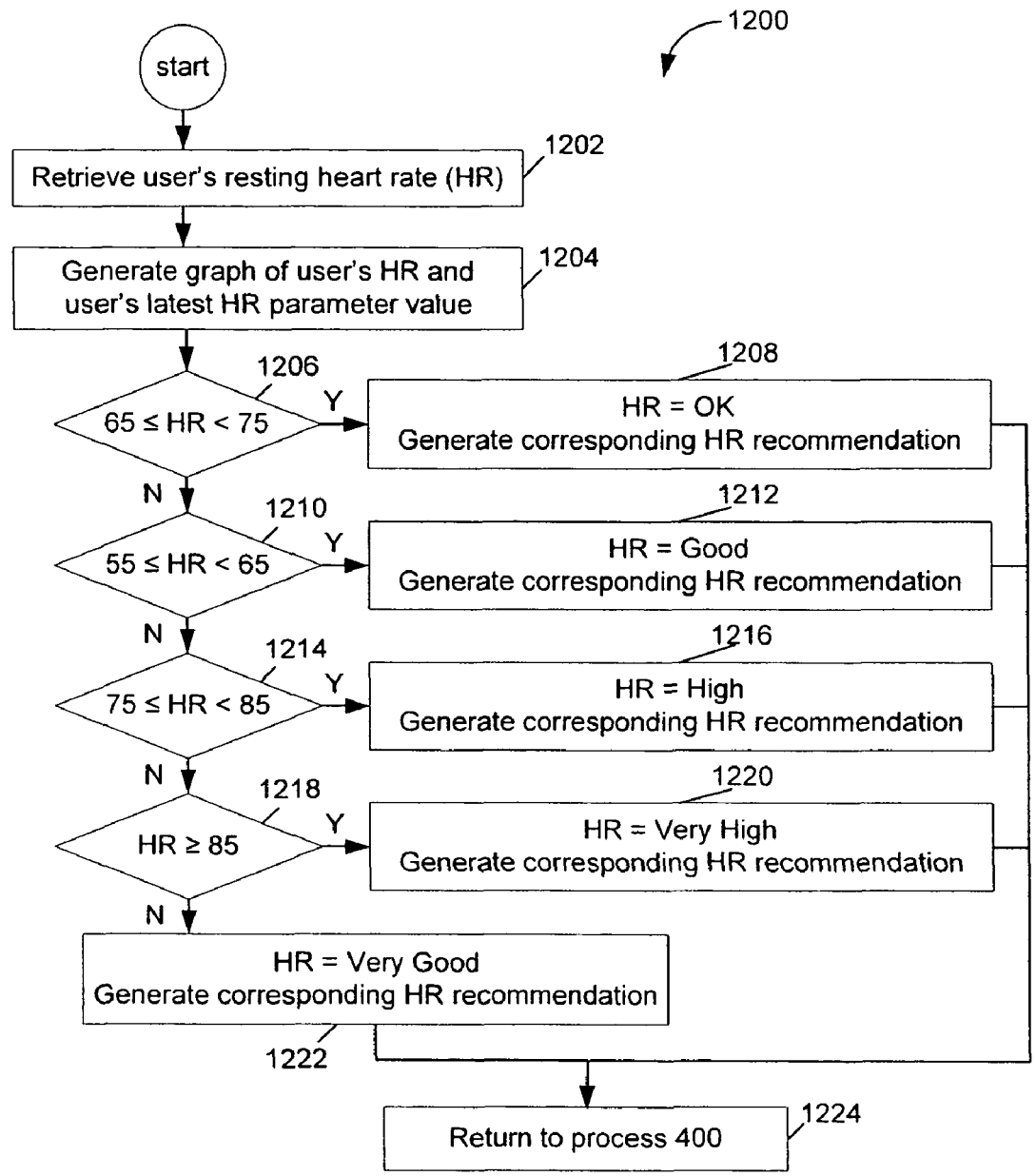

FIG. 12 is a flow diagram of the process 1200 for generating recommendations based on the user's resting heart rate (HR) parameter, and graphical representations of the changes in the value of the user's resting heart rate parameter over the time period selected at step 402. Process 1200 begins at step 1202 by retrieving the user's HR parameter values from the database 110. Step 1202 then proceeds to step 1204 to generate HR graph data based on the user's HR parameter values. The HR graph data allows the client device 102 to generate a graphical representation (e.g. a graph) of the changes in the value of the user's HR parameter values as recorded on different dates over the time period selected at step 402. An example of a HR parameter graph is shown as item 1889 in FIG. 18C, which corresponds to a partial screen shot of the report 1800 generated for users by the client device 102 based on data generated by the analysis process 400.

The HR parameter graph 1889 may include a very high HR lower boundary line 1883, a moderately high HR lower boundary line 1885, an OK (or general average) HR lower boundary line 1887 and a good HR lower boundary line 1888. These lines 1883, 1885, 1887 and 1888 represent the upper and/or lower limits of different ranges of HR parameter values corresponding to different levels of cardiovascular fitness/cardiovascular disease risk, such that the lower the HR range the higher the cardiovascular fitness and the lower the cardiovascular disease risk (as discussed in Ferrieres J., Ruidavets J. B. *Association between resting heart rate and hypertension treatment in a general population*, Am. J. Hypetens., 1999, 12(6), pp. 628-31; Cheng Y. J. et al., *Heart rate reserve as a predictor of cardiovascular all-cause mortality in men*, Med. Sci. Sports Exerc., 2002, 34(12), pp. 1873-8; and Cooper K. H. et al., *Physical fitness levels vs selected coronary risk factors. A cross-sectional study*, JAMA, 1976, 236(2), pp. 166-169). The ranges corresponding to different risk levels on the HR parameter graph 1889 may optionally be displayed in a colour different to the background colour of HR parameter graph 1883. Each individual HR data point 1884 is plotted against its particular date as shown in FIG. 18C for the selected time frame. Step 1204 also displays the user's latest HR parameter value corresponding to different dates (e.g. as depicted by 1880 in FIG. 18C).

Step 1204 proceeds to step 1206 to determine whether the user's most recent HR parameter value is greater than or equal to 65 beats per minute (bpm), and less than 75 bpm. If so, step 1206 proceeds to step 1208 to generate a HR recommendation indicating the user's HR parameter value is "OK" as depicted by 1882 in FIG. 18C, and then proceeds to step 1224. Otherwise, step 1206 then proceeds to step 1210.

Step 1210 determines whether the user's most recent HR parameter value is greater than or equal to 55 bpm, and less than 65 bpm. If so, step 1210 proceeds to step 1212 to generate a HR recommendation indicating that the user's HR parameter value is "Good", and then proceeds to step 1224. Otherwise, step 1210 proceeds to step 1214.

Step 1214 determines whether the user's most recent HR parameter value is greater than or equal to 75 bpm, and less than 85 bpm. If so, step 1214 proceeds to step 1216 to generate a HR recommendation indicating that the user's HR parameter value is "High", and then proceeds to step 1224. Otherwise, step 1214 proceeds to step 1218.

Step 1218 determines whether the user's most recent HR parameter value is greater than 85 bpm. If so, step 1218 proceeds to step 1220 to generate a HR recommendation indicating that the user's HR parameter value is "Very High", and then proceeds to step 1224. Otherwise, step 1218 proceeds to step 1222 to generate a HR recommendation indicating that the user's HR parameter value is "Very Good" (i.e. <65 bpm), and then proceeds to step 1224. At step 1224, execution returns to process 400.

Figure 13A:
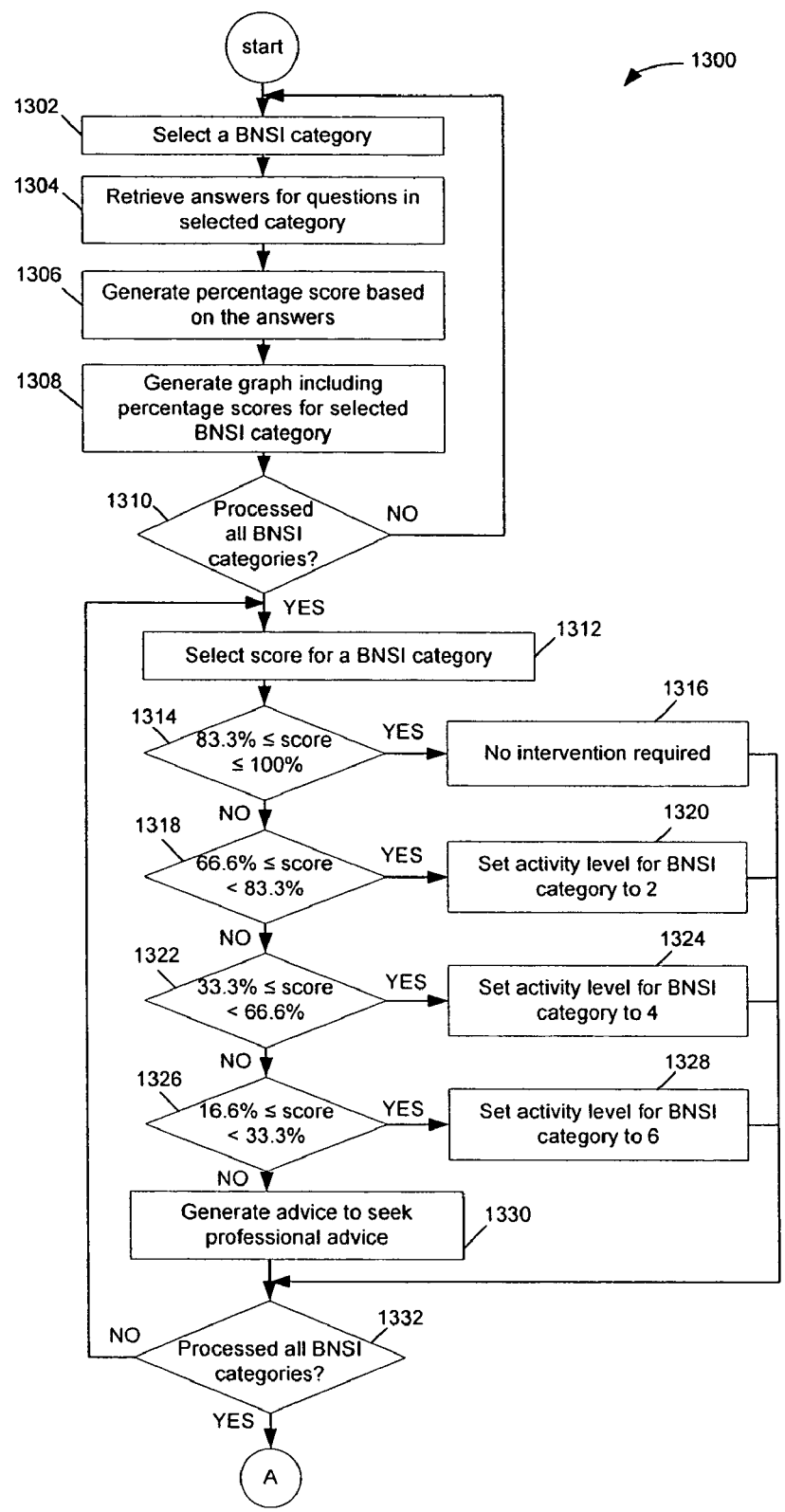
Figure 13B:
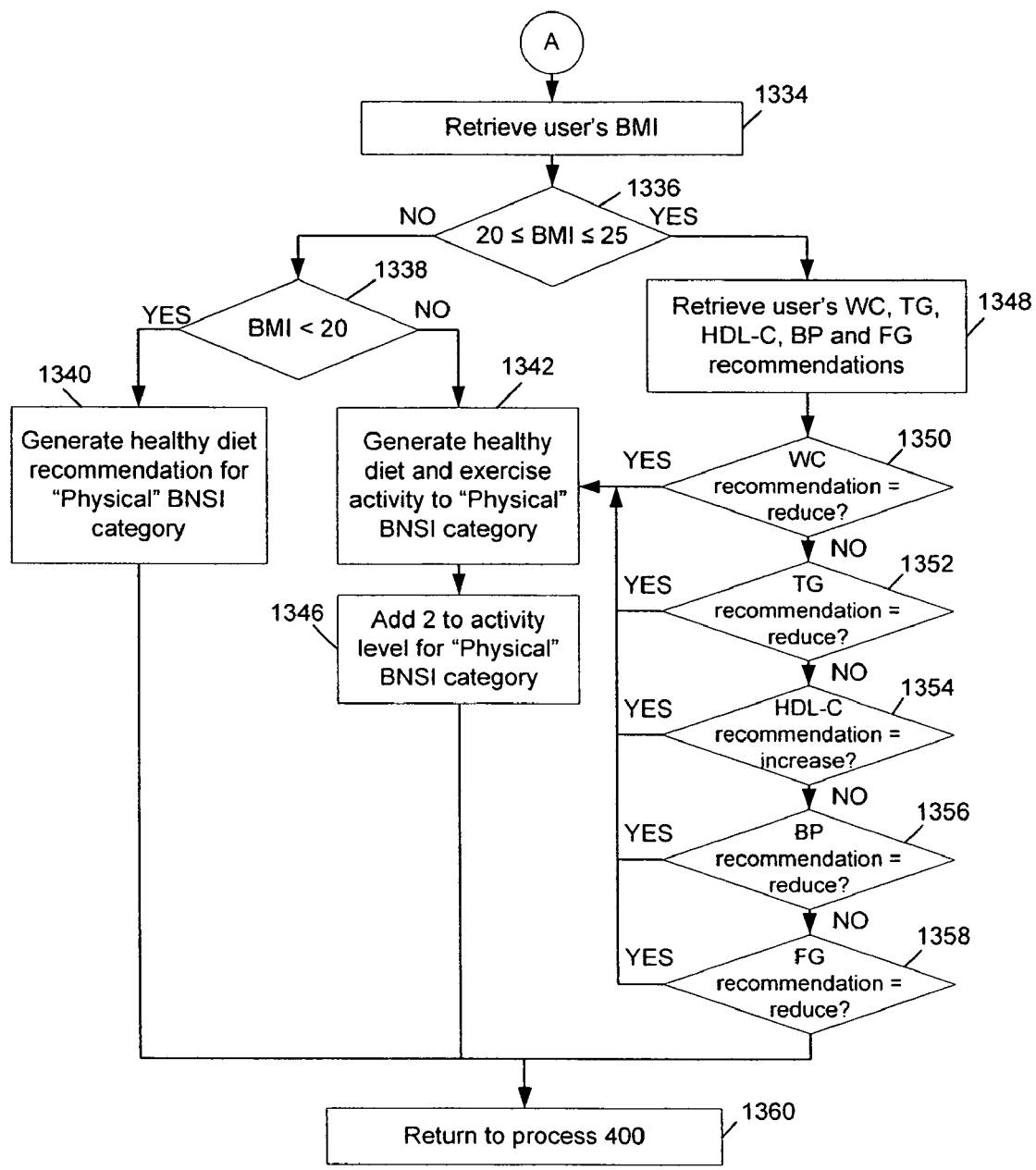

FIGS. 13A and 13B is a flow diagram of the process 1300 for generating recommendations based on the user's responses to the modified BNSI survey. The customer's basic needs (i.e. self-actualization, self-esteem—love/belonging, self-esteem—individuality, safety/security and physical) are measured over time to allow specific activity recommendations to be made. Ongoing measurement also has the benefit of determining whether or not the rank order of their basic needs changes in terms of their order of importance as the customer ages (as discussed in Majercsik E., *Hierarchy of Needs of Geriatric Patients*, Gerontology, 2005, 51(3), pp. 170-73) which is automatically updated by the system to reflect these changes.

Process 1300 begins at step 1302 by selecting one of the BNSI categories (e.g. self-actualization needs) for processing. Step 1304 retrieves the answers provided by the user for the selected category. For example, each category may have three questions, and step 1304 retrieves the response for each of those questions.

The score for the modified BNSI is converted to a percentage score by normalizing the seven-point scale on the basis that a middle score of 4 (Mixed) is equivalent to a percentage score of 50%, score of 1 (Terrible) equivalent to 0% and a score of 7 (Delighted) equivalent to 100% for each sub-grouping used. Step 1306 generates the category score parameter (as a percentage value) for the category needs area by summing the actual scores for the questions in the selected category using Equation 3 [Factor 16.6?]:

$$\text{Category score (\%)} = \left[\frac{(Q_1 + Q_2 + \ldots + Q_n) - n}{n}\right] \times 16.6 \qquad \text{Equation 3}$$

where $Q_1$ to $Q_n$ each represents the respective actual score values (ranging from 1 to 7 for the modified BNSI survey) corresponding to the $1^{st}$ to the nth question in the selected category, n represents the total number of questions in the category. The category score parameter is then stored in the database 110 in association with the date on which the modified BNSI scores were received and the corresponding user profile.

Figure 29:
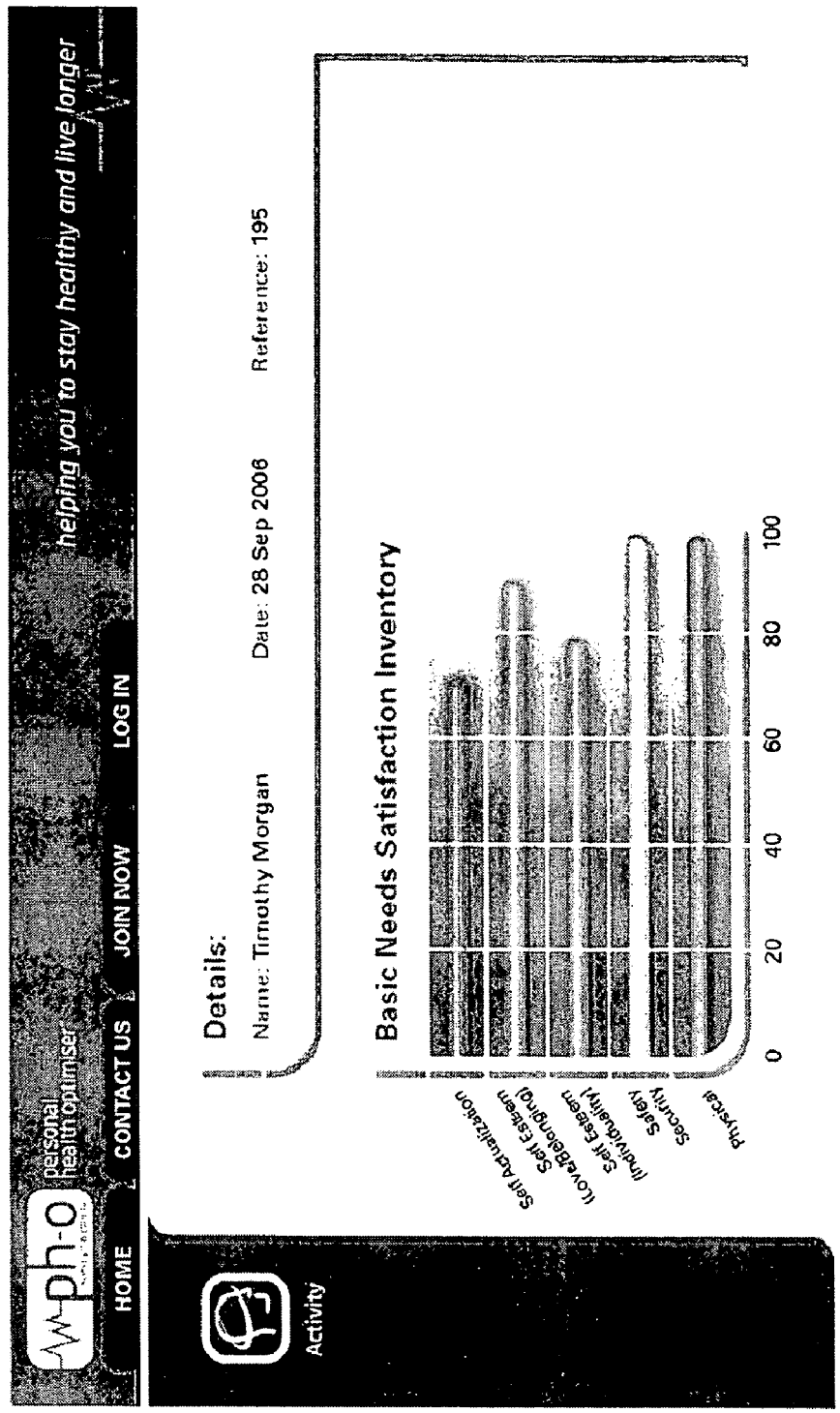

Step 1306 proceeds to step 1308 to generate BNSI category graph data based on the user's modified BNSI score for the selected category. The BNSI category graph data allows the client device 102 to generate a graphical representation (e.g. a graph) of the value of the user's category score parameter for each BNSI category) as recorded from the most recent BNSI survey data entered by the user. An example of a BNSI category graph is shown as item 1800 in FIG. 18D, and in FIG. 29.

Step 1308 proceeds to step 1310 to determine whether all of the BNSI categories have been processed. If not, step 1310 proceeds to step 1302 to select another BNSI category. Otherwise, step 1310 proceeds to step 1312 to start analysing the category scores.

Step 1312 selects a BNSI category and retrieves the category score parameter value for the selected category. Step 1312 proceeds to step 1314 to determine whether the category score parameter value for the selected category is greater than or equal to 83.3%, and less than or equal to 100%. If so, step 1314 proceeds to step 1316 to generate a BNSI recommendation indicating that no intervention is required, and then proceeds to step 1332. Otherwise, step 1314 proceeds to step 1318.

Step 1318 determines whether the category score parameter value for the selected category is greater than or equal to 66.6%, and less than 83.3%. If so, step 1318 proceeds to step 1320 to generate a BNSI recommendation indicating that the user's activity level for the selected BNSI category is set at level 2, and then proceeds to step 1332. Otherwise, step 1318 proceeds to step 1322.

Step 1322 determines whether the category score parameter value for the selected category is greater than or equal to 33.3%, and less than 66.6%. If so, step 1322 proceeds to step 1324 to generate a BNSI recommendation indicating that the user's activity level for the selected BNSI category is set at level 4, and then proceeds to step 1332. Otherwise, step 1322 proceeds to step 1326.

Step 1326 determines whether the category score parameter value for the selected category is greater than or equal to 16.6%, and less than 33.3%. If so, step 1326 proceeds to step 1328 to generate a BNSI recommendation indicating that the user's activity level for the selected BNSI category is set at level 6, and then proceeds to step 1332. Otherwise, step 1326 proceeds to step 1330 to generate a BNSI recommendation indicating that the user needs to seek professional advice (e.g. from a general physician); i.e. less than 16.6%. Step 1330 then proceeds to step 1332.

Step 1332 determines whether all of the BNSI categories have been analysed. If not, step 1332 proceeds to step 1312 to select another BNSI category for analysis. Otherwise, step 1332 proceeds to step 1334 (as shown in FIG. 13B).

Step 1334 retrieves the user's BMI parameter value from the database 110. Step 1334 proceeds to step 1336 to determine whether the user's BMI parameter value is greater than or equal to 20, and less than or equal to 25. If so, step 1336 proceeds to step 1348. Otherwise, step 1336 proceeds to step 1338.

Step 1348 retrieves the user's WC, TG, HDL-C, BP and FG recommendations from the database 110. Step 1348 proceeds to step 1350 to determine whether the user's WC recommendation indicates that the user needs to reduce the user's WC parameter value. If so, step 1350 proceeds to step 1342. Otherwise, step 1350 proceeds to step 1352.

Step 1352 determines whether the user's TG recommendation indicates that the user needs to reduce the user's TG parameter value. If so, step 1352 proceeds to step 1342. Otherwise, step 1352 proceeds to step 1354.

Step 1354 determines whether the user's HDL-C recommendation indicates that the user needs to increase the user's HDL-C parameter value. If so, step 1354 proceeds to step 1342. Otherwise, step 1354 proceeds to step 1356.

Step 1356 determines whether the user's BP recommendation indicates that the user needs to reduce the user's BP parameter values (e.g. the SBP and/or DBP parameter values). If so, step 1356 proceeds to step 1342. Otherwise, step 1356 proceeds to step 1358.

Step 1358 determines whether the user's FG recommendation indicates that the user needs to reduce the user's FG parameter value. If so, step 1358 proceeds to step 1342. Otherwise, step 1358 proceeds to step 1360.

Step 1338 determines whether the user's BMI parameter value is less than 20. If it is, step 1338 proceeds to step 1340 to generate a BNSI recommendation that encourages the user to take a healthy diet, and then proceeds to step 1360. Otherwise, step 1338 proceeds to step 1342 (i.e. user's BMI parameter value is >25).

Step 1342 generates a BNSI recommendation that encourages the user to take a healthy diet and to exercise. Step 1342 then proceeds to step 1346 where the activity level for the user's "Physical" BNSI category is increased by two (i.e. if the user's "Physical" BNSI category activity level is set at level 2, step 1346 sets the "Physical" BNSI category activity level to level 4). Step 1346 proceeds to step 1360, where execution returns to process 400.

Figure 14:
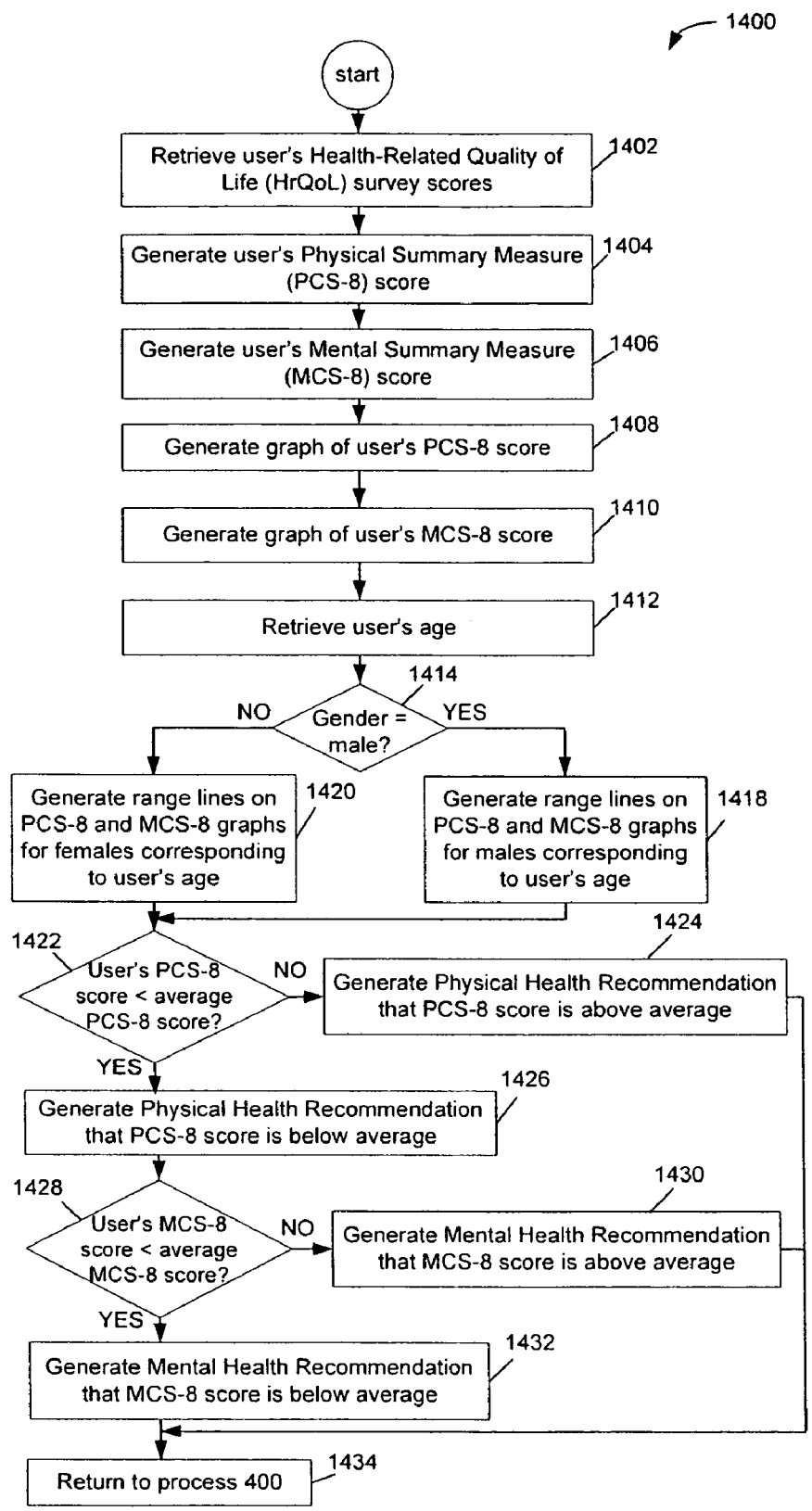

FIG. 14 is a flow diagram of the process 1400 for generating recommendations based on the user's responses to the health-related quality of life survey (e.g. the SF-8™ Health Survey). Health-related quality of life in the individual customer can be evaluated with an appropriately validated questionnaire (e.g. SF-8™ Health Survey). The impact of the primary prevention and primary intervention recommendations can be measured with the health-related quality of life survey. It can also be considered an indirect measure of the compliance with the primary prevention and primary intervention recommendations.

Process 1400 begins at step 1402 by retrieving the user's health-Related Quality of Life (HrQoL) survey scores. Step 1402 proceeds to step 1404 to generate a Physical Summary Measure of Health (PCS-8) score for the user. Step 1404 then proceeds to step 1406 to generate a Mental Summary Measure of Health (MCS-8) score for the user.

A method for determining the PCS-8 score and the MCS-8 score is described in detail on pages 15-19 of Ware J E, Kosinski M, Dewey J E and Gandbek B, *How to Score and Interpret Single-Item Health Status Measures. A Manual for Users of the SF-8™ Health Survey*, Lincoln, R.I., QualityMetric Inc., 2001. These normalized scores can be compared to the population-based average and percentile scores (e.g. for the $25^{th}$, $50^{th}$, and $75^{th}$ percentile as derived from a large US population-based study of males and females (approximately 13,000) of various ages ranges from 18-24 years up to 75 years and over (as described in detail on pages 20-24; 70-114 of Ware J E, Kosinski M, Dewey J E and Gandbek B, *How to Score and Interpret Single-Item Health Status Measures: A Manual for Users of the SF-8™ Health Survey*, Lincoln, R.I., QualityMetric Inc., 2001). An acceptable minimum health and well-being goal score using this method would be PCS-8 score and MCS-8 that is greater than or equal to the $75^{th}$ percentile population-based score for the SF-8™ survey (as collected from a sufficiently large demographic sample) for the age and gender of the user.

Step 1408 generates PCS-8 graph data based on the user's history of PCS-8 scores as retrieved from the database 110. The PCS-8 graph data allows the client device 102 to generate a graphical representation (e.g. a graph) of the changes in the value of the user's PCS-8 score as recorded on different dates over the time period selected at step 402. An example of a PCS-8 graph is shown as item 1852 in FIG. 18E, which may include data points 1860 representing the user's PCS-8 score values on different dates.

Figure 28:
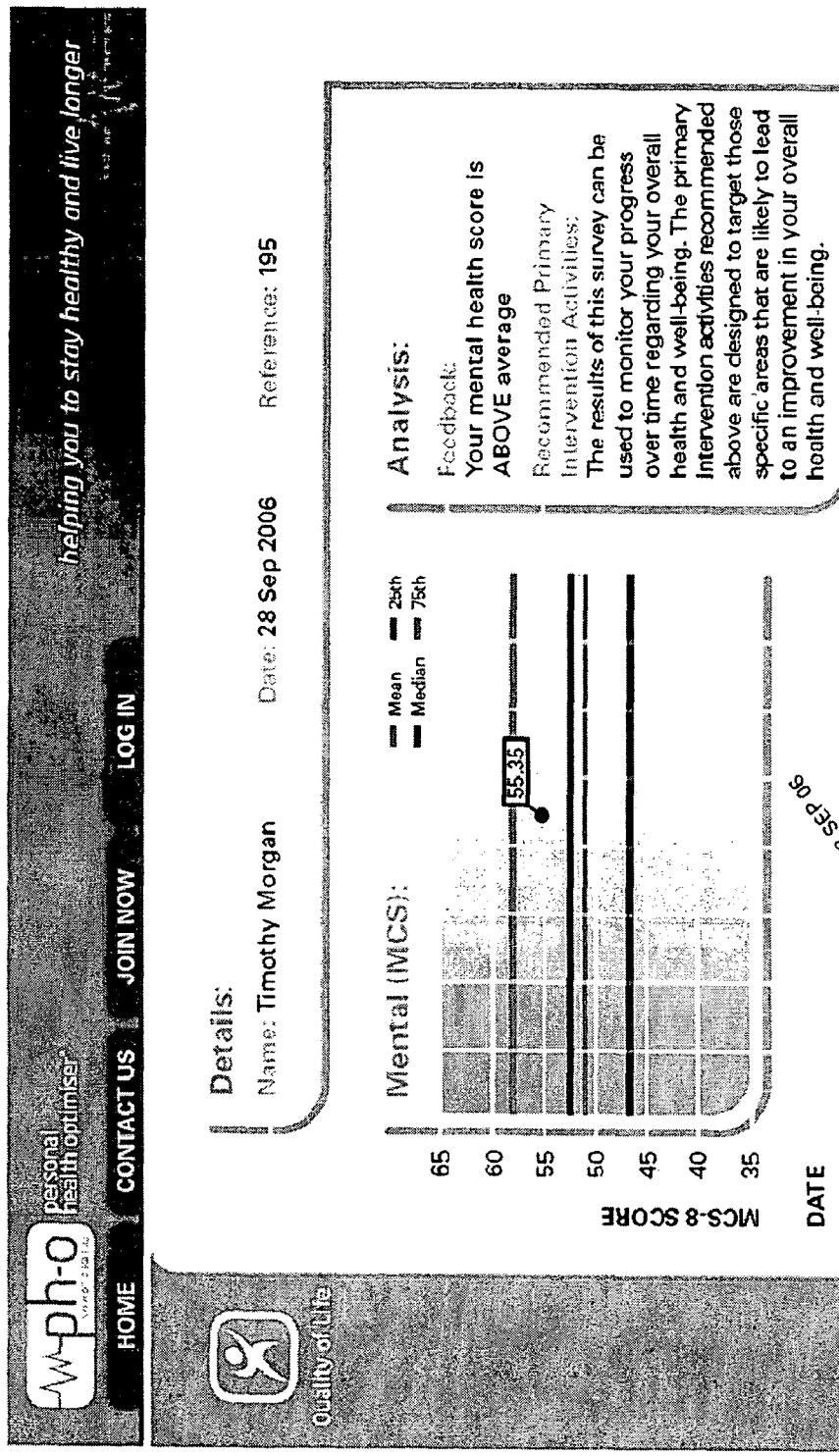

Step 1408 then proceeds to step 1410 to generate MCS-8 graph data based on the user's history of MCS-8 scores by retrieving the user's MCS-8 parameter values from the database 110. The MCS-8 graph data allows the client device 102 to generate a graphical representation (e.g. a graph) of the changes in the user's MCS-8 parameter values as recorded on different dates over the time period selected at step 402. An example of a MCS-8 parameter graph is shown as item 1862 in FIG. 18E, which may include data points 1870 representing the user's MCS-8 parameter values on different dates. Another example of an interface display providing the MCS graph is shown in FIG. 28, which includes a display of the related feedback and primary intervention activities.

Step 1412 retrieves the user's age from the database 110 and proceeds to step 1414 to determine whether the user's gender is identified as male. If so, step 1414 proceeds to step 1418 which based on the user's particular age and male gender retrieves the corresponding data from database 102 in order to generate the range lines for each of the PCS-8 graph and MCS-8 graph. Otherwise, step 1412 proceeds to step 1420 which based on the user's particular age and female gender retrieves the corresponding data from database 102 in order to generate the range lines for the PCS-8 graph and MCS-8 graph. An example of this is shown for PCS-8 graph 1852 which depicts the $75^{th}$ percentile score range line 1854, US average score range line 1858, and $25^{th}$ percentile score range line 1856. Another example of this is shown for the MCS-8 graph 1862 which depicts the $75^{th}$ percentile score range line 1864, US average score range line 1868, and 25$^{th}$ percentile score range line 1866. The data used to generate the range lines for males is contained in pages 56-59 and for females in pages 60-63 of Ware J E, Kosinski M, Dewey J E and Gandbek B, *How to Score and Interpret Single-Item Health Status Measures. A Manual for Users of the SF-8™ Health Survey*, Lincoln, R.I., QualityMetric Inc., 2001, respectively. Steps 1418 and 1420 both proceed to step 1422.

Step 1422 determines whether the user's most recent PCS-8 score is less than the average PCS-8 score (i.e. the mean percentile score for the physical component of the HrQoL survey). If so, step 1422 proceeds to step 1426 to generate a Physical Health recommendation indicating that the user's PCS-8 score is below average (e.g. as depicted by 1896 in FIG. 18E), and step 1426 then proceeds to step 1428. Otherwise, step 1422 proceeds to step 1424 to generate a Physical Health recommendation indicating that the user's PCS-8 score is above average, and step 1426 then proceeds to step 1434.

Step 1428 determines whether the user's most recent MCS-8 score is less than the average MCS-8 score (i.e. the mean percentile score for the mental component of the HrQoL survey). If so, step 1428 proceeds to step 1432 to generate a Mental Health recommendation indicating that the user's MCS-8 score is below average, and step 1432 then proceeds to step 1434. Otherwise, step 1428 proceeds to step 1430 to generate a Mental Health recommendation indicating that the user's MCS-8 score is above average as depicted in FIG. 28 and by 1898 in FIG. 18E, and step 1430 then proceeds to step 1434. At step 1434, execution returns to process 400.

Figure 15:
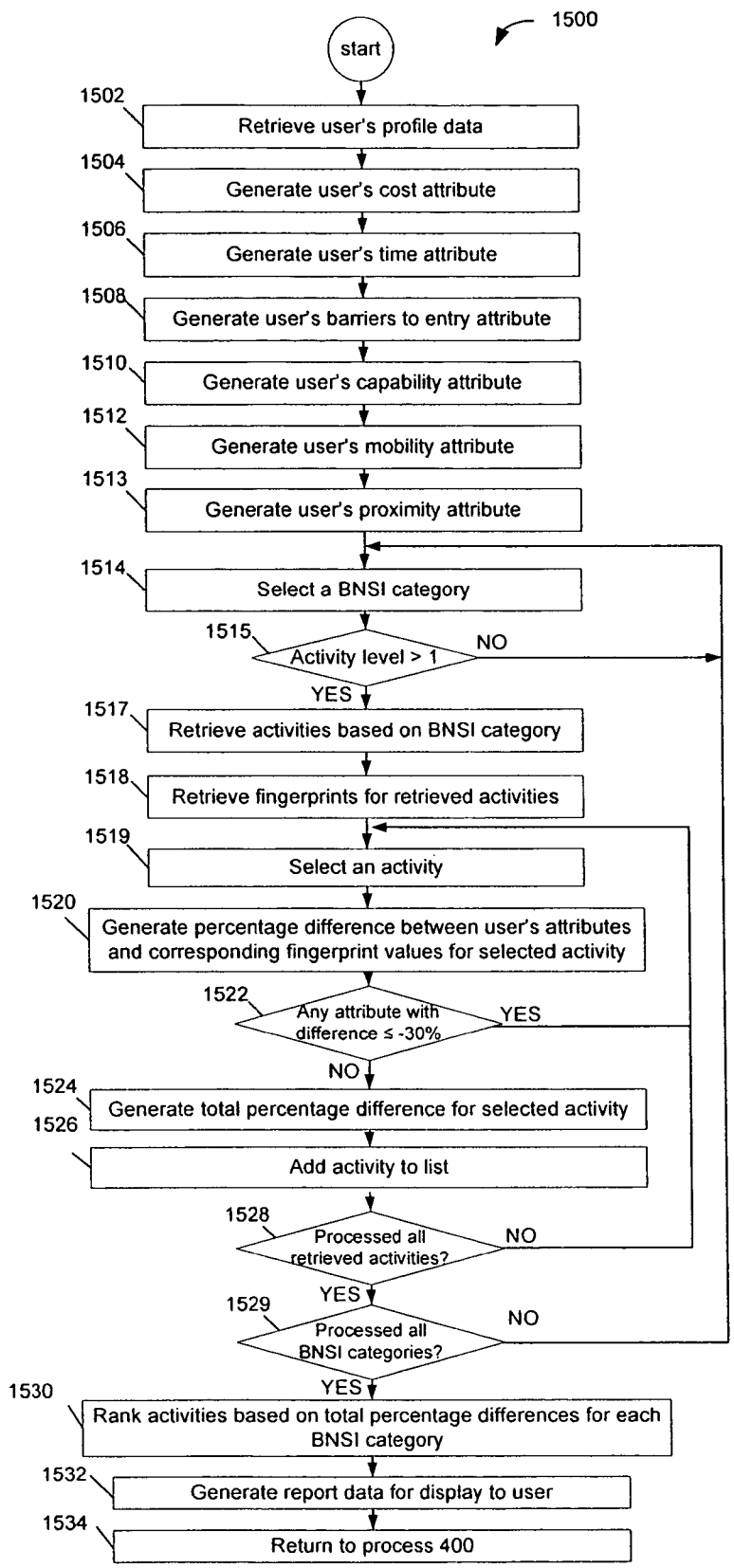

FIG. 15 is a flow diagram of the process 1500 for generating activity attributes for the user based on the user's profile, and recommending activities for improving the user's current physical/mental health based on a comparison of the user's activity attributes with fingerprints for different activities, and also based on the number of activities recommended from the activity level (as previously described in process 1300 for setting the activity level and as also shown in Table 15 as the number of recommended primary interventions).

The system 100 uses the demographic factors (refer to Table 3 below) of the user to provide data for the analysis process 400 that then recommends primary prevention and/or primary intervention activities to the user. A user's affinity to activity initiation and/or completion can be correlated with the degree of difference between their personal situation (demographics and anthropometrics) and the individual activity in question. Demographic and anthropometric measures can be used as surrogate markers for the resource level of a user as it relates to activity initiation and/or completion. The preference for using a particular activity remains with the user and this method provides a basis for matching the activity to the user. The system 100 allows an individual's likely preference for any activity to be mapped, measured and refined over time. The purpose being to align prospective activity recommendations with the user's basic needs over time as a means to maintain or improve health and well-being.

The following list of surrogate markers for the attribute data in Table 3 are used as examples and are not intended to be exhaustive.

TABLE 3

| Attribute | Surrogate markers |
| --- | --- |
| Cost | Average annual household/family income |
| Time | Average hours worked per week |
| Barriers to entry | Size of social network (for example, taking into account a. Marriage/Life partnership; b. Contacts with close friends and relatives; c. Church membership; d. Informal and group associations. |

TABLE 3-continued

| Attribute | Surrogate markers |
| --- | --- |
| | Intimate contacts (a. and b.) are weighted more heavily than c. and d. (as discussed in Berkman L. F., Syme, S. L. Social networks, host resistance, and mortality: A nine-year follow-up study of Alameda County residents, 1979, Am. J. Epidemiol., 109(2), pp. 186-204)); and gender |
| Level of capability | Educational attainment/level of training |
| Mobility | SF-8 physical health scores; age; and number of dependents |
| Proximity | Postcode of primary residence |

Process 1500 begins at step 1502 by retrieving the user's user profile data from the database 110. Step 1502 proceeds to step 1504 to generate a cost attribute for the user based on data stored or submitted for one or more surrogate demographic markers. For example, the cost attribute is the generated using Table 4 as the score corresponding to the user's annual household/family income range according to the user's profile data. Table 4 associates a score and monetary cost range with different brackets of annual household income. The "*" symbol in Table 4 indicates that the upper limit is based on approximately one third of the start of the highest income scale (assumed to be AU$80,000 in Table 4). The user's cost attribute is part of the user's fingerprint that is stored in the database 110. Step 1504 then proceeds to step 1506.

TABLE 4

| Surrogate Demographic Marker - Annual Household/Family Income (AU$) | Activity Cost (AU$) | Score |
| --- | --- | --- |
| <16,500 | ≦50 | 2 |
| ≧16,500 and ≦32,999 | >50 and ≦250 | 4 |
| ≧33,000 and ≦52,999 | >250 and ≦1000 | 6 |
| ≧53,000 and ≦79,999 | >1000 and ≦5000 | 8 |
| ≦80,000 | >5000 and ≦26,667* | 10 |

Step 1506 generates a time attribute for the user based on data stored or submitted for one or more surrogate demographic markers. For example, the time attribute is generated using Table 5 as the score corresponding to the number of hours worked per week according to the user's profile data. Table 5 associates a score and cost (in hours) with different numbers of hours worked each week. The user's time attribute is part of the user's fingerprint that is stored in the database 110. Step 1506 then proceeds to step 1508.

TABLE 5

| Surrogate Demographic Marker - Average Hours Worked per Week | Activity Time (hours) | Score |
| --- | --- | --- |
| ≧60 | >0 and ≦0.5 | 1 |
| ≧45 and ≦59 | >0.5 and ≦1.0 | 3 |
| ≧30 and ≦44 | >1.0 and ≦2.0 | 5 |
| ≧16 and ≦29 | >2.0 and ≦8.0 | 8 |
| ≧1 and ≦15 | >8.0 and ≦16.0 | 9 |
| Nil (zero) | >16.0 and ≦32.0 | 10 |

Step 1508 generates a barriers to entry attribute based on data stored or submitted for one or more surrogate demographic markers. For example, the barriers to entry attribute is generated based on the score from Table 6 corresponding to the percentile range of the user's MCS-8 score, and the score from Table 7 corresponding to the size/type of the user's social network, according to user's profile data. Table 6 associates a score with the percentile range of the user's overall MCS-8 score. Table 7 associates a score with different sizes/types of social networks. The user's barriers to entry attribute is a score generated based on a weighted sum of the scores determined from Tables 6 and 7 respectively, according to Equation 4.

Barriers to entry attribute=(Score from Table 6×60%)+(Score from Table 7×40%)   Equation 4

A barriers to entry attribute score of 10 indicates that the user has very low social barriers to participating in activities. A barriers to entry attribute score of 7.5 indicates that the user has low social barriers to participating in activities. A barriers to entry attribute score of 5 indicates that the user has medium social barriers to participating in activities. A barriers to entry attribute score of 2.5 indicates that the user has high social barriers to participating in activities. The user's barriers to entry attribute is part of the user's fingerprint that is stored in the database 110. Step 1508 then proceeds to step 1510.

TABLE 6

| Surrogate Demographic Marker - Overall MCS-8 Score | Score |
|---|---|
| <25$^{th}$ percentile | 2.5 |
| ≧25$^{th}$ percentile and <50$^{th}$ percentile | 5.0 |
| ≧50$^{th}$ percentile and <75$^{th}$ percentile | 7.5 |
| ≧75$^{th}$ percentile and ≦100$^{th}$ percentile | 10.0 |

TABLE 7

| Surrogate Demographic Marker - Size of Social Network | Score |
|---|---|
| Marriage/life partner? | Yes = 5; and<br>No = 0 |
| Number of close friends and/or relatives | No friends/relatives = 0;<br>1 friend/relative = 0.5;<br>2 friends/relatives = 1.0;<br>3 friends/relatives = 1.5;<br>4 friends/relatives = 2.0; and<br>>4 friends/relatives = 2.5 |
| Church membership? | Yes = 1.5; and<br>No = 0 |
| Number of informal and/or group associations | No associations = 0;<br>1 association = 0.25;<br>2 associations = 0.5;<br>3 associations = 0.75; and<br>≧4 associations = 1.0 |

Step 1510 generates a capability attribute based on data stored or submitted for one or more surrogate demographic markers. For example, the capability attribute is score value is generated using Table 8 as the score corresponding to the user's educational level according to the user's profile data. Table 8 associates a score with different levels of education attained by the user. The user's capability attribute is part of the user's fingerprint that is stored in the database 110. Step 1510 then proceeds to step 1512.

TABLE 8

| Surrogate Demographic Marker - Education Level | Activity Minimum Education Requirement | Score |
|---|---|---|
| High school or less | High school or less | 5.00 |
| Some college/university | Some college/university | 6.25 |
| Bachelor's/undergraduate degree | Bachelor's/undergraduate degree | 7.50 |
| Graduate/postgraduate degree | Graduate/postgraduate degree | 10.00 |

Step 1512 generates a mobility attribute based on data stored or submitted for one or more surrogate demographic markers. For example, the mobility attribute is generated based on the score from Table 9 corresponding to the percentile range of the user's PCS-8 score, the score from Table 10 corresponding to the user's age bracket, and the score from Table 11 corresponding to the number of dependents for the user, according to the user's profile data. Table 9 associates a score with the percentile range of the user's overall PCS-8 score. Table 10 associates a score value with different age brackets. Table 11 associates a score with different numbers of dependents. The mobility attribute is a score generated based on a weighted sum of the scores determined from Tables 9, 10 and 11 respectively, according to Equation 5.

$$\text{Mobility attribute} = (\text{Score from Table } 9 \times 60\%) + \\ (\text{Score from Table } 10 \times 30\%) \\ (\text{Score from Table } 11 \times 10\%) \quad \text{Equation 5}$$

A mobility attribute of 10 indicates that the user has very high mobility. A mobility attribute of 7.5 indicates that the user has high mobility. A mobility attribute of 5 indicates that the user has medium mobility. A mobility attribute score of 2.5 indicates that the user has low mobility. The user's mobility attribute is part of the user's fingerprint that is stored in the database 110. Step 1512 then proceeds to step 1513.

TABLE 9

| Surrogate Demographic Marker - Overall PCS-8 Score | Score |
|---|---|
| <25$^{th}$ percentile | 2.5 |
| ≧25$^{th}$ percentile and <50$^{th}$ percentile | 5.0 |
| ≧50$^{th}$ percentile and <75$^{th}$ percentile | 7.5 |
| ≧75$^{th}$ percentile and ≦100$^{th}$ percentile | 10.0 |

TABLE 10

| Surrogate Demographic Marker - Age (yrs) | Score |
|---|---|
| ≧12 and <18 | 5.0 |
| ≧18 and <40 | 10.0 |
| ≧40 and ≦60 | 7.5 |
| >60 | 2.5 |

TABLE 11

| Surrogate Demographic Marker - Number of Dependents | Score |
|---|---|
| Nil (zero) | 10.0 |
| ≧1 and ≦3 | 7.5 |
| ≧4 and ≦5 | 5.0 |
| ≧6 | 2.5 |

Step 1513 generates a proximity attribute based on data stored or submitted for one or more surrogate demographic markers. For example, the proximity attribute is generated using Table 12 as the score corresponding to the geographic region of the postcode for the user's address, according to the user's profile data. Table 12 associates a score with different geographic regions (e.g. outback, regional, suburban, and inner suburban), and each region is associated with areas identified by different postcodes. For example, the inner suburban region includes the postcode(s) for the central business district (CBD) and includes postcodes for areas approximately up to 5 kms from the General Post Office (GPO) or main post office of a region, state or territory. In Australia, a list of postcodes is available from Australia Post. The user's proximity attribute is part of the user's fingerprint that is stored in the database 110. Step 1513 then proceeds to step 1514.

TABLE 12

| Surrogate Demographic Marker - Geographic area (e.g. by postcode) | Typical Proximity of Activity | Score |
|---|---|---|
| Outback | Outback | 2.5 |
| Regional | Regional | 5.0 |
| Suburban | Suburban | 7.5 |
| Inner Suburban | Inner Suburban | 10.0 |

Step 1514 selects a BNSI category and its corresponding activity level from the database 110 as determined by process 1300, and then proceeds to step 1515.

Step 1515 determines whether the activity level for the selected BNSI category is greater than 1. If so, step 1515 proceeds to step 1517 to retrieve all the activities from the database 110 for that BNSI category. Otherwise step 1515 proceeds to step 1514 to select another BNSI category.

Step 1517 proceeds to step 1518 to retrieve, from the database 110, the activity fingerprint for each activity retrieved at step 1517.

The database 110 stores activity fingerprints for a range of activities. To allow a consistent method for matching the activity to the individual person each activity is defined by a core set of six attributes (cost, time, barriers to entry, level of capability, mobility and proximity) that are each scored from 0 to 10 and weighted on a percentage basis from 0 to 100%. The weighted attribute score is the score (e.g. 5) multiplied by the predetermined weighting percentage for that activity (e.g. 30%; 5×30%=1.5). The activity fingerprint for an activity is the pattern of individual weighted attribute scores for that activity, and which is compared with the corresponding attribute scores in the user's fingerprint to generate a percentage difference for each attribute.

The method for determining the rank order of the activities is to subtract the weighted attribute score for the prospective activity from the corresponding weighted attribute scores for the user's profile (or user's fingerprint). The same weightings used for the particular activity are applied to the user's profile in each instance. The available activity pool can then be ordered based on the sum of the differences in the weighted attribute scores between the user's profile and for each activity fingerprint. Activities that have a positive sum of the differences are then selected from the available activity pool for recommendation to the user.

Step 1519 selects a single activity from the activity pool and proceeds to step 1520, where the percentage difference between the user's fingerprint attributes (i.e. the user's cost, time, barriers to entry, capability, mobility and proximity attribute values) and the corresponding fingerprint values for the activity selected in step 1519 are calculated. The percentage difference for an activity is determined using Equation 5, by subtracting the weighted score for the activity attribute (i.e. cost, time, barriers to entry, level of capability, mobility and proximity) from the user's corresponding attribute score which has been previously multiplied by the corresponding activity attribute weighting, and this is then expressed as a percentage of the total weighted score for that activity.

$$\text{Percentage difference for attribute (\%)} = \left[ \frac{\left( \begin{array}{c} \text{User's score} \\ \text{for attribute} \end{array} \times \begin{array}{c} \text{attribute} \\ \text{weighting} \end{array} \right) - \begin{array}{c} \text{weighted score} \\ \text{for attribute} \end{array}}{\begin{array}{c} \text{weighted score} \\ \text{for attribute} \end{array}} \right] \times 100 \quad \text{Equation 5}$$

Because this rank order method has the potential to average out negative attribute scores that could impact on the successful initiation and/or completion of the activity, the analysis process 400 screens the activities so as to not to add any activities to the recommended activity list if any single attribute scores a negative difference greater than or equal to a threshold value (e.g. 30%) of the required weighted score for that particular activity attribute. For example, if a user's weighted score for Mobility for the activity of jogging was 2.10 (i.e. 4.2×50%) then according to Table 13, the difference would equal −0.90 (i.e. 2.10−3.00=−0.90), which means the user is under-resourced for that particular activity attribute and because the level of the resource capability is −30% (i.e. (−0.90/3.00)×100%=−30%), the process would not recommend jogging as an activity to the user under these particular circumstances.

Table 13 shows an example of the activity fingerprint for jogging.

TABLE 13

| Activity Attribute | Score (1 to 10) | Weighting (0% to 100%) | Weighted Score |
|---|---|---|---|
| Cost | 1 | 10% | 0.10 |
| Time | 3 | 10% | 0.30 |
| Barriers to entry | 1 | 10% | 0.10 |
| Level of capability (education and/or training) | 2 | 10% | 0.20 |
| Mobility | 6 | 50% | 3.00 |
| Proximity | 2 | 10% | 0.20 |
| Total Weighted Score | | | 3.90 |

The weighting percentage given to each activity attribute is determined by the particular BNSI category that the activity falls within and, in one embodiment, the same weightings are maintained across all activities within a particular BNSI category. For example, all physical BNSI category activities have a weighting percentage the same as that shown in Table 13.

Step 1520 proceeds to step 1522 to determine whether the percentage difference for any of the user's attributes is less than or equal to a threshold value (e.g. −30%). If so, the user does not have sufficient resources to participate in the activity, and step 1522 proceeds to step 1519 to select another activity. Otherwise, step 1522 proceeds to step 1524 to generate the total percentage difference for the selected activity by generating the sum of the percentage differences (determined using Equation 5) for each attribute for that particular activity.

Step 1524 proceeds to step 1526 to add the selected activity to a list of activities for prospective recommendation to the user (e.g. as treatment for the user's physical, physiological and/or psychological condition).

Step 1526 proceeds to step 1528 to determine whether all of the activities retrieved at step 1517 have been processed. If not, step 1528 proceeds to step 1519 to select another activity. Otherwise, step 1528 proceeds to step 1529 to determine if all BNSI categories have been processed. If so, step 1529 proceeds to step 1530 to rank the activities in the list. Otherwise step 1529 proceeds to step 1514 to select another BNSI category.

In step 1530 the total percentage difference for each activity serves as the basis for ranking the activities in the list for each BNSI category (highest positive percentage to lowest).

FIG. 17B contains a representative example of a randomised modified BNSI questionnaire and a user's affective responses. The percentage score for this example are shown in Table 14.

TABLE 14

| BNSI category | Score (%) for results shown in FIG. 17B |
| --- | --- |
| Self-actualisation needs | 85.55% (with raw scores of 4, 4 and 5) |
| Self-esteem - Love/belonging needs | 77.77% (with raw scores of 5, 6 and 6) |
| Self-esteem - Individuality needs | 88.89% (with raw scores of 6, 6 and 7) |
| Safety/security needs | 88.89% (with raw scores of 7, 6 and 6) |
| Physical needs | 66.66% (with raw scores of 5, 4 and 6) |

Step 1530 then uses the following logic to determine the level of primary intervention suggested to the user. Table 15 associates different BNSI category percentage score ranges with different types of intervention for recommendation to the user, and part of Table 15 relates to determining the activity level of a BNSI category as described in relation to process 1300. The percentage range corresponding to the percentage score of the BNSI category determines the number of primary interventions to be recommended to the user (represented by integer n). For example, in Table 14, the physical needs BNSI category percentage score is 66.66% which according to Table 15 this corresponds to a requirement to recommend 2 (i.e. n=2) primary interventions (i.e. activities) to the user.

TABLE 15

| BNSI Category Percentage Score Range | Intervention |
| --- | --- |
| 0 to <16.6% | Suggest seek professional advice |
| ≧16.6 to <33.3% | Provide the upper range (n = 6) of recommended primary interventions |
| ≧33.3 to <66.6% | Provide the middle range (n = 4) of recommended primary interventions |
| ≧66.6 to <83.3% | Provide the lower range (n = 2) of recommended primary interventions |
| ≧83.3 to 100% | (No intervention) |

Step 1530 ranks the list of recommended activities according to what is likely to be the most relevant to the user, thus increasing the probability of activity initiation and completion. Ranking of the activities involves generating a rank order that is particular to each of the user's primary basic needs area (i.e. BNSI category) for improvement (i.e. self-actualization, self-esteem—love/belonging, self-esteem—individuality, safety/security and physical). The rank order is generated on the primary assumption that positive behaviour modifications are more likely to be incorporated into the user's lifestyle if the recommended activities are both consistent with the user's affective needs and the user's capacity to undertake them. This is reflected by the process suggesting those activities that involve the least change from an user's current make-up. The ranking process is flexible so as to capture changes in an individual's make-up over time so that the prospective range of activities suggested evolve as that person grows and matures thus providing long-term utility for the process. Similarly any community-related changes in the activity attributes can also be captured over time.

For users with a high level of resources for each attribute a rank order of prospective activities can be determined based on the highest to lowest positive scores obtained but with the presentation of the order of recommended activities to the user randomised (by means of a random number generator) in order to prevent constant bias toward high resource level activities in such users.

Step 1530 proceeds to step 1532 to generate report activity data for the client device 102 to render report interface displays for display to the user. The number of activities generated for each BNSI category are determined from the activity level number and the rank order list of activities. An example of the activity report that the interface displays is shown as Recommended Primary Intervention Activities 1872 in FIG. 18D. Step 1532 then proceeds to step 1534, where executions returns to process 400.

The overall benefit of the personalized, weighted activity scoring is to ensure an internally consistent basis from which primary prevention/intervention activities can be recommended to the individual user by the system.

Figure 18D:
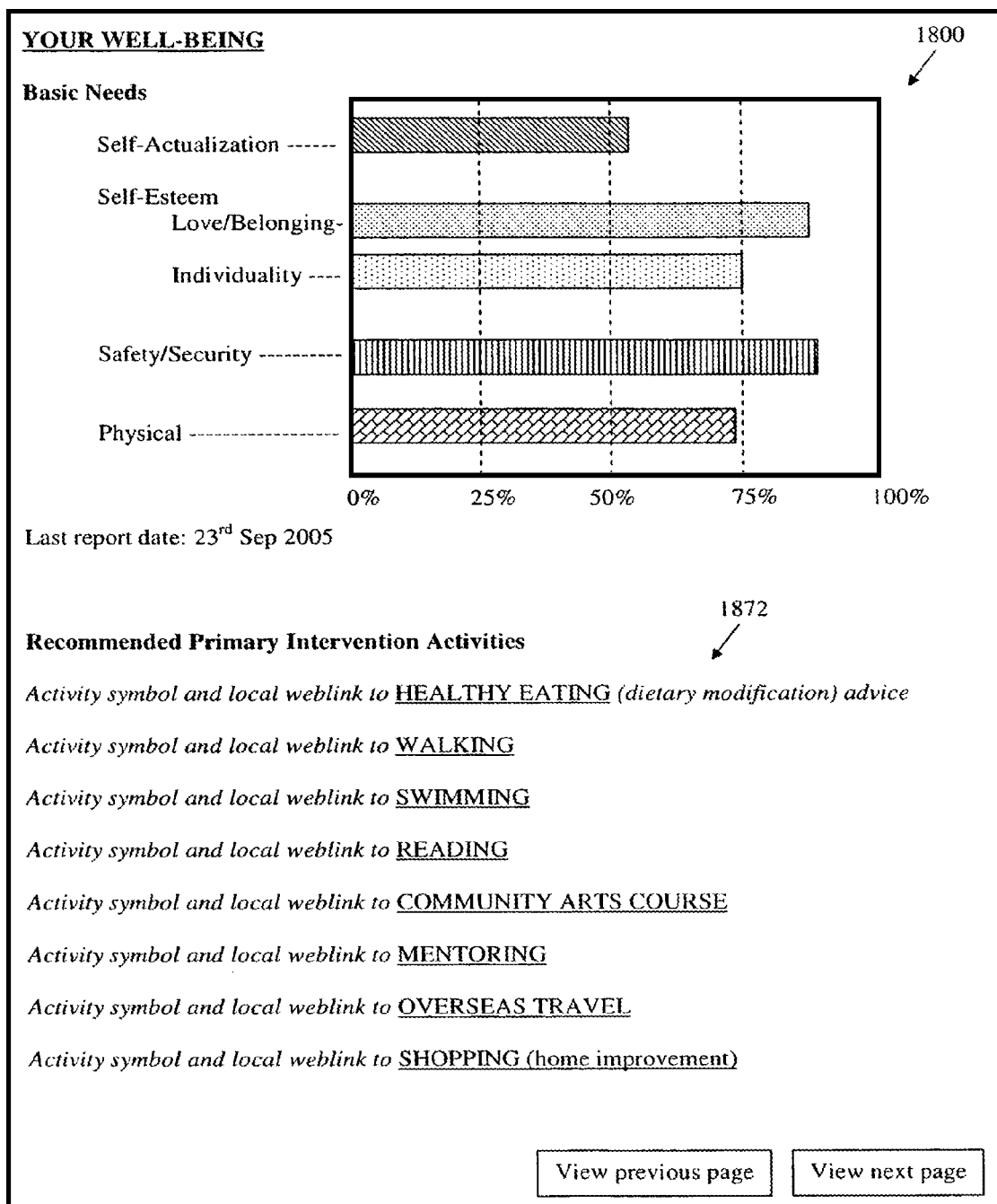
Figure 18E:
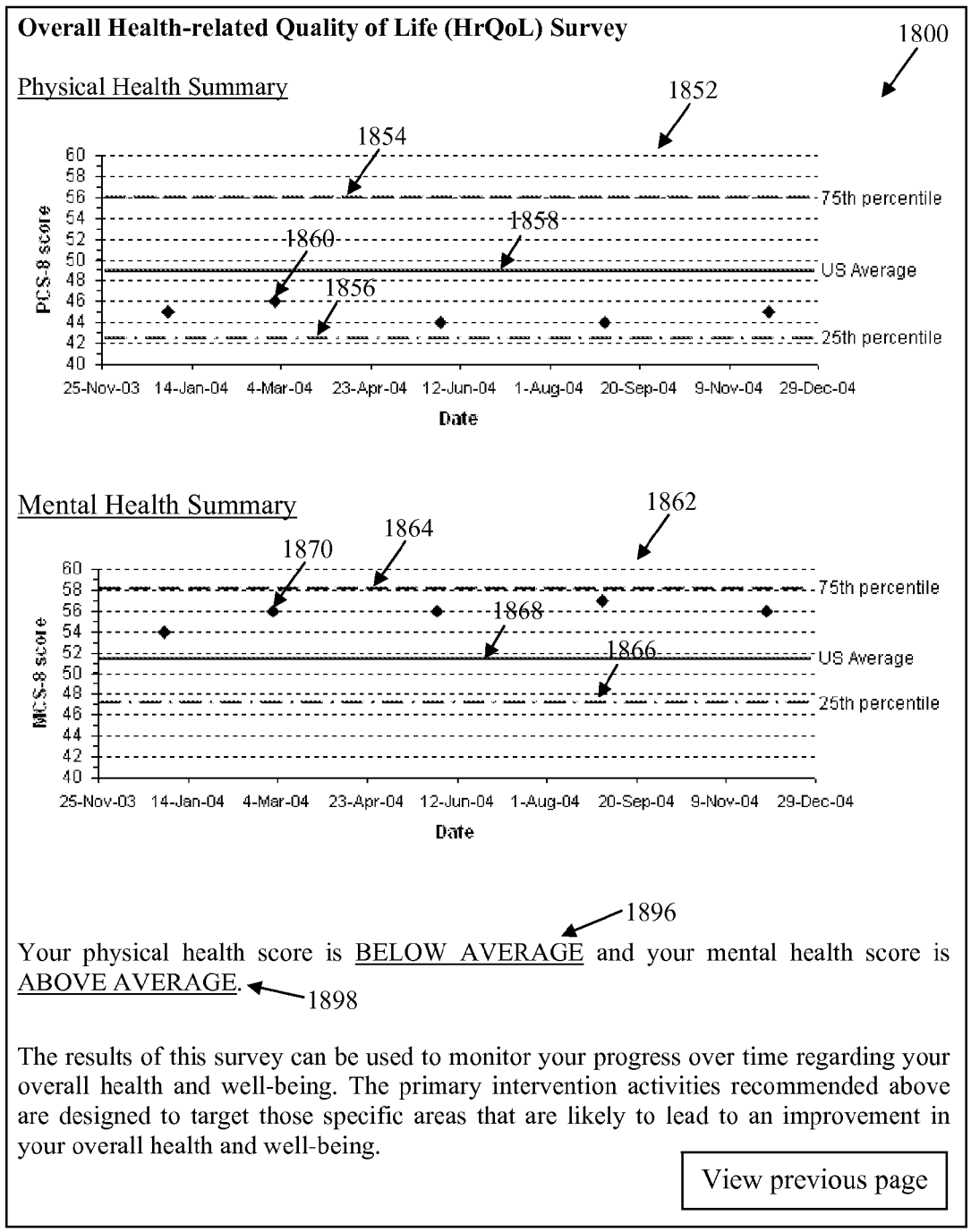

FIGS. 18A to 18E are screenshots of an exemplary report generated by the home diagnostic system 100. The data is then integrated into a 3-5 page customer report that provides a concise and understandable summary (e.g. health overview) with regards to risk factors metabolic syndrome and work-related stress (e.g. current status versus historical overview). Additional information regarding advice to consult a doctor can be automatically added to the report if their individual risk profile falls outside the generally accepted medical diagnostic criteria and/or risk thresholds. Suggested locations and/or resources for the recommended primary prevention/intervention activities are provided as part of the report, and accessible by respective hyperlinks 1872 as shown in FIG. 18D.

The output is formatted into graphical charts (bar graphs for modified BNSI survey and scatter plots for the SF-8 Health and Well-Being survey and the other biophysical parameters such as BMI, TGs, glucose levels, etc). Optionally, the output parameters can be visually designated with symbols (e.g. representing the value of the output parameters in the form of a measuring tape, scales, fuel gauge displays and/or dashboard indicators) to aid in the communication of key health parameters that the individual must self-monitor.

Specific suggestions regarding primary intervention are tailored to each individual and serve as a basis for improving health and well-being by focusing on those needs that can help restore the individual's balance. This could be a combination of activities for any one or more of the subsystems previously discussed. The purpose of the report is to provide a basis for empowering the individual to make informed decisions regarding their health and well-being. By enabling the individual to implement positive lifestyle changes at-home, measure their results and then re-assess them over time in a rigorous and scientific manner the very nature of preventive medicine as a personal discipline is re-enforced.

An activity feedback mechanism exists within the system 100 to obtain the individual's compliance with and views regarding the activities recommended. This is initiated once activities have been recommended to the customer. This ongoing compliance and quality check provides one of the means to update the system (e.g. activity fingerprints and demographic markers) based on the customer's feedback.

FIG. 19 is a flow diagram of the process 1900 for determining the user's compliance with the recommended activities, and for users to provide feedback on those activities. Process 1900 begins at step 1902 by retrieving the list of activities most recently recommended to the user. Step 1902 proceeds to step 1904 and the input interface 114 generates an activity feedback input interface 2000 (as shown in FIG. 20A) including a list of the recently recommended activities 2001, and input fields (e.g. radio buttons 2006) for the user to indicate whether or not the user participated in each of those activities. Examples of the feedback input interface displays 2000, 2002 and 2004 rendered at different points in time are shown in FIGS. 20A, 20B and 20C. The user selects the "Submit" button 2008 to confirm the selection, and the selection with a time stamp is stored in the database 110.

Step 1904 proceeds to step 1906 to determine whether the user's input from the activity feedback input interface 2000 indicates that the user has participated in a recommended activity. If so, step 1906 proceeds to step 1908. Otherwise, step 1906 proceeds to step 1912.

Step 1908 generates a detailed activity feedback input interface 2002 (as shown in FIG. 20B) including a list of activities 2003 which the user has participated in, and input fields (e.g. radio buttons 2010) for the user to indicate whether or not the user intends to continue participating in each of those activities. The user clicks on the "Submit" button 2012 to confirm the selection on the activity feedback interface 2002, and triggers step 1908 to proceed to step 1910. The user clicks on the button 2014 to return to the activity feedback interface 2002 to modify the user's selection of participated activities.

Step 1910 updates the database 110 to include the activities selected by the user for continued participation to the pool of activities for recommendation to the user in the next report generated by the analysis process 400. Step 1910 then proceeds to step 1912.

Step 1912 determines whether the user's input from the activity feedback input interface 2000 indicates that the user has not participated in a recommended activity. If so, step 1912 proceeds to step 1914. Otherwise, step 1912 proceeds to step 1918.

In step 1914 the input interface 114 generates a participation feedback input interface 2004 (as shown in FIG. 20C) including a list of activities 2005 which the user did not participate in, and input fields (e.g. radio buttons 2016 and text fields 2018) for the user to indicate why the user did not participate. The user clicks on the "Submit" button 2020 to confirm the selection on the participation feedback interface 2004, and triggers step 1914 to proceed to step 1916. The user clicks on the button 2022 to return to the activity feedback interface 2002 to modify the user's selection of participated activities.

Step 1916 stores the user's feedback from the participation feedback interface 2004 with a time stamp and the user's attribute (demographic) profile to the database 110. Step 1916 proceeds to step 1918, where execution returns to process 300.

Another benefit of the system 100 is that it allows the individual to evaluate the effectiveness of the latest new lifestyle fads that they may wish to try and/or any other new suggestions recommended by public health organizations. Also since avoidance of health risks (e.g. smoking, excessive drinking) often comes with increased education and understanding. Having an individual proactively monitor his or her health has been shown to lead to a reduction in risk-taking behavior over the longer-term (as discussed in Goetzel R. Z. et al. *The long-term impact of Johnson & Johnson's health and wellness program on employee health risks*., J. Occup. Environ. Med. 2002. 44(5), 417-24).

At the customers request the individual's data file and/or reports can be printed, downloaded or transmitted to their doctor (as needed) in a convenient file format (e.g. a PDF file).

The home diagnostic system 100 is particularly useful in minimising the risk of developing metabolic syndrome and work-related stress conditions and basic needs dissatisfaction given the dramatic impact that these have on economic productivity, health and well-being. In particular, the system 100 provides a user-friendly means for entering a range of biochemical, anthropometric, subjective-social and cognitive data in order to provide personalized feedback and self-help activity recommendations back to the individual consumer in a clear and concise report display, hardcopy print-out and/or electronic file.

Current medical practice primarily focuses on treating people once they have illness and then uses physical and chemical treatments with little or no emphasis on the mental, emotional and behavioural dimensions of illness (as discussed in Sobel, D. S., *Rethinking Medicine: Improving Health Outcomes With Cost-Effective Psychosocial Interventions*., Psychosomatic Medicine, 1995, May-June, 57(3), pp. 234-44.). The home diagnostic system 100 provides an alternative to the reliance on acute style clinical medicine, and offers new benefits over and above existing medical practice.

In order to allow individual empowerment, the system 100 can be used at home allowing the person to take control of their own actions for preventive medicine whilst still being advised to seek interventional medicine if and when the need arises, based upon generally accepted medical intervention guidelines (e.g. as described in the IDF consensus worldwide definition of the metabolic syndrome, April 2005 (available from <http://www.idf.org>; and as described in Zimmet P Z, Alberti K G M M, Shaw J E, *Mainstreaming the metabolic syndrome: a definitive definition*, MJA, 2005, 183(4), pp. 175-76).

The home diagnostic system 100 is accessible by users from home and provides a cost-effective prevention tool and/or means for primary intervention to maintain or improve the health and well-being of individuals. The system 100 also provides a means for self-help which can be used in the privacy of an individual's home.

Another advantage of the home diagnostic system 100 is that if the measurements for an individual triggers a particular biophysical medical intervention parameter or indicates that the individual is experiencing extreme psychosocial distress, the system 100 generates a suggestion to seek professional medical advice, which would allow the user to benefit from appropriate secondary intervention under the guidance and/or supervision of a medical professional. This system 100 can thus provide a cost-effective basis for the provision of medical care by ensuring that individuals seek help proactively but at the right time. Self-help medicine is a valuable part of medical care and its appropriate use can help to relieve the current burden on doctors, nurses and other allied medical professionals. A primary benefit offered by the home diagnostic system 100 is its potential to help restore the lost balance that currently exists between prevention and cure, with the latter currently dominating modern healthcare practice at great socioeconomic cost to the community.

The home diagnostic system 100 also allows users to self-monitor their lifestyle over time in order to minimise health-related disorders (e.g. metabolic syndrome and work-related stress) and provides recommended hyperlinks to health-related information on activities and/or behavioural modifications that may improve the user's health and well-being primarily through primary prevention or primary intervention.

The home diagnostic system 100 may help increase the longevity of users (decreasing mortality) and may improve the health and well-being of individuals (decreasing morbidity) by proactively shaping the user's health and well-being in a way consistent with the user's basic needs satisfaction. Both of these benefits can increase the productivity of the community where that user resides, and thus, has the potential to directly improve the economic standing of that community. Improving productivity is particularly important in societies that have aging populations because the community at-large increasingly relies on the work of fewer people in order to maintain the required level of economic activity essential for delivery of health, social and educational services.

The home diagnostic system 100 further provides a cost-effective means of preventive medicine that is controlled by the individual consumer, and which ultimately prevents or decreases the use of more expensive secondary interventions involving pharmacological agents (such as cholesterol reducers, antihypertensives, antidiabetics and antidepressants) or surgical procedures to improve cardiovascular and/or metabolic function. Moreover, the expansion of cost-effective preventive medicine will mean that secondary interventions will become more effective because if and when they are needed they will be increasingly applied to individual consumers with a lower state of disease.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the appended claims rather than by the foregoing description. All variations coming within the meaning and range of equivalency of the claims are embraced within their scope.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A diagnostic computer system, comprising:
   a processor implemented with a software-controlled computer, dedicated hardware circuits, or a combination of a software-controlled computer and dedicated hardware circuits, the processor being configured to:
   (i) generate an input interface to receive user profile data, physical data and psychological data from a user, the user profile data including attributes with resource level data for the user, the physical data including at least one of heart rate, blood pressure, and other biophysical parameters of the user, and the psychological data including at least some basic needs satisfaction inventory (BNSI) parameters of the user;
   (ii) process the physical data and psychological data to generate metric data including parameters for comparison against criteria data for conditions, the metric data representing satisfaction scores for BNSI categories obtained using the BNSI parameters;
   (iii) generate risk profile data using the user profile data, the parameters, the metric data, and the criteria data;
   (iv) generate recommendation data based on the user profile data, the parameters, the metric data, and the criteria data, the recommendation data representing recommendations for the user relating to the conditions and including activity data representing different activities to be performed by the user, the activity data being generated for each BNSI category based on said satisfaction scores by:
      (a) retrieving all activities for the BNSI category for consideration;
      (b) generating a difference value for each of the attributes of the user by comparing the attributes of the user with corresponding attributes of each of the retrieved activities; and
      (c) selecting a subset of the retrieved activities as at least one of the different activities based on the difference values generated; and
   (v) generate an output interface to provide a risk profile based on the risk profile data and the recommendation data, the risk profile presenting to the user risk levels associated with the conditions and recommendations based on the recommendation data, the recommendations including an activity recommendation to address at least one psychological condition.

2. A diagnostic system as claimed in claim 1, further comprising:
   a diagnostic kit including diagnostic equipment for use by the user to obtain the physical data.

3. A diagnostic system as claimed in claim 1, wherein the other biophysical parameters include at least one of:
   (i) body mass index (BMI) parameters;
   (ii) a waist circumference parameter;
   (iii) a triglycerides (TG) parameter;
   (iv) a cholesterol parameter;
   (v) a fasting glucose (FG) parameter; and
   (vi) a heart rate parameter.

4. A diagnostic system as claimed in claim 3, wherein the conditions relate to unsatisfactory levels of the parameters as determined by the criteria data, and the conditions include metabolic syndrome.

5. A diagnostic system as claimed in claim 1, wherein the psychological parameters include health related quality of life survey score parameters, and the processor, using the survey score parameters, is configured to generate metric data representing physical and mental health score parameters.

6. A diagnostic system as claimed in claim 1, wherein the recommendations represent prevention and intervention recommendations.

7. A diagnostic system as claimed in claim 1, wherein the input interface includes an interface configured to submit compliance data representing compliance by the user with the recommendations.

8. A diagnostic system as claimed in claim 1, wherein the system is connected to a communications network and the input and output interfaces are accessed by the user using a client device to submit the data and receive the risk profile.

9. A diagnostic system as claimed in claim 1, wherein the communications network includes the Internet, and the client device includes a browser configured to access and render the interfaces.

10. A diagnostic system as claimed in claim 1, wherein the system is configured to store data submitted by the user at different times as historical data, and the analyzer is further configured to display the risk profile based on the historical data.

11. A diagnostic system as claimed in claim 1, wherein the risk profile is presented in the form of a report document.

12. A diagnostic system as claimed in claim 1, wherein the blood pressure parameters include a systolic blood pressure (SBP) parameter and a diastolic blood pressure (DBP) parameter.

13. A diagnostic system as claimed in claim 1, wherein the processor is further configured to generate metric data parameters using the waist circumference parameter, gender and ethnicity parameters of the user profile data, the TG parameter, the cholesterol parameter, the blood pressure parameters and the FG parameter to generate risk profile data for metabolic syndrome.

14. A diagnostic system as clamed in claim 1, wherein the body mass index parameters include height and weight of the user, and are used to generate metric data representing the body mass index (BMI) for the user.

15. A diagnostic system as claimed in claim 1, wherein the activity data is generated with an activity level for each BNSI category based on the score for the category.

16. A diagnostic system as clamed in claim 1, wherein the recommendation data for diet and exercise is generated on the basis of the BMI metric data and recommendation data generated using the waist circumference, TG, cholesterol, blood pressure, and FG parameters.

17. A method executed by a diagnostic computer system, comprising:
generate a user interface to receive user profile data, physical data and psychological data from a user, the user profile data including attributes with resource level data for the user, the physical data including at lest one of heart rate, blood pressure and other biophysical parameters of the user, and the physiological data including basic needs satisfaction inventory (BNSI) parameters of the user;
processing the physical data and psychological data to generate results data based on criteria data for conditions, and the BNSI parameters are used to generate results data representing satisfaction scores for BNSI categories;
generating risk profile data using the results data and the criteria data;
generating recommendation data using the user profile data and the results data, the recommendation data representing recommendations for the user relating to the conditions and including activity data representing different activities to be performed by the user, the activity data being generated for each BNSI category based on said satisfaction scores by:
(a) retrieving all activities for the BNSI category for consideration;
(b) generating a difference value for each of the attributes of the user by comparing the attributes of the user with corresponding attributes of each of the retrieved activities; and
(c) selecting a subset of the retrieved activities as at least one of the different activities based on the difference values generated; and
generating an output interface to provide a risk profile based on the risk profile data and the recommendation data, the risk profile presenting to the user risk levels associated with the conditions and recommendations based on the recommendation data, the recommendations including an activity recommendation to address at least one psychological condition.

18. A method as claimed in claim 17, wherein the other parameters include at least one of:
(i) body mass index (BMI) parameters;
(ii) a waist circumference parameter;
(iii) a triglycerides (TG) parameter;
(iv) a cholesterol parameter;
(v) a fasting glucose (FG) parameter; and
(vi) a heart rate parameter.

19. A method as claimed in claim 18, wherein the conditions relate to unsatisfactory levels of the parameters as determined by the criteria data, and the conditions include metabolic syndrome.

20. A method as claimed in claim 17, wherein the parameters include health related quality of life survey score parameters, and the survey score parameters are used to generates results data representing physical and mental health score parameters.

21. A method as claimed in claim 17, wherein the recommendations represent prevention and intervention recommendations.

22. A method as claimed in claim 17, further including providing an interface configured to submit compliance data representing compliance by the user with the recommendations.

23. A method as claimed in claim 17, further including storing data submitted by the user at different times as historical data, and the historical data to generate the results data.

24. A process as claimed in claim 17, wherein the blood pressure parameters include a systolic blood pressure (SBP) parameter and a diastolic blood pressure (DBP) parameter.

25. A method as claimed in claim 24, further including using the waist circumference parameter, gender and ethnicity parameters of the user profile data, the TG parameter, the cholesterol parameter, the blood pressure parameters and the FG parameter to generate results data for metabolic syndrome.

26. A method as claimed in claim 17, wherein the body mass index parameters include height and weight of the user, and are used to generate results data representing the body mass index (BMI) for the user.

27. A method as clamed in claim 17, wherein the activity data is generated with an activity level for each BNSI category based on the score for the category.

28. A method as clamed in claim 27, wherein the recommendation data for diet and exercise is generated on the basis of the BMI results data and recommendation data generated using the waist circumference, TG, cholesterol, blood pressure, and FG parameters.

29. A non-transitory computer-readable medium having processor-readable code that causes one or more processors to perform a method, comprising:
receiving user profile data, physical data and psychological data from a user, the user profile data including attributes with resource level data for the user, the physical data including blood pressure and other parameters of the user, and the physiological data including basic needs satisfaction inventory (BNSI) parameters;
processing the physical data and psychological data to generate results data based on criteria data for conditions, and the BNSI parameters are used to generate results data representing satisfaction scores for BNSI categories;
generating risk profile data using the results data and the criteria data;
generating recommendation data using the user profile data and the results data, the recommendation data including activity data representing the different activities to be performed by the user and generated for each BNSI category based on said satisfaction scores by:
(a) retrieving all activities for the BNSI category for consideration;
(b) generating a difference value for each of the attributes of the user by comparing the attributes of the user with corresponding attributes of each of the retrieved activities; and (c) selecting a subset of the retrieved activities as at least one of the different activities based on the difference values generated; and; and providing, based on the results data, the risk profile data, and the recommendation data, the user with a risk level associated with the conditions and activities to address the conditions, the recommendations including an activity recommendation to address at least one psychological condition.

30. A system as clamed in claim 1, wherein the output interface is further configured to display the risk profile.

31. A method as claimed in claim 17, wherein the providing includes displaying the risk level.

32. A diagnostic system as claimed in claim 1, wherein the plurality of attributes of the user includes a psychological attribute and the corresponding attributes of the activities includes a corresponding psychological attribute.

33. A diagnostic system as claimed in claim 1, wherein the processor is configured to:

determine whether the user's risk profile falls outside a threshold of a medical diagnostic criterion; and cause the output interface to output an alert suggesting the user to contact a health professional if the user's risk profile falls outside the threshold of the medical diagnostic criterion.

34. A diagnostic system as claimed in claim 33, wherein the medical diagnostic criterion is a psychological criterion and the health professional is a mental health professional.

35. A diagnostic system as claimed in claim 1, wherein the processor is configured to determine, from a plurality of response levels, a response level appropriate for each satisfaction score for each BNSI categories, the plurality of response levels including:

no activity recommendation needed;

some activity recommendation needed; and generating advise to seek advice from a mental health professional.

* * * * *